(12) United States Patent
Guillemin et al.

(10) Patent No.: US 12,195,504 B2
(45) Date of Patent: Jan. 14, 2025

(54) ANTI-INFLAMMATORY COMPOUNDS AND METHODS OF USE

(71) Applicant: University of Oregon, Eugene, OR (US)

(72) Inventors: Karen Guillemin, Eugene, OR (US); Annah Rolig, Eugene, OR (US); Emily Sweeney, Eugene, OR (US)

(73) Assignee: University of Oregon, Eugene, OR (US)

( * ) Notice: Subject to any disclaimer, the term of this patent is extended or adjusted under 35 U.S.C. 154(b) by 49 days.

(21) Appl. No.: 17/533,320

(22) Filed: Nov. 23, 2021

(65) Prior Publication Data

US 2022/0073577 A1    Mar. 10, 2022

Related U.S. Application Data

(60) Division of application No. 16/943,763, filed on Jul. 30, 2020, now Pat. No. 11,208,445, which is a division of application No. 15/883,999, filed on Jan. 30, 2018, now Pat. No. 10,752,662, which is a continuation-in-part of application No. 15/311,667, filed as application No. PCT/US2015/031052 on May 15, 2015, now abandoned.

(60) Provisional application No. 61/994,601, filed on May 16, 2014.

(51) Int. Cl.
| | | |
|---|---|---|
| C07K 14/47 | (2006.01) | |
| A61P 29/00 | (2006.01) | |
| C07K 4/12 | (2006.01) | |
| C12N 15/70 | (2006.01) | |

(52) U.S. Cl.
CPC .......... C07K 14/4702 (2013.01); A61P 29/00 (2018.01); C07K 4/12 (2013.01); C12N 15/70 (2013.01)

(58) Field of Classification Search
CPC ....... C07K 14/4702; C07K 4/12; A61P 29/00; C12N 15/70
See application file for complete search history.

(56) References Cited

U.S. PATENT DOCUMENTS

2017/0096457 A1    6/2017   Oregon

FOREIGN PATENT DOCUMENTS

| WO | WO 01/34175 | 5/2001 |
| WO | WO 2011/160062 | 12/2011 |

OTHER PUBLICATIONS

Bates et al., "Intestinal Alkaline Phosphate Detoxifies Lipopolysaccharide and Prevents Inflammation in Zebrafish in Response to the Gut Microbiota," *Cell Host & Microbe*, 2(6):371-382, 2007.
Bomar et al., "Draft Genome Sequence of Aeromonas veronii Hm21, a Symbiotic Isolate from the Medicinal Leech Digestive Tract," *Genome Announcements*, 1(5):e00800-13, 2 pages, 2013.
Bowie et al., "Deciphering the Message in Protein Sequences: Tolerance to Amino Acid Substitutions," *Science*, vol. 247, No. 4948, pp. 1306-1310, 1990.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111, pp. 2129-2138, 1990.
Earl et al. Uniprot entry K1 JBU6_9GAMM/NCBI Id 1073385; EMBL:EKB25247.1; Nov. 12, 2012 (1 page).
European Nucleotide Archive Accession No. ERF65215.1, Sep. 6, 2013, 2 pages.
International Search Report and Written Opinion of the International Searching Authority, mailed Sep. 17, 2019 for corresponding International Application No. PCT/US2019/015675, 12 pages.
Lazar et al., "Transforming Growth Factor α: Mutation of Aspartic Acid 47 and Leucine 48 Results in Different Biological Activities," *Molecular and Cell Biology*, vol. 8, No. 3, pp. 1247-1252, 1988.
Maltz & Graf, "The type II secretion system is essential for erythrocyte lysis and gut colonization by the leech digestive tract symbiont," *App Envir Microbio* 77(2):597-603, 2011.
NCBI Reference Sequence WP_021230730, "Hypothetical protein [*Aeromonas veronii*]", Sep. 21, 2013 (1 page).
Philip et al., "Development of a Zebrafish Sepsis Model for High-Throughput Drug Discovery," *Molecular Medicine*, vol. 23, pp. 134-148, 2017.
Renshaw et al., "A transgenic zebrafish model of neutrophilic inflammation," *Blood* 108:3976-3978, 2006.
Rolig et al., "The enteric nervous system promotes intestinal health by constraining microbiota composition," *PLOS Biol.* 15(2):e2000689, 2017 (22 pages).
Uniprot Accession No. A0A0E2LHY9; May 27, 2015, 1 page.

*Primary Examiner* — Robert A Zeman
(74) *Attorney, Agent, or Firm* — Klarquist Sparkman, LLP

(57) ABSTRACT

Methods of treating or inhibiting inflammation in a subject include administering an anti-inflammatory protein to the subject. In some embodiments, the protein has at least 80% sequence identity to the amino acid sequence set forth as SEQ ID NO: 1, SEQ ID NO: 11, or fragments thereof. Isolated polypeptides, nucleic acids, and recombinant vectors including a nucleic acid encoding the anti-inflammatory protein (such as a nucleic acid encoding a protein with at least 80% sequence identity to SEQ ID NO: 1, SEQ ID NO: 11, or fragments thereof) operably linked to a heterologous promoter are also disclosed.

6 Claims, 27 Drawing Sheets
Specification includes a Sequence Listing.

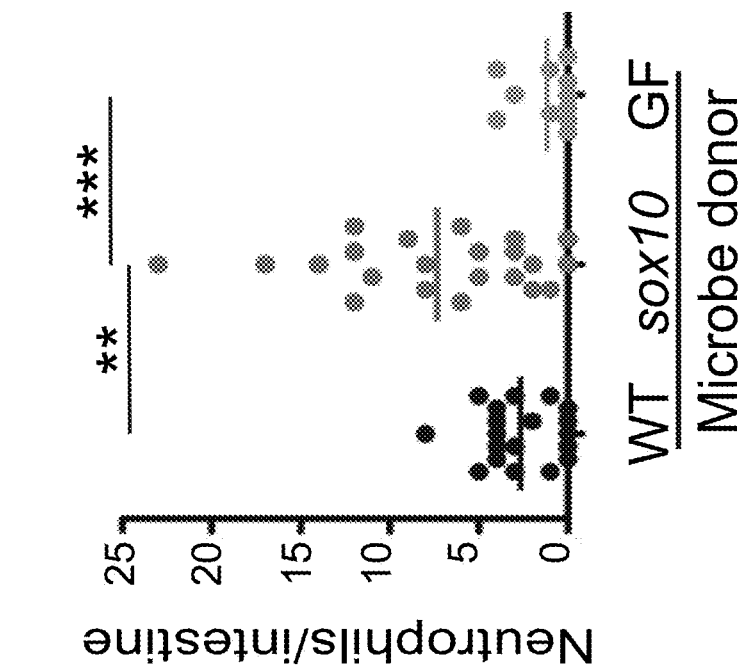
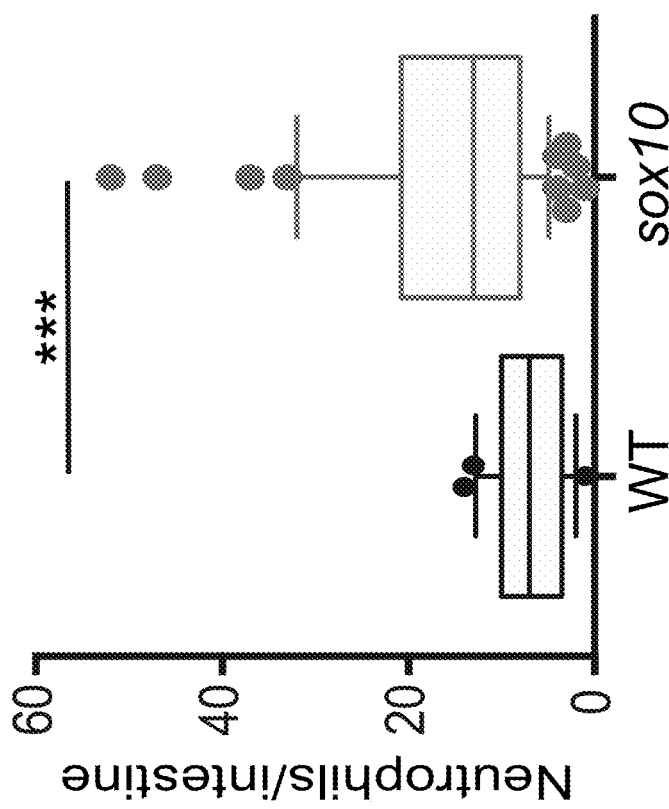
FIG. 9C
FIG. 9D

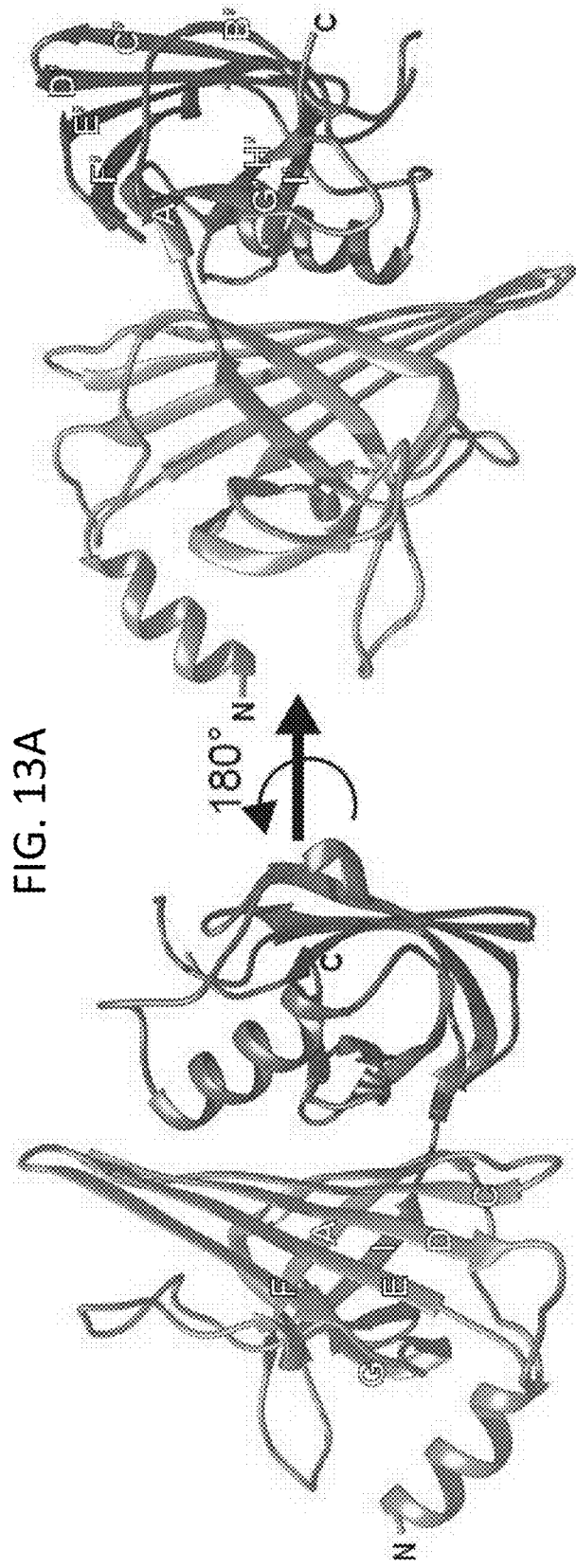
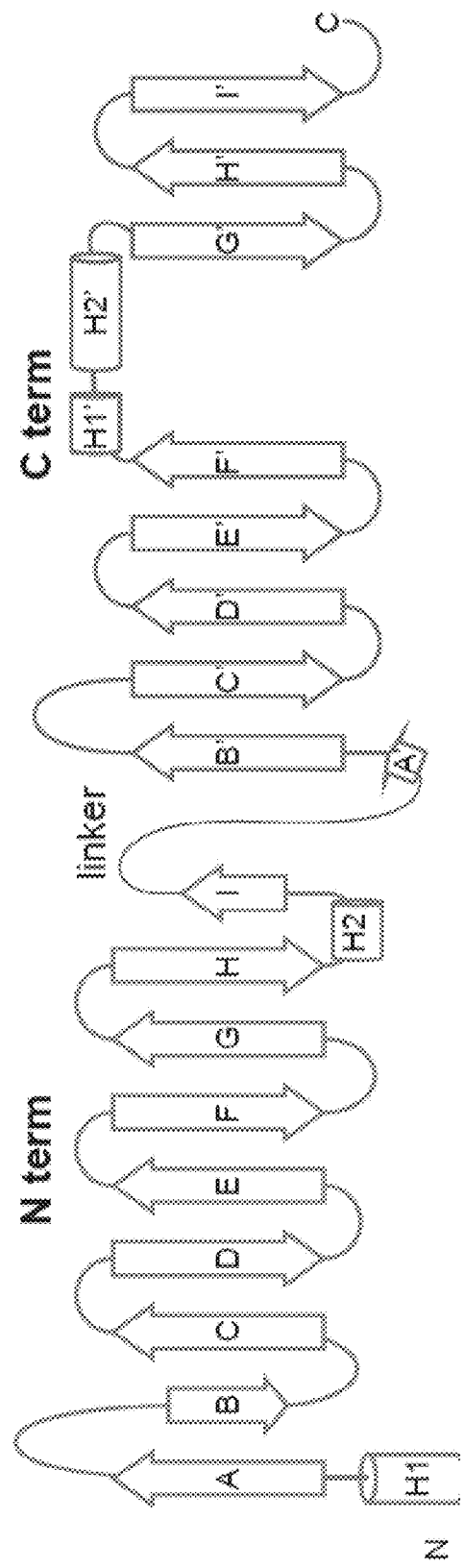
FIG. 13A
FIG. 13B

EXHIBIT A
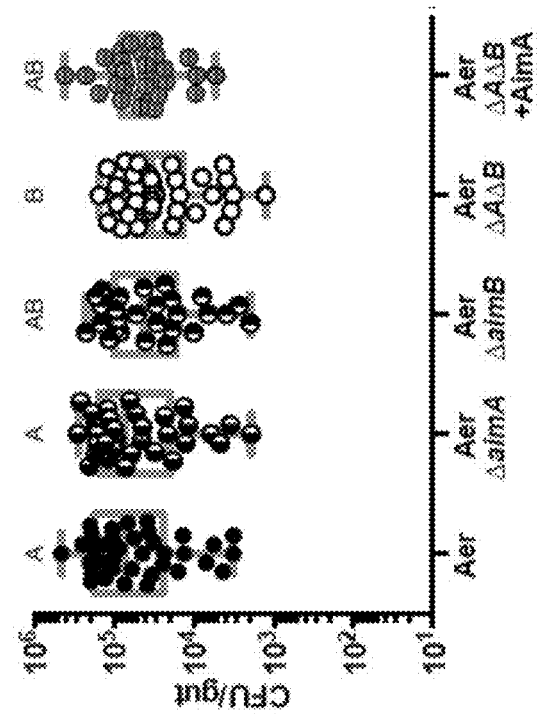
FIG. 19A
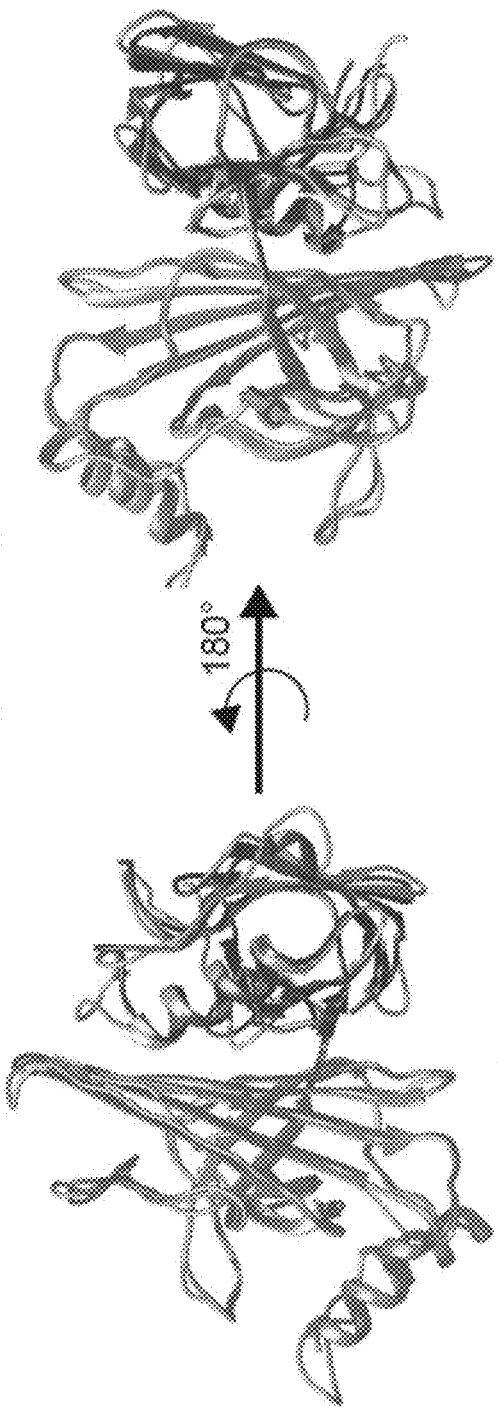
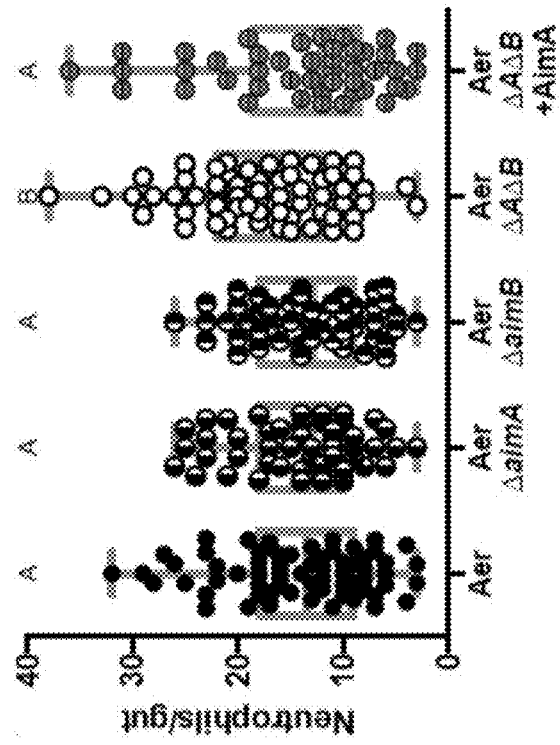
FIG. 19B
FIG. 19C

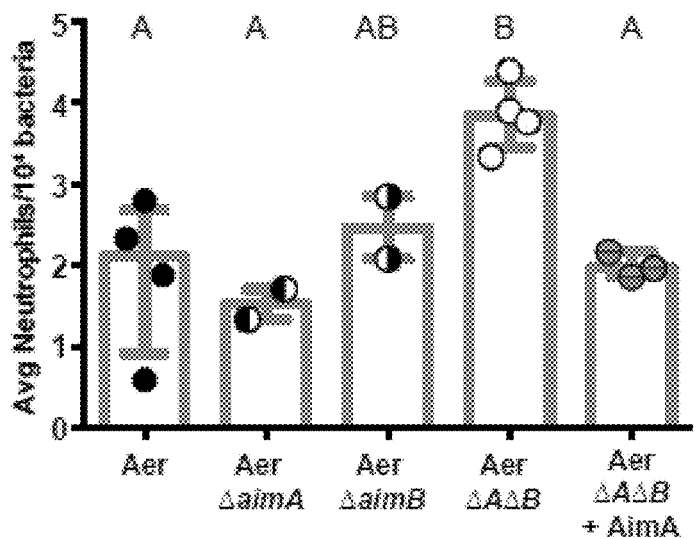
FIG. 20A
FIG. 20B
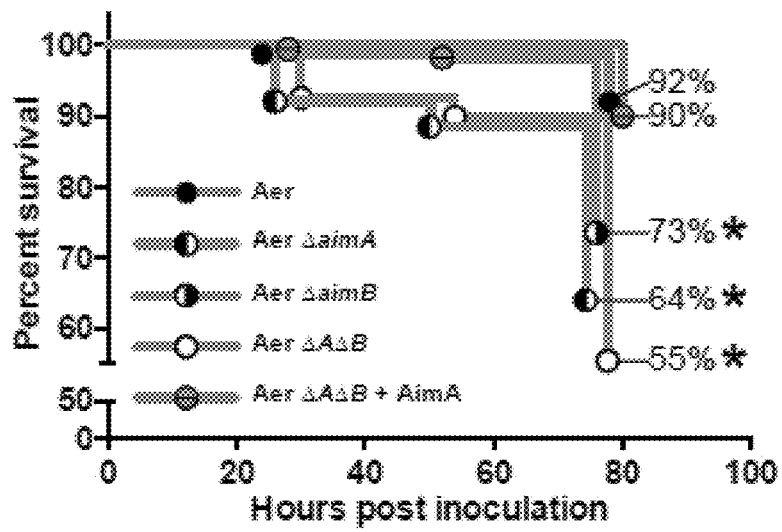
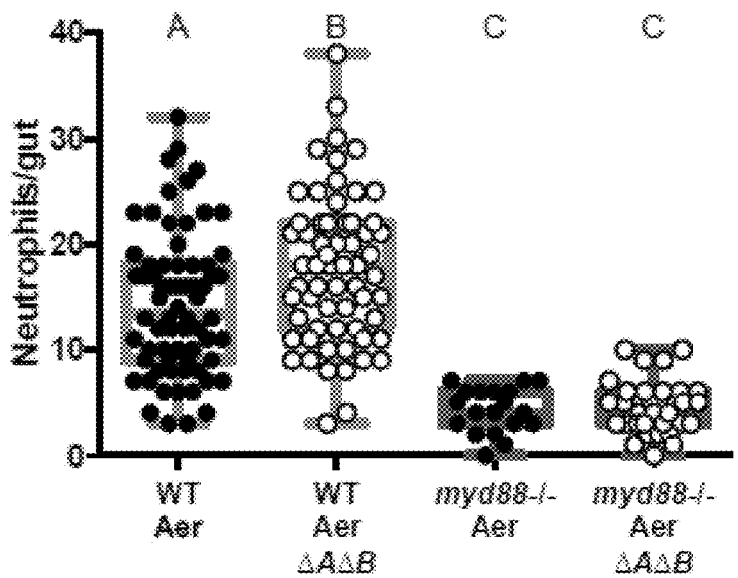
FIG. 20C

```
                            SEQUENCE LISTING

<160> NUMBER OF SEQ ID NOS: 30

<210> SEQ ID NO 1
<211> LENGTH: 313
<212> TYPE: PRT
<213> ORGANISM: Aeromonas veronii

<400> SEQUENCE: 1

Met Lys Met His Asn Lys Ala Leu Leu Ala Ile Ala Cys Ala Ala Ala
1               5                   10                  15

Leu Ser Ala Cys Asp Ser Glu Lys Ala Ala Asn Ser Ile Ala Lys Arg
            20                  25                  30

Val Pro Leu Ala Leu Pro Glu Ala Gly Leu Tyr Gln Ala Asn Leu Met
        35                  40                  45

Ser Arg Asp Gly Asp Lys Ala Thr Pro Arg Met Ile Lys Asp Leu Asp
    50                  55                  60

Gly Leu Ala Leu Val Tyr Pro Lys Gly Glu Thr Val Gln His Trp Gly
65                  70                  75                  80

Val Trp Val Asp His Gln Val Gly Lys Val Glu Thr Asn Ser Gln Trp
                85                  90                  95

Leu Gly Gln Ala Asp Gln Lys Ala Asp Lys Asp Gly Ile Tyr Pro Val
            100                 105                 110

Gln Leu Ile Arg Asn Ser Glu Arg Leu Gly Thr Ser Thr Ala Leu Ser
        115                 120                 125

Ser Val Thr Asn Asp His Asn Leu Ile Thr Phe Gln Asp Gln Pro Val
    130                 135                 140

Ile Asp Leu Gln Gly Lys Glu Ile Lys Arg Trp Val Phe Asp Phe Thr
145                 150                 155                 160

Arg Thr Gly Thr Lys Phe Ser Asp Asn Ser Pro Ile Tyr Ser Gly Phe
                165                 170                 175

Ser Gly His Val Ala Val Thr Ala Leu Thr Thr Lys Ala Val Thr Thr
            180                 185                 190

Ala Ser Trp Ser Ala Thr Asp Ser Asp Gly Phe Ser Ser Glu Met Val
        195                 200                 205

Gly Lys Val Asp Thr Thr Asn Asn Gly Gly Lys Leu Thr Val Ala Ile
    210                 215                 220

Glu Phe Pro Ala Ala Gly Cys Thr Leu Val Gly Glu Gly Ser Ala Thr
225                 230                 235                 240

Ala Gly Leu Ser Lys Leu Thr Met Thr Gly Phe Gly Lys Cys Asn Phe
                245                 250                 255

Lys Gln Ser Ala Ala Thr Pro Ile Glu Asn Leu Trp Asn Ala Ala
            260                 265                 270

Leu Ala Arg Ala Met Asp Asn Arg Val Ala Tyr Val Thr Thr Phe Thr
        275                 280                 285

Ala Asp Ala Lys Lys Glu Ala Leu Val Ile Gly Phe Pro Asp Thr Asn
    290                 295                 300

Gly Leu Leu Ile Thr Ala Asp Lys Arg
305                 310

<210> SEQ ID NO 2
```

```
<211> LENGTH: 942
<212> TYPE: DNA
<213> ORGANISM: Aeromonas veronii

<400> SEQUENCE: 2
atgaaaatgc acaacaaagc gctgctggcc atcgcctgcg ccgccgccct gtctgcctgt      60
gacagcgaaa aagctgccaa cagcattgcc aagcgggtgc cgctggctct gcctgaggcg     120
ggtctttacc aagcgaatct gatgagccgc gacggcgaca aggcgacgcc gcgcatgatc     180
aaggatctgg atggtctggc gctggtctac ccgaagggtg aaaccgtgca gcactggggt     240
gtctgggtgg atcatcaggt gggcaaggtc gagaccaaca gccagtggtt ggggcaggct     300
gaccagaaag ccgacaaaga cgggatctac ccggtgcagt tgatccgcaa cagcgaacgg     360
ctcggcacca gcactgcgct cagctcggtg accaacgacc acaacctcat caccttccag     420
gatcagccgg tcatcgatct gcagggcaag gagatcaagc gctgggtttt tgatttcacc     480
cggactggca ccaagttctc cgacaactcc cccatctatt ccggtttcag cggtcatgtg     540
gcggtgacgg ccctgaccac caaagcggtg accacggcca gctggagtgc acggacagc     600
gatggcttca gcagcgaaat ggtgggcaag gtggatacca ccaacaacgg cggcaagctg     660
acggtagcga tcgagtttcc ggcggcaggt tgtacgctgg tgggcgaggg gagtgccact     720
gcagggttga gtaagctgac catgaccggg tttggcaagt gcaacttcaa gcaatccgct     780
gcagccacgc cgatcgaaaa cctctggaat gctgctctgg cccgggcgat ggataacaga     840
gtcgcctatg tcaccacctt taccgcggat gccaaaaaag aggcgctggt catcggcttc     900
cccgacacca tggcttgct gatcaccgct gacaagcgat aa                          942

<210> SEQ ID NO 3
<211> LENGTH: 35
<212> TYPE: DNA
<213> ORGANISM: Artificial Sequence
<220> FEATURE:
<223> OTHER INFORMATION: Synthetic oligonucleotide - AP forward primer

<400> SEQUENCE: 3
cgtacatatg atgaaaatgc acaacaaagc gctgc                                  35

<210> SEQ ID NO 4
<211> LENGTH: 34
<212> TYPE: DNA
<213> ORGANISM: Artificial Sequence
<220> FEATURE:
<223> OTHER INFORMATION: Synthetic oligonucleotide - AP reverse primer

<400> SEQUENCE: 4
ctgactcgag ttatcgcttg tcagcggtga tcag                                   34

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 5
gcgacagcaa ggaataaaaa ctc                                               23

<210> SEQ ID NO 6
<211> LENGTH: 23
<212> TYPE: DNA
<213> ORGANISM: Artificial Sequence
```

-continued

```
<220> FEATURE:
<223> OTHER INFORMATION: Synthetic oligonucleotide primer

<400> SEQUENCE: 6
cacccctgcc gttagctgct tat                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 7
ctaaggagga tattcatatg cat                                              23

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
gatggtctgg gtattgccgt tg                                               22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 9
cgaagcagct ccagcctaca ca                                               22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 10
gctgttcgtc atcgatcggc gc                                               22

<210> SEQ ID NO 11
<211> LENGTH: 330
<212> TYPE: PRT
<213> ORGANISM: Aeromonas veronii

<400> SEQUENCE: 11

Met Lys Lys Thr Thr Leu Ser Trp Ala Ile Ile Gly Ala Leu Gly Leu
1               5                   10                  15

Val Gly Cys Gly Gly Gly Gly Asp Ser Gly Gly Gly Thr Thr
            20                  25                  30

Pro Pro Glu Pro Gln Pro Arg Ala Leu Pro Val Ala Gly Val Tyr Leu
        35                  40                  45

Pro Val Leu Met Asp Ala Gln Gly Gln Leu Ile Asn Arg Pro Val Asn
    50                  55                  60

Asp Ser Tyr Arg Ala Val Gly Leu Val Tyr Pro Ala Ser Thr Glu Gly
65                  70                  75                  80

Thr Gly Trp Ala Met Asn Ile Ala Glu Lys Arg Ser Ala Thr Val Ser
```

```
            85                  90                  95
Thr Tyr Thr Phe Pro Gln Gly Phe Ser Ser Leu Asn Lys Gly Glu Gly
            100                 105                 110

Tyr Pro Leu Thr Leu Ser Leu Leu Val Asn Lys Ser Gln Pro Ser Thr
            115                 120                 125

Phe Asp Ser Ala Glu Gln Lys Ser Asn Thr Asn Val Asp Gly Leu Val
            130                 135                 140

Lys Val Ala Ser Val Pro Asp Thr Ala Gly Ser Ser Gln Ser Leu Trp
145                 150                 155                 160

Val Leu Asp Tyr Arg Pro Val Lys Ala Lys Ile Asp Ser Ala Leu Thr
                165                 170                 175

Ile Gln Asn Trp Gly Gly Gln Val Ala Leu Gln Pro Met Val Thr Ala
                180                 185                 190

Pro Ile Asn Ala Asp Ser Trp Tyr Asn Leu Gly Glu Ser Ala Leu Phe
                195                 200                 205

Gln Asp Phe Lys Thr Glu Arg Ser Asn Asn Gly Leu Gly Ile Lys Leu
            210                 215                 220

Thr Ile Leu Phe Lys Glu Gly Cys Ser Val Ser Gly Glu Thr Glu Ala
225                 230                 235                 240

Asn Thr Gln Gly Leu Asn Lys Leu Thr Leu Thr Gly Trp Asn Asn Arg
                245                 250                 255

Ser Cys Ser Phe Asn Thr Leu Thr Gly Pro Ala Asp Ile Lys Glu Gly
                260                 265                 270

Lys Ile Tyr Glu Gly Leu Trp Glu Lys Arg Met Arg Glu Phe Ala Asp
                275                 280                 285

Arg Asn Ala Ser Val Thr Ala Tyr Leu Thr Met Lys Pro Gly Ser Asn
            290                 295                 300

Gly Gln Lys Asp Thr Leu Val Leu Gly Ile Pro Glu Ile Thr Gly Ile
305                 310                 315                 320

Thr Pro Phe Leu Leu Glu Ala Gln Pro Leu
                325                 330

<210> SEQ ID NO 12
<211> LENGTH: 330
<212> TYPE: PRT
<213> ORGANISM: Aeromonas allosaccharophila

<400> SEQUENCE: 12

Met Met Asn Ser His Lys Trp Val Leu Leu Gly Ala Cys Met Ala Thr
1               5                   10                  15

Leu Ser Gly Cys Gly Gly Ser Asp Asp Asn Lys Ser Thr Thr Ala Thr
            20                  25                  30

Ser Val Ala Pro Val Ser His Val Ala Thr Thr Leu Lys Ala Gly Ile
            35                  40                  45

Val Leu Pro Gln Pro Gly Val Tyr Gln Thr Thr Leu Leu Thr Arg Asp
        50                  55                  60

Asp Pro His Gln Thr Leu Val Asn Phe Ala Gly Leu Ala Ile Val Tyr
65                  70                  75                  80

Pro Gln Arg Asp Ala Gln Leu Arg Trp Asp Ile Trp Ala Asp Asp Gly
            85                  90                  95

Ala Val Ala Thr Trp Trp Leu Gly Gln Ala Gly Met Gln Ser Asp Ser
            100                 105                 110

Thr Glu Pro Ser Thr Leu Arg Leu Thr Arg Ile Ser Arg Asn Lys Val
            115                 120                 125
```

```
Ala Asp Ser Ala Val Leu Thr Arg Asp Asp Ser Gly Thr Gln Leu Val
    130                 135                 140

Pro Ser Asn Tyr Gln Arg Gln Ser Ser Val Pro Ser Gln Val Met Ile
145                 150                 155                 160

Lys Thr Met Pro Val Ile Asn Glu Lys Gly Glu Arg Val Arg Tyr Ser
                165                 170                 175

Ala Phe Asp Leu Ser Ser Thr Gly Thr Thr Val Tyr His Asn Trp Asn
            180                 185                 190

Gly Gln Val Gly Ile Thr Ala Val Asn Thr Thr Asp Ile Lys Ser Glu
                195                 200                 205

Thr Trp Leu Thr Gly Asn Gly Leu Ala Thr Asp Met Leu Gly Asn Thr
    210                 215                 220

Glu Leu Thr Asn Asn Asp Gly Lys Leu Ser Val Val Ile Gln Leu Pro
225                 230                 235                 240

Ser Ala Gly Cys Lys Leu Phe Gly Gly Ala Lys Glu Ser Asn His
                245                 250                 255

Ala Leu Ser Lys Leu Thr Phe Thr Gly Phe Glu Lys Cys Lys Phe Val
            260                 265                 270

Glu Phe Asn Asp Ala Asn Trp Ser Gln Ser Asp Tyr Lys Asn Thr Ala
    275                 280                 285

Gly Leu Ala Gln Val Lys Asp Thr Ala Thr Ala Tyr Ile Ala Glu Phe
    290                 295                 300

Asn Asp Ala Asn Asn Lys Asn Thr Val Val Ile Gly Phe Pro Ala Leu
305                 310                 315                 320

Asp Gly Val Ile Phe Thr Leu Lys Lys Gly
                325                 330

<210> SEQ ID NO 13
<211> LENGTH: 315
<212> TYPE: PRT
<213> ORGANISM: Aeromonas hydrophila

<400> SEQUENCE: 13

Met Arg Met His His Lys Ala Val Leu Ala Ile Ala Cys Thr Ala Ala
1               5                   10                  15

Leu Ser Ala Cys Asp Ser Glu Lys Ala Ala Asn Ser Ile Ala Lys Arg
                20                  25                  30

Ala Pro Leu Pro Leu Pro Asp Ala Gly Val Tyr Glu Ala Asn Leu Leu
            35                  40                  45

Ser Arg Asp Gly Asp Gln Gly Pro Leu Lys Met Ile Lys Gly Val Glu
50                  55                  60

Gly Leu Ala Leu Val Tyr Pro Lys Gly Asp Gly Glu Gln Arg Trp Gly
65                  70                  75                  80

Val Trp Val Glu Asn Asp Gly Lys Ser Ile Thr Ser Ser Gln Trp Met
                85                  90                  95

Gly Gln Ala Ala Gln Lys Glu Asn Lys Asp Gly Ile Tyr Pro Val Leu
            100                 105                 110

Leu Glu Arg Thr Ser Val Arg Gly Lys Arg Leu Asp Ala Gln Ser Asn
        115                 120                 125

Asp His Asn Leu Ile Ser Phe Gln Asp Lys Ala Val Thr Asp Leu Ala
130                 135                 140

Gly Lys Glu Val Lys Arg Trp Thr Phe Asp Phe Ser Arg Thr Gly Thr
145                 150                 155                 160

Gln Phe Arg Asp Pro Asp Gln Ser Thr Ala Leu Tyr Arg Asp Trp Ser
                165                 170                 175
```

```
Gly His Leu Ala Val Ser Lys Leu Ala Thr Arg Thr Ile Ser Ser Asp
            180                 185                 190

Ser Trp Arg Val Ala Glu Asp Ala Gly Phe Gly Asp Ala Met Val Gly
        195                 200                 205

Met Ile Arg Ser Thr Asn Asn Gly Gly Ser Leu Thr Leu Glu Ile Glu
    210                 215                 220

Phe Pro Lys Ala Gly Cys Thr Leu Thr Gly Lys Gly Ser Ala Glu Ser
225                 230                 235                 240

Gly Lys Gly Leu Ser Lys Leu Asn Leu Ser Gly Phe Gly Lys Cys Asn
                245                 250                 255

Phe Arg Ala Ser Ser Asp Leu Ser Pro Leu Glu Asn Lys Trp Met Leu
                260                 265                 270

Gly Leu Ala Lys Ala Lys Glu Gly Ala Thr Ala Tyr Val Ala Ala Phe
            275                 280                 285

Glu Ile Pro Asp Thr Arg Lys Thr Thr Leu Val Val Gly Phe Pro Glu
        290                 295                 300

Gln His Gly Leu Met Met Val Gly Glu Lys Tyr
305                 310                 315

<210> SEQ ID NO 14
<211> LENGTH: 315
<212> TYPE: PRT
<213> ORGANISM: Aeromonas salmonicida

<400> SEQUENCE: 14

Met His His Lys Ala Met Leu Ala Ile Ala Cys Thr Ala Ala Leu Ser
1               5                   10                  15

Ala Cys Asp Ser Glu Lys Ala Ala Asn Ser Ile Ala Lys Arg Ala Pro
                20                  25                  30

Leu Pro Leu Pro Asp Ala Gly Leu Tyr Glu Ala Ser Leu Leu Ser Arg
            35                  40                  45

Asp Asn Asp Lys Ala Ser Phe Lys Met Ile Lys Gly Leu Glu Gly Met
        50                  55                  60

Ala Leu Ile Tyr Pro Lys Ala Asp Arg Glu Gln Arg Trp Gly Val Trp
65                  70                  75                  80

Val Asp Lys Asp Ala Gly Lys Val Ala Thr Asn Ser Gln Trp Ile Gly
                85                  90                  95

Lys Ala Ala Gln Lys Glu Asn Lys Asp Gly Ile Tyr Pro Val Leu Leu
            100                 105                 110

Glu Arg Thr Ser Glu Arg Gly Asn Lys Val Asp Ser Gln Ser Asn Asp
        115                 120                 125

His Asn Leu Ile Ser Phe Arg Asp Gln Ser Val Ile Asp Leu Asn Gly
    130                 135                 140

Lys Glu Leu Lys Arg Trp Thr Phe Asp Phe Thr Arg Thr Gly Thr Gln
145                 150                 155                 160

Phe Arg Glu Pro Asp Gln Ser Thr Thr Leu Tyr Pro Ser Trp Ser Gly
                165                 170                 175

His Val Ala Val Ser Lys Leu Thr Thr Arg Ala Ile Ser Ser Asp Ser
            180                 185                 190

Trp Ser Val Ala Asp Asp Glu Gly Phe Ala Asp Ala Met Val Gly Gln
        195                 200                 205

Ile Lys Ser Thr Asn Asn Ser Gly Ser Leu Thr Val Glu Met Glu Phe
    210                 215                 220

Pro Ser Ala Gly Cys Thr Leu Thr Gly Lys Gly Lys Ala Asp Gln His
```

```
                225                 230                 235                 240

Asn Gly Leu Ser Lys Leu Thr Val Ser Gly Phe Gly Lys Cys Arg Phe
            245                 250                 255

Lys Ala Ser Ser Asp Phe Thr Pro Ile Glu Asn Lys Trp Val Leu Ser
            260                 265                 270

Leu Ala Asn Ala Arg Asp Gly Ala Leu Ala Tyr Ala Ala Ala Phe Thr
            275                 280                 285

Ile Pro Asn Thr Lys Gln Thr Ala Leu Val Val Gly Phe Pro Glu Gln
            290                 295                 300

Asn Gly Leu Val Leu Met Ala Asp Lys Gln Pro
305                 310                 315

<210> SEQ ID NO 15
<211> LENGTH: 314
<212> TYPE: PRT
<213> ORGANISM: Aeromonas schubertii

<400> SEQUENCE: 15

Met Lys Phe Arg Phe Thr Ile Leu Ala Ser Thr Leu Ala Leu Leu Ser
1               5                   10                  15

Ala Cys Gly Gly Gly Ser Glu Gly Gly Ser Pro Ala Pro Gln Pro
            20                  25                  30

Lys Pro Gln Pro Met Ala Met Pro Glu Ala Gly Ile Tyr Thr Pro Tyr
            35                  40                  45

Leu Leu Asp Gly Ala Asn Lys Ala Leu Ala Leu Asp Pro Glu Phe Ser
    50                  55                  60

Val Ser Ile Val Tyr Pro Ala Gly Glu Lys Ala Gln Pro Trp Thr Ser
65                  70                  75                  80

Leu Ile Ala Leu Glu Ser Ala Asp Lys Ser Lys Ala Thr Leu Leu Gln
                85                  90                  95

Leu Thr Gly Ser Ala Gly Arg Val Ser Pro Tyr Ala Asn Arg Val Glu
            100                 105                 110

Ser Leu Ile Glu Leu Met Glu Gln Asp Lys Gln Ser Glu Met Cys Ser
        115                 120                 125

Ser Ser Asn Ile Asp Asn Ala Val Leu Lys Pro Met Ser Gln Gly Asn
    130                 135                 140

Val Asn Leu Ala Asp Thr Gly Glu Arg Leu Trp Ile Val Asp Gln Leu
145                 150                 155                 160

Pro Gly Ser Cys Lys Ser Met Ile Ser Gly Trp Ser Gly Lys Val Ala
                165                 170                 175

Leu Lys Pro Tyr Pro Thr Gln Ala Leu Asp Ser Arg His Trp Thr Tyr
            180                 185                 190

Glu Gly Gly Asp Asn Ala Ser Leu Leu Ser Ser Ala Glu Thr Thr Val
        195                 200                 205

Asn Gly Gly Glu Leu His Leu Ala Leu Val Leu Pro His Ala Gly Cys
    210                 215                 220

Arg Leu Glu Gly Ser Gly Gln Ala Gly Asn Gly Leu Asn Arg Ile Val
225                 230                 235                 240

Leu Ser Gly Leu Gln Gln Cys Arg Phe Asp Tyr Tyr Asp Asn Thr Ser
                245                 250                 255

Leu Val Glu Thr Asn Leu Glu Arg Leu Trp Leu Leu Ala Leu Arg Asp
            260                 265                 270

Leu Ala Lys Thr Gln Asn Thr Leu Thr Val Tyr Ala Phe Gly Ile Arg
        275                 280                 285
```

Asp Asp Asp Asn Lys Pro Met Leu Gly Ile Gly Val Pro Asp Val Lys
            290                 295                 300

Gly Leu Val Leu Asp Leu Asp Ser Thr Gln
305                 310

<210> SEQ ID NO 16
<211> LENGTH: 329
<212> TYPE: PRT
<213> ORGANISM: Aeromonas sobria

<400> SEQUENCE: 16

Met Lys Lys Thr Thr Leu Trp Leu Ala Met Val Gly Ala Leu Gly Leu
1               5                   10                  15

Ala Gly Cys Gly Gly Gly Gly Asp Ser Gly Gly Gly Thr Thr
            20                  25                  30

Pro Pro Glu Pro Gln Pro Arg Ala Leu Pro Glu Ala Gly Val Tyr Leu
            35                  40                  45

Pro Val Leu Met Asp Ala Gln Gly Gln Leu Ile Asn Arg Pro Val Asn
        50                  55                  60

Asp Ser Tyr Arg Ala Val Gly Phe Val Tyr Pro Ala Ser Thr Glu Gly
65                  70                  75                  80

Thr Gly Trp Ala Met Asn Ile Ala Glu Lys Arg Ser Ala Thr Val Ser
                85                  90                  95

Thr Tyr Thr Phe Pro Gln Gly Phe Ser Ser Leu Asn Lys Gly Glu Gly
            100                 105                 110

Tyr Pro Leu Thr Leu Ser Leu Leu Val Asn Lys Ser Gln Pro Ser Thr
        115                 120                 125

Phe Asp Ser Ala Glu Gln Lys Ser Asn Thr Asn Val Asp Gly Leu Val
130                 135                 140

Lys Val Ala Ser Val Pro Asp Ala Ala Gly Ser Ser Gln Ser Leu Trp
145                 150                 155                 160

Val Leu Asp Tyr Arg Pro Val Lys Ala Lys Ile Asp Ser Ala Leu Thr
                165                 170                 175

Ile Gln Asn Trp Gly Gly Gln Val Ala Leu Gln Pro Met Val Thr Ala
            180                 185                 190

Pro Ile Asn Ala Asp Ser Trp Tyr Asn Leu Gly Glu Ser Ala Leu Phe
        195                 200                 205

Gln Asp Phe Lys Thr Glu Arg Ser Asn Asn Gly Ser Gly Val Lys Leu
210                 215                 220

Thr Ile Gln Phe Ile Glu Gly Cys Thr Val Ser Gly Glu Thr Glu Ala
225                 230                 235                 240

Asn Thr Pro Gly Leu Asn Lys Leu Thr Leu Thr Gly Trp Lys Glu Cys
                245                 250                 255

Ser Phe Asn Thr Leu Thr Gly Pro Ala Asp Ile Lys Asp Gly Lys Ile
            260                 265                 270

Tyr Glu Gly Leu Trp Glu Thr Lys Met Arg Asp Phe Ala Asn Arg Asn
        275                 280                 285

Ala Ser Val Thr Ala Tyr Leu Thr Met Lys Pro Gly Asn Ser Asn Gly
290                 295                 300

Gln Lys Asp Thr Leu Met Ile Gly Ile Pro Glu Ile Thr Gly Leu Thr
305                 310                 315                 320

Pro Phe Val Leu Glu Val Gln Pro Leu
                325

<210> SEQ ID NO 17

```
<211> LENGTH: 993
<212> TYPE: DNA
<213> ORGANISM: Aeromonas veronii

<400> SEQUENCE: 17
atgaaaaaaa ctacgctttc gtgggcaatt attggtgcat taggtttggt tggttgcggt      60
ggtggtggcg agatagtgg tggtggtggt accacgccac cggagccgca accgagggcg     120
ctgccggtgg ctggcgtcta tctccccgtc ctgatggacg ctcaggggca gttaatcaac     180
cgtccggtca acgacagtta tcgtgcggtc ggtcttgtct atccggcgtc cacagagggc     240
acgggttggg cgatgaacat tgctgagaaa agaagtgcca cagtcagcac ttataccttc     300
cctcaaggct tctcttctct gaataaaggt gagggttacc cactgacgtt gtcgttgctg     360
gtgaacaaaa gccaacccag taccttcgac tcggctgagc aaaagtccaa taccaatgtc     420
gatgggttgg tcaaggtggc gtctgtgcca gatacggcgg aagcagcca gtcactctgg      480 gtactcgatt atcgacccgt caaagccaaa atcgattctg cactcactat tcagaattgg     540
ggcggccaag tggcattgca gccgatggtc actgcgccta tcaacgcgga ctcctggtac     600
aaccttgggg agagtgcact gtttcaagat ttcaaaaccg agcgcagcaa caatggtttg     660
gggatcaagc tgaccatcct gttttaagaa gggtgttctg taagcggtga cagagaggcc     720
aacactcaag gtttgaacaa gctgacgttg actggttgga caatcggtc atgcagtttc      780 aataccttga cagggcctgc tgatatcaaa gagggaaaaa tttatgaggg gctctgggaa     840
aaaaggatgc gcgaatttgc cgatcgcaac gccagtgtca ctgcatatct gaccatgaaa     900
ccgggtagca atggtcagaa agacaccctg gtgctcggta ttccggaaat caccggtatc     960
acgccgttcc tgttggaagc gcaaccactc taa                                  993

<210> SEQ ID NO 18
<211> LENGTH: 990
<212> TYPE: DNA
<213> ORGANISM: Aeromonas allosaccharophila

<400> SEQUENCE: 18
atgatgaaca gtcataaatg ggtattgttg ggggcttgta tggccaccct ttctggctgt      60
ggtggctcag atgataacaa atcaaccaca gcgaccagcg ttgctcctgt ttcccatgtt     120
gcaacaacac tgaaagcagg cattgtgcta ccgcagccag gggtttacca acgacgctg      180 cttacgcgcg atgatccgca ccagacattg gttaatttcg ccggcttggc aatcgtttac     240
ccacaacgtg atgcgcagct gcgttgggat atctgggccg atgatggcgc cgtggctacc     300
tggtggcttg gtcaggccgg aatgcagtcc gatagcacag agccatcgac gctgaggttg     360
acgcgcatta gcagaaataa agtggcagac agtgctgttt tgacgcggga tgattcaggt     420
acgcagctcg tgccatcgaa ttaccagagg caaagcagtg tccccagtca ggtcatgatc     480
aaaaccatgc ccgtcatcaa tgaaaagggt gagcgggtca gatattctgc gtttgatctt     540
tcgagtaccg gaaccacggt atatcacaat tggaatggcc aggttggtat tacagcagtc     600
aacacaacgg atattaagtc agagacatgg ttgactggaa atggcttggc gacagatatg     660
ttaggcaata ccgagttgac taataatgat ggcaagttga gcgtcgttat acaactgcca     720
tcagcaggct gtaaattatt cggtgagggc gcgaaagaga gcaatcacgc attgagcaaa     780 cttacttta ccggattcga gaaatgcaaa tttgttgaat ttaatgatgc caactggagc      840
cagagtgatt ataaaaacac ggcgggtttg gcacaagtaa aagacacggc taccgcatat     900
attgccgagt ttaacgatgc gaataataag aacacagtag ttattggatt cccgcgctg     960
```

```
gatggggtca tatttactct gaaaaaggga                                  990
```

<210> SEQ ID NO 19
<211> LENGTH: 945
<212> TYPE: DNA
<213> ORGANISM: Aeromonas hydrophila

<400> SEQUENCE: 19

```
atgagaatgc accacaaagc cgtgctggcc atcgcctgca ccgccgccct gtccgcctgt   60
gacagcgaga aggcggccaa cagcatcgcc aaacgcgcgc cgctgccgtt gcccgatgcc  120
ggcgtctatg aggcgaacct gctcagccgc gatggcgatc aggggccgct caagatgatc  180
aagggagtgg agggattggc gctggtctac cccaagggg atggcgagca cgctggggc   240
gtctgggtcg agaacgacgg caagtcgatt acctcttcgc aatggatggg gcaggcggcc  300
cagaaagaga acaaggatgg tatctatccg gtgctgctgg agcgcacctc ggtgcggggc  360
aagcggctcg atgcccagag caacgaccac aacctcatca gctttcaaga caaggcggta  420
accgatttgg ctggcaaaga ggtcaagcgc tggacctttg acttcagccg taccggcacc  480
cagttccggg atccggatca gagcaccgcc ctttatcgcg actggagcgg ccaccttgcc  540
gtgagcaagc tcgccacccg gacgatcagc agcgacagct ggcgggtggc agaggatgcc  600
ggttttggcg atgccatggt ggggatgatc cgcagcacca acaatggcgg ctccctgact  660
ctggagatcg aatttcccaa ggcggttgt  accctgaccg gcaagggcag tgcagagtct  720
ggcaaggggc tcagcaagtt aaacctgagc gggtttggca agtgcaactt caaggcatca  780
agcgatctca gcccgcttga aacaagtgg atgctgggcc tagccaaggc caaagagggg  840
gcaacggcct acgtcgccgc gttcgagata ccggacaccc gcaagacgac cctggtggtg  900
ggcttccctg aacagcacgg cctgatgatg gtgggcgaga aatac              945
```

<210> SEQ ID NO 20
<211> LENGTH: 945
<212> TYPE: DNA
<213> ORGANISM: Aeromonas salmonicida

<400> SEQUENCE: 20

```
atgcaccaca aagccatgct ggccatcgcc tgcaccgccg ccctgtccgc ctgcgacagc   60
gagaaagccg ccaacagtat tgccaagcgc gcgccgttgc cactgcctga tgcgggtctt  120
tacgaagcca gcctcttgag ccgcgataat gacaaggcgt cgttcaagat gatcaagggg  180
ctggaaggga tggcactcat ctatcccaag gcggatcgcg agcagcgttg gggtgtctgg  240
gtcgacaagg atgcgggcaa ggtggcaacc aacagccagt ggatcggcaa ggcggctcag  300
aaggagaaca aagatgggat ataccccgtc ttgctggagc gtacctccga gcgtggcaac  360
aaggtcgata gccagagcaa tgaccacaac ctcatcagct ccgtgatca gtcggtgatt  420
gacttgaatg gcaaagagct caagcgctgg acctttgact ttacccgaac cggcacccag  480
ttccgcgagc cggatcagag cacgaccctc tacccatcct ggagcggcca cgtcgccgtc  540
agcaagctga ctacccgggc gatcagcagc gacagctggt cagttgcaga cgatgagggc  600
ttcgccgacg ccatggtggg ccagatcaag agcaccaaca acagcggctc cctgacggtg  660
gagatggaat ccccagcgc cggttgcacc ctgaccggca agggcaaggc cgatcagcac  720
aatgccctga gcaagctgac cgtgagcggc tttggcaagt gccgcttcaa ggcctcaagc  780
gatttcacgc cgattgagaa caagtggggtg ttgagcctgg ccaacgccag agacggggct  840
```

```
ttggcctatg ccgccgcgtt caccatcccc aataccaagc agactgcatt ggtggttggt      900
ttccccgagc aaaacggtct ggtgctgatg gcggacaaac agccc                     945
```

<210> SEQ ID NO 21
<211> LENGTH: 942
<212> TYPE: DNA
<213> ORGANISM: Aeromonas schubertii

<400> SEQUENCE: 21

```
atgaagttca ggtttactat tttggccagc accctggccc tgctctctgc gtgtggcggc       60
ggcggctctg agggcggctc cccggctccc aacccaagc cccagcccat ggccatgccc       120
gaggctggta tctataccccc ctatctgctc gatggcgcca acaaggcgct ggcgttggat     180
cctgagtttt cagtctccat cgtctatccg gccggtgaga aggcgcagcc ctggaccagc     240
ctgatcgcgc tggagagtgc cgataagagc aaggctacgt tgttgcaact gactggcagt     300
gctggtcggg tcagtcccta tgcaaatagg gttgaatctt tgattgagct tatggagcaa     360
gataagcaat cagaaatgtg tagtagtagc aatatcgaca acgcagtttt gaaaccaatg     420 agtcaggggta atgtcaattt ggctgacact ggtgagcgac tctggatcgt ggatcagcta    480
cctggtagct gcaagagcat gatatccggc tggagcggca aggttgccct gaaaccctac     540
ccgacccagg cactggattc gcgtcactgg acttatgagg ggggagataa tgcctctctg     600
ctcagcagtg cagagacgac cgtcaatggc ggtgaattgc acctggctct ggtgttgccc     660
catgccggtt gccgtctgga agggagcggg caggcgggga acgggttaaa tcgtattgtg     720
ctcagtggcc tgcagcagtg ccgcttcgac tattacgaca ataccctcgct ggttgagacc    780 aacctggagc ggttgtggct gcttgccttg gcgatctgg caaagacaca gaatacctg     840 acggtctatg cctttggcat tcgtgatgac acaacaagc ccatgttggg gatcggtgtc      900
ccggacgtga agggactggt actggatctc gattcgaccc ag                        942
```

<210> SEQ ID NO 22
<211> LENGTH: 987
<212> TYPE: DNA
<213> ORGANISM: Aeromonas sobria

<400> SEQUENCE: 22

```
atgaagaaaa caacactttg gttggcaatg gtaggggcat gggggttggc cggttgtggc       60
ggcggtggtg gggatagtgg cggcggcggt accacgccac cggagccaca accaagggcg     120
ctgccggagg ccggcgtcta tctccccgtc ctgatggacg ctcaggggca gttaatcaac     180
cgtccggtca cgacagcta tcgtgcggtc ggttttgtct atccagcgtc cacagagggc     240
acgggttggg cgatgaacat tgctgagaaa agaagtgcca cagtcagcac ttatacccttc    300 cctcaaggtt tttcttctct gaacaaaggt gagggctacc cctgacgtt gtcgttgctg     360 gtgaacaaaa gccagcccag taccttcgac tcggcggagc aaaagtccaa taccaatgtc     420
gatggattgg tcaaggtggc gtctgtgcca gatgcgcgg gaagcagcca gtcactctgg     480
gtgctcgatt atcgacccgt caaagccaaa atcgattcag cgctcactat tcagaattgg     540
ggcggccaag tggcattgca gccgatggta accgcgccaa tcaacgctga ctcttggtac     600
aaccttgggg agagcgcact gtttcaggat ttcaaaaccg agcgcagcaa caatggctcg     660
ggagtcaagc tgaccatcca gtttatagag gggtgtactg tcagcggtga gacagaggcc     720
aacactccag gtctgaacaa gctgacgctg actggctgga aggagtgcag cttcaatact     780
ttgacagggc ctgctgatat caaagacgga aaaatttatg aggggctttg ggaaacaaag     840
```

```
atgcgcgatt tgccaatcg taacgccagt gtcaccgctt atctgaccat gaagccggga    900
aacagcaatg ccagaaaga tacgctgatg atcggcattc tgaaatcac cggcctgacg    960 ccgttcgtgt tggaagtgca gccgctc                                      987
```

<210> SEQ ID NO 23
<211> LENGTH: 14
<212> TYPE: PRT
<213> ORGANISM: Artificial Sequence
<220> FEATURE:
<223> OTHER INFORMATION: SCR1/SCR3 sequences from mouse lipocalin

<400> SEQUENCE: 23

```
Gln Phe Arg Gly Arg Trp Tyr Val Thr Leu Tyr Gly Arg Thr
1               5                   10
```

<210> SEQ ID NO 24
<211> LENGTH: 14
<212> TYPE: PRT
<213> ORGANISM: Artificial Sequence
<220> FEATURE:
<223> OTHER INFORMATION: SCR1/SCR3 amino acid sequences from mouse MUP

<400> SEQUENCE: 24

```
Lys Ile Asn Gly Glu Trp His Thr Gly Leu Tyr Gly Arg Glu
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: SCR1/SCR3 amino acid sequences from bovine
      BosD2

<400> SEQUENCE: 25

```
Lys Ile Pro Gly Glu Trp Arg Ile Glu Gly Leu Ala Lys Gly
1               5                   10
```

<210> SEQ ID NO 26
<211> LENGTH: 16
<212> TYPE: PRT
<213> ORGANISM: Artificial Sequence
<220> FEATURE:
<223> OTHER INFORMATION: SCR1/SCR3 amino acid sequences from insect
      nitrophorin

<400> SEQUENCE: 26

```
Lys Tyr Phe Asn Gly Asp Val Trp Tyr Val Ala Val Leu Asn Arg Asn
1               5                   10                  15
```

<210> SEQ ID NO 27
<211> LENGTH: 14
<212> TYPE: PRT
<213> ORGANISM: Artificial Sequence
<220> FEATURE:
<223> OTHER INFORMATION: SCR1/SCR3 amino acid sequences form AimA

<400> SEQUENCE: 27

```
Val Thr Thr Ala Ser Trp Ser Ala Ala Leu Ala Arg Ala
1               5                   10
```

<210> SEQ ID NO 28
<211> LENGTH: 14
<212> TYPE: PRT
<213> ORGANISM: Artificial Sequence

```
<220> FEATURE:
<223> OTHER INFORMATION: SCR1/SCR3 amino acid sequences from insect
      bilin binding protein

<400> SEQUENCE: 28

Asn Tyr His Gly Lys Trp Trp Glu Trp Val Leu Ser Arg Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: SCR1/SCR3 amino acid sequences from E. coli
      lipocalin

<400> SEQUENCE: 29

Arg Tyr Leu Gly Thr Trp Tyr Glu Trp Ile Leu Ser Arg Thr
1               5                   10

<210> SEQ ID NO 30
<211> LENGTH: 6
<212> TYPE: PRT
<213> ORGANISM: Artificial Sequence
<220> FEATURE:
<223> OTHER INFORMATION: SCR1/SCR3 motif amino acids

<400> SEQUENCE: 30

His Gly Pro Trp His Arg
1               5
```

ANTI-INFLAMMATORY COMPOUNDS AND METHODS OF USE

CROSS REFERENCE TO RELATED APPLICATIONS

This application is a divisional of U.S. application Ser. No. 16/943,763, filed Jul. 30, 2020, which is a divisional of U.S. application Ser. No. 15/883,999, filed Jan. 30, 2018, issued Aug. 25, 2020, as U.S. Pat. No. 10,752,662, issued Aug. 25, 2020, which is a continuation-in-part of U.S. application Ser. No. 15/311,667, filed Nov. 16, 2016, now abandoned, which is the § 371 U.S. National Stage of International Application No. PCT/US2015/031052, filed May 15, 2015, which was published in English under PCT Article 21(2), which in turn claims the benefit of U.S. Provisional Application No. 61/994,601, filed May 16, 2014, all of which are incorporated herein by reference in their entirety.

ACKNOWLEDGMENT OF GOVERNMENT SUPPORT

This invention was made with government support under grants R01 GM095385, P50GM098911-01A1, 1F32DK098884-01A1, P01 HD022486, and R01CA176579, awarded by the National Institutes of Health. The government has certain rights in the invention.

FIELD

This disclosure relates to anti-inflammatory proteins from gut microbiota and methods of their use.

BACKGROUND

Inflammatory disorders such as allergies, asthma, rheumatoid arthritis, inflammatory bowel disease, and atherosclerosis affect large numbers of people. While anti-inflammatory drugs are available, many have serious side effects, including increased risk of stroke or gastric damage or are systemic suppressors of the immune system. Thus, there remains a need for additional anti-inflammatory therapies.

SUMMARY

The inventors have identified a protein from *Aeromonas* with anti-inflammatory activity (referred to herein in some examples as anti-inflammatory protein (AP), protein 1882, or AimA, for example, SEQ ID NO: 1). Disclosed herein are methods of treating or inhibiting (for example, reducing) inflammation in a subject by administering the newly identified anti-inflammatory protein to a subject. In some embodiments, the protein has at least 80% sequence identity to the amino acid sequence set forth as SEQ ID NO: 1 or fragments thereof. In some examples, the subject has an inflammatory disease, such as inflammatory bowel disease, rheumatoid arthritis, osteoarthritis, inflammatory lung disease, atherosclerosis, systemic lupus erythematosus, Sjogren's syndrome, asthma, allergic rhinitis, psoriasis, irritable bowel syndrome, necrotizing enterocolitis, or atopy. In other embodiments, the protein (such as a polypeptide with at least 80% sequence identity to SEQ ID NO: 1 is used in methods of treating or inhibiting sepsis or septic shock in a subject.

Also disclosed herein are methods of identifying anti-inflammatory compounds by determining the effect of test compounds on one or more markers of inflammation (for example, neutrophil accumulation in zebrafish gut). In some embodiments, germ-free zebrafish or zebrafish inoculated with a single defined bacterial strain (or a defined combination of strains) are contacted with one or more test compounds and the number of neutrophils in the gut of the zebrafish are measured and compared to a control. In one specific example, the zebrafish is a transgenic zebrafish expressing a fluorescent protein (e.g., green fluorescent protein (GFP)) or another marker under the control of the neutrophil-specific myeloperoxidase (MPO) promoter. This system permits measurement of neutrophil accumulation in the gut of living organisms.

Recombinant vectors including a nucleic acid encoding the herein identified anti-inflammatory protein (such as a nucleic acid encoding a protein with at least 80% sequence identity to SEQ ID NO: 1 or a fragment thereof) operably linked to a heterologous promoter are also disclosed. In some examples, the nucleic acid encoding the protein is set forth in SEQ ID NO: 2. Cells including the recombinant vector (for example, cells transformed with the vector) are also disclosed.

Also disclosed herein are isolated polypeptides with at least 80% sequence identity (such as at least 85%, 90%, 95%, or even 100% identity) to the amino acid sequence of SEQ ID NO: 11, an amino acid sequence 130-190 amino acids in length with at least 80% sequence identity (such as at least 85%, 90%, 95%, or even 100% identity) to amino acids 1-188 of SEQ ID NO: 11, amino acids 21-188 of SEQ ID NO: 11, or amino acids 189-330 of SEQ ID NO: 11, or an amino acid sequence 120-180 amino acids in length with at least 80% sequence identity (such as at least 85%, 90%, 95%, or even 100% identity) to amino acids 1-185 of SEQ ID NO: 1, amino acids 23-185 of SEQ ID NO: 1, or amino acids 192-313 of SEQ ID NO: 1. The polypeptides may be used in treating or inhibiting inflammation or sepsis or septic shock in a subject.

Also disclosed are isolated nucleic acids with at least 80% sequence identity (such as at least 85%, 90%, 95%, or even 100% identity) to the nucleic acid sequence of SEQ ID NO: 17, a nucleic acid 360-540 nucleotides in length and having at least 80% sequence identity (such as at least 85%, 90%, 95%, or even 100% identity) to nucleotides 1-564 of SEQ ID NO: 17, nucleotides 61-564 of SEQ ID NO: 17, or nucleotides 565-990 of SEQ ID NO: 17, or a nucleic acid 360-540 nucleotides in length with at least 80% sequence identity (such as at least 85%, 90%, 95%, or even 100% identity) to nucleotides 1-555 of SEQ ID NO: 2, nucleotides 67-555 of SEQ ID NO: 2, or nucleotides 574-939 of SEQ ID NO: 2. In some embodiments, the nucleic acids are operably linked to a promoter, for example, in a recombinant vector. Also disclosed are cells comprising the recombinant vector or transformed cells including one or more of the nucleic acids operably linked to a promoter.

The foregoing and other features of the disclosure will become more apparent from the following detailed description, which proceeds with reference to the accompanying figures.

*Aeromonas veronii* (Leech AMA). A and B indicate groups that are significantly different from one another (ANOVA, $p<0.05$).

Figure 1:
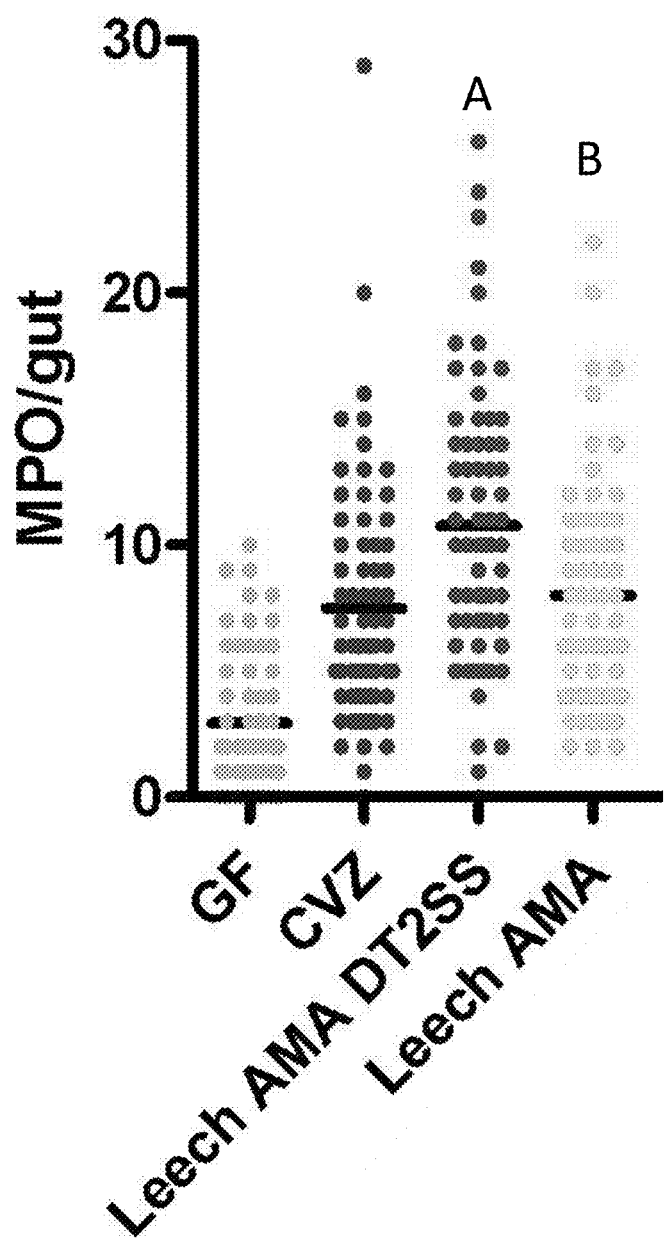
FIG. 1 is a graph showing the number of myeloperoxidase (MPO) positive cells in the gut of zebrafish raised germ-free (GF), conventionally (CVZ), mono-associated with type II secretion system (T2SS) deletion mutant *A. veronii* (Leech AMA DT2SS), and mono-associated with wild-type (WT)
Figure 2:
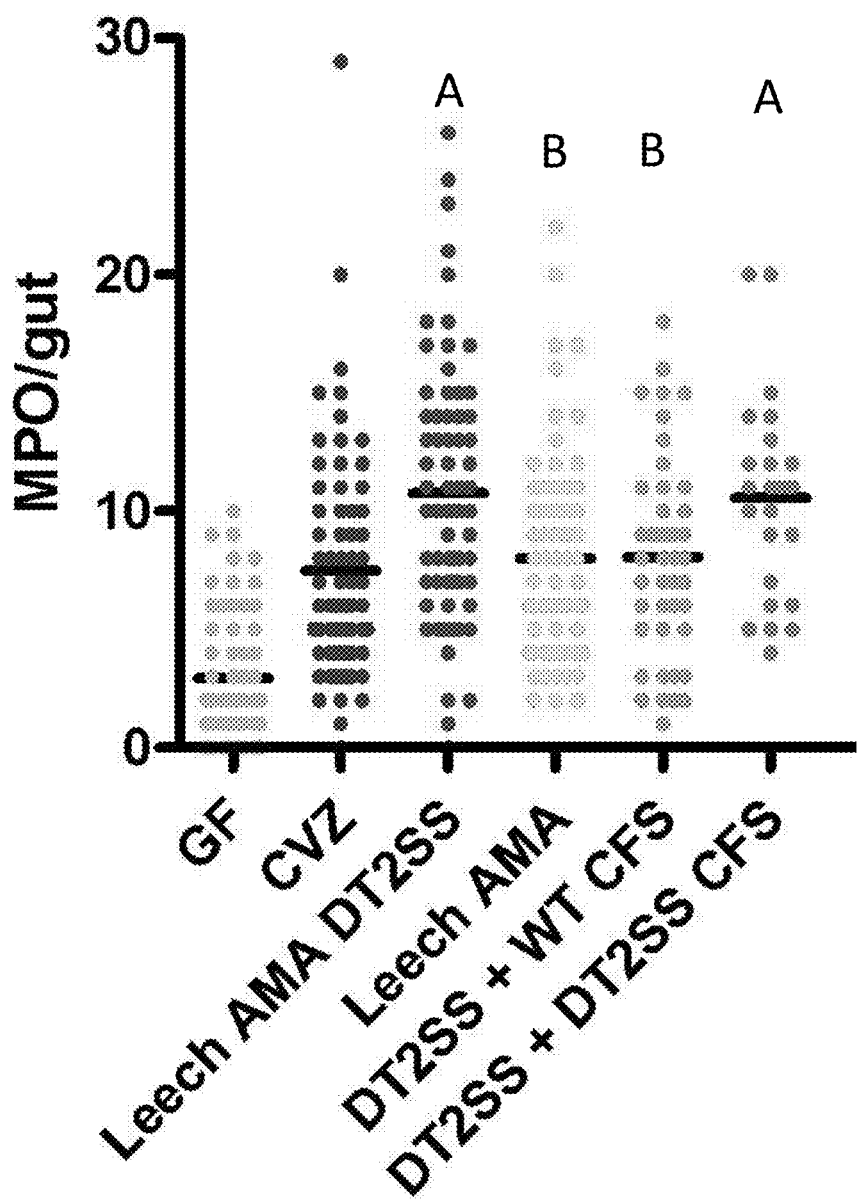

FIG. 2 is a graph showing the number of MPO positive cells in the gut of zebrafish raised GF, CVZ, mono-associated with DT2SS *A. veronii* (Leech AMA DT2SS), mono-associated with WT *A. veronii* (Leech AMA), or mono-associated with DT2SS *A. veronii* and cell-free supernatant (CFS) from WT *A. veronii* (DT2SS+WT CFS) or from DT2SS *A. veronii* (DT2SS+DT2SS CFS). A and B indicate groups that are significantly different from one another (ANOVA, $p<0.05$). The first four lanes repeat data shown in FIG. 1, for the sake of comparison.

Figure 3:
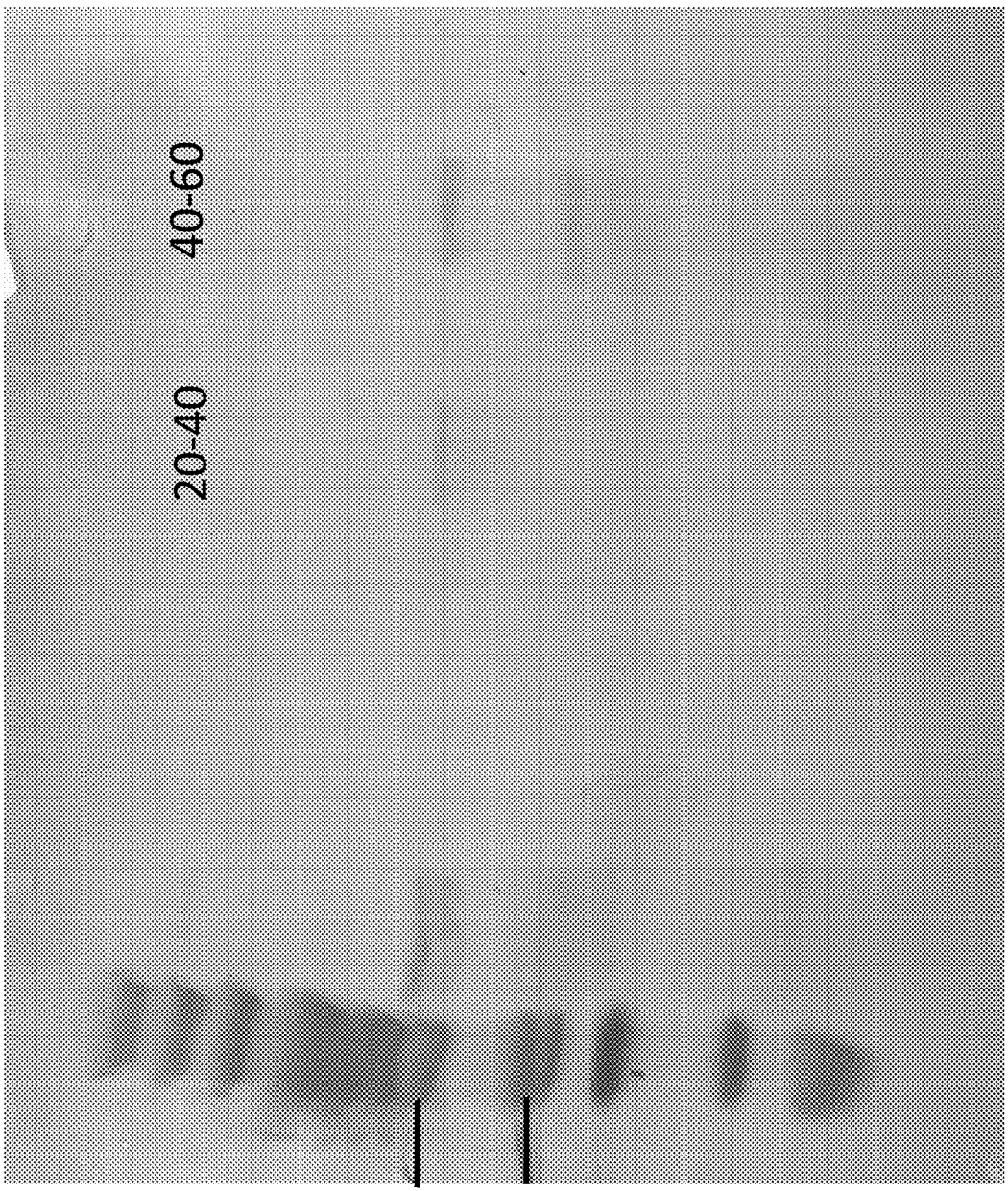

FIG. 3 is a digital image of Coomassie-blue stained SDS-PAGE of *A. veronii* CFS fractions. Lane 1: ladder; lane 2: concentrated CFS; lane 3: empty; lane 4: 0-20% ammonium sulfate fraction; lane 5: empty; lane 6: 20-40% ammonium sulfate fraction; lane 7: empty; lane 8: 40-60% ammonium sulfate fraction.

Figure 4:
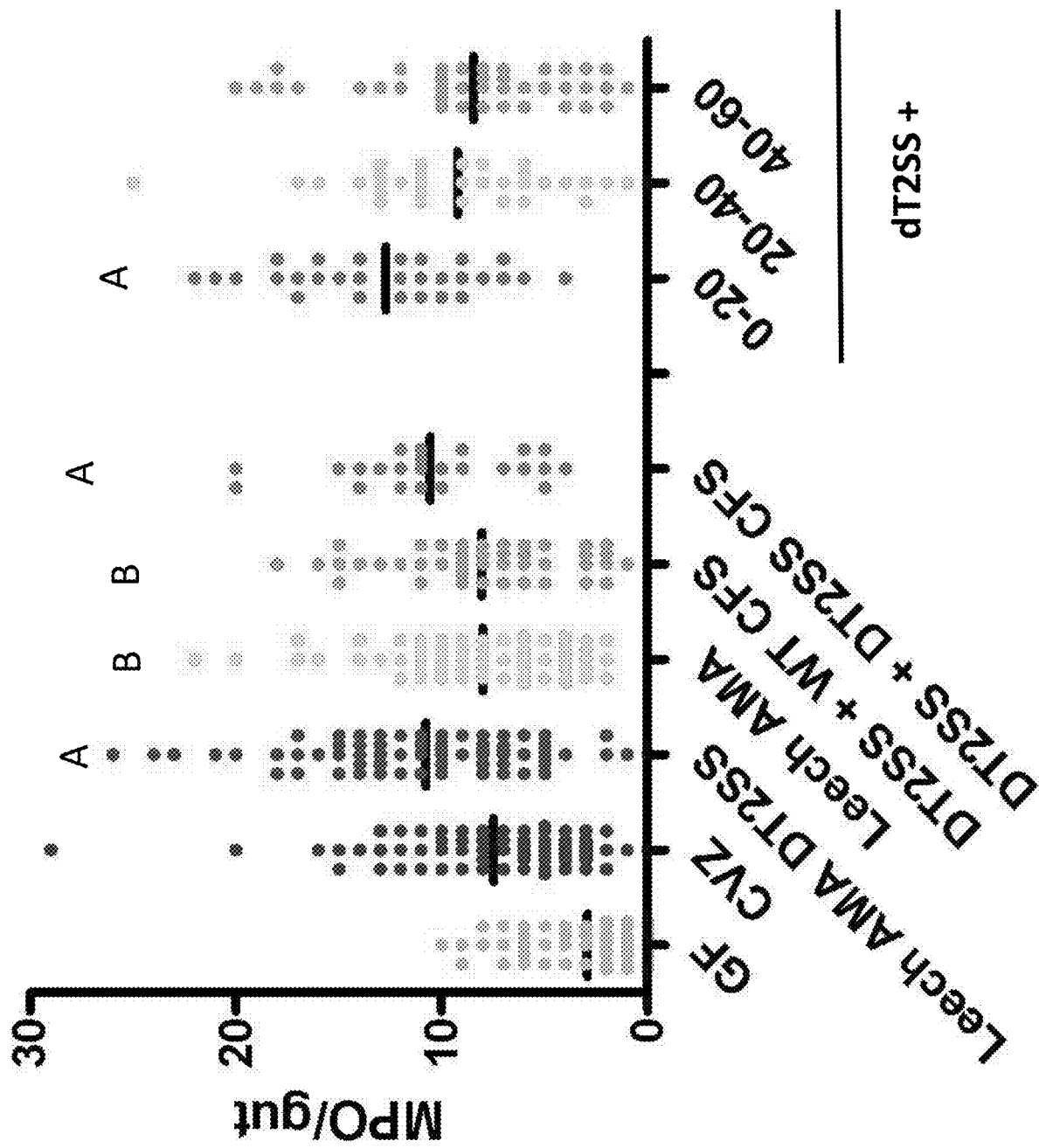

FIG. 4 is a graph showing the number of MPO positive cells in the gut of zebrafish raised GF, CVZ, mono-associated with DT2SS *A. veronii* (Leech AMA DT2SS), mono-associated with WT *A. veronii* (Leech AMA), mono-associated with DT2SS *A. veronii* and CFS from WT *A. veronii* (DT2SS+WT CFS), mono-associated with DT2SS *A. veronii* and CFS from DT2SS *A. veronii* (DT2SS+DT2SS CFS), mono-associated with DT2SS *A. veronii* plus 0-20% ammonium sulfate fraction, (0-20), mono-associated with DT2SS *A. veronii* plus 20-40% ammonium sulfate fraction (20-40), or mono-associated with DT2SS *A. veronii* plus 40-60% ammonium sulfate fraction (40-60). A and B indicate groups that are significantly different (ANOVA, $p<0.05$). The first six lanes repeat data shown in FIG. 2, for the sake of comparison.

Figure 5A:
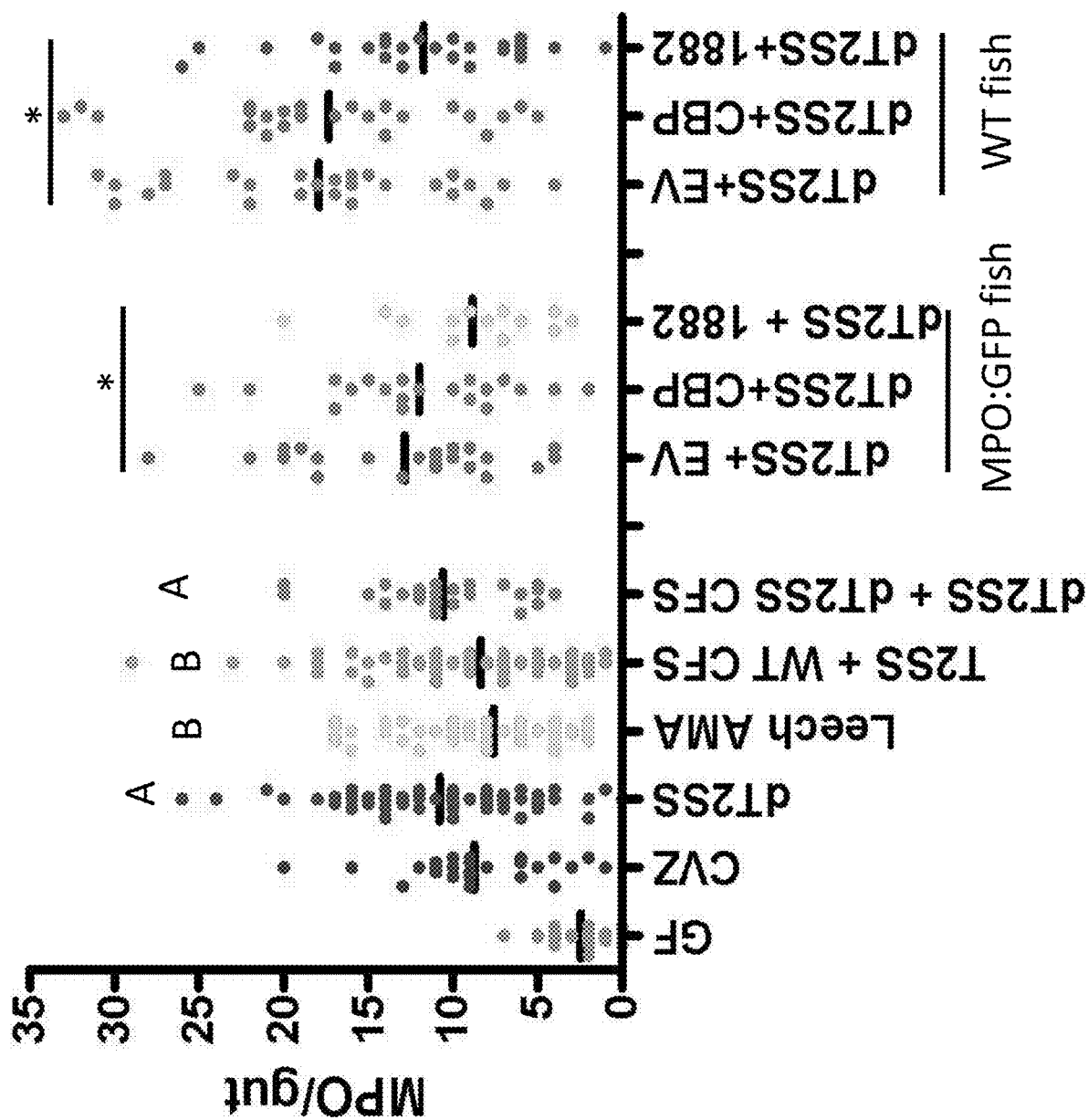

FIG. 5A is a graph showing the number of MPO positive cells in the gut of zebrafish raised GF, CVZ, mono-associated with DT2SS *A. veronii* (Leech AMA DT2SS), mono-associated with WT *A. veronii* (Leech AMA), mono-associated with DT2SS *A. veronii* plus CFS from WT *A. veronii* (DT2SS+WT CFS), or mono-associated with DT2SS *A. veronii* plus CFS from DT2SS *A. veronii* (DT2SS+DT2SS CFS). The graph also shows zebrafish transgenic for MPO:GFP or WT fish mono-associated with DT2SS *A. veronii* plus CFS from *E. coli* carrying a control plasmid (DT2SS+EV), mono-associated with DT2SS *A. veronii* plus CFS from *E. coli* carrying a plasmid for chitin binding protein (dT2SS+CBP), or mono-associated with DT2SS *A. veronii* plus CFS from *E. coli* carrying a plasmid with the gene for AP (dT2SS+1882). A and B indicate groups that are significantly different (ANOVA, $p<0.05$). * indicates significantly different between +EV condition and +AP (1882) condition.

Figure 5B:
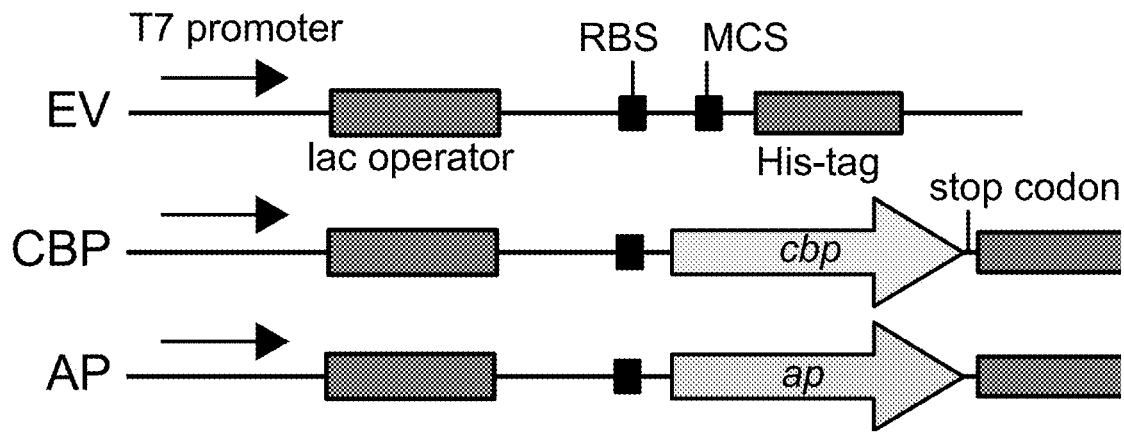

FIG. 5B is a diagram showing the *E. coli* expression vectors for AP and CBP proteins. Expression is induced with IPTG. RBS, ribosome binding site; MCS, multiple cloning site; EV, empty vector.

Figure 6:
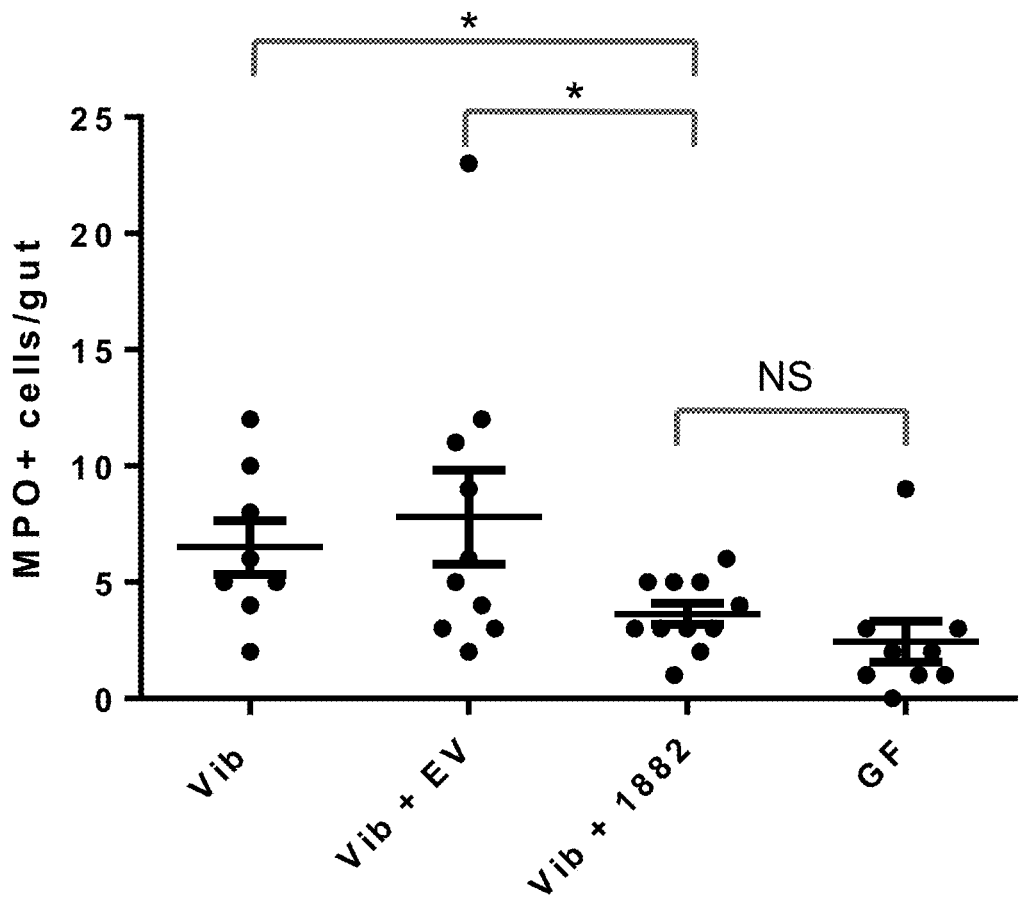

FIG. 6 is a graph showing the number of MPO positive cells in the gut of zebrafish infected with *Vibrio* (Vib: 48 hours of *Vibrio* infection), zebrafish infected with *Vibrio* treated with CFS from *E. coli* carrying a control plasmid (Vib+EV), zebrafish infected with *Vibrio* treated with CFS from *E. coli* carrying a plasmid with the gene for AP under an inducible promoter (Vib+1882), or GF. *: $p<0.05$; NS: not significant.

Figure 7A:
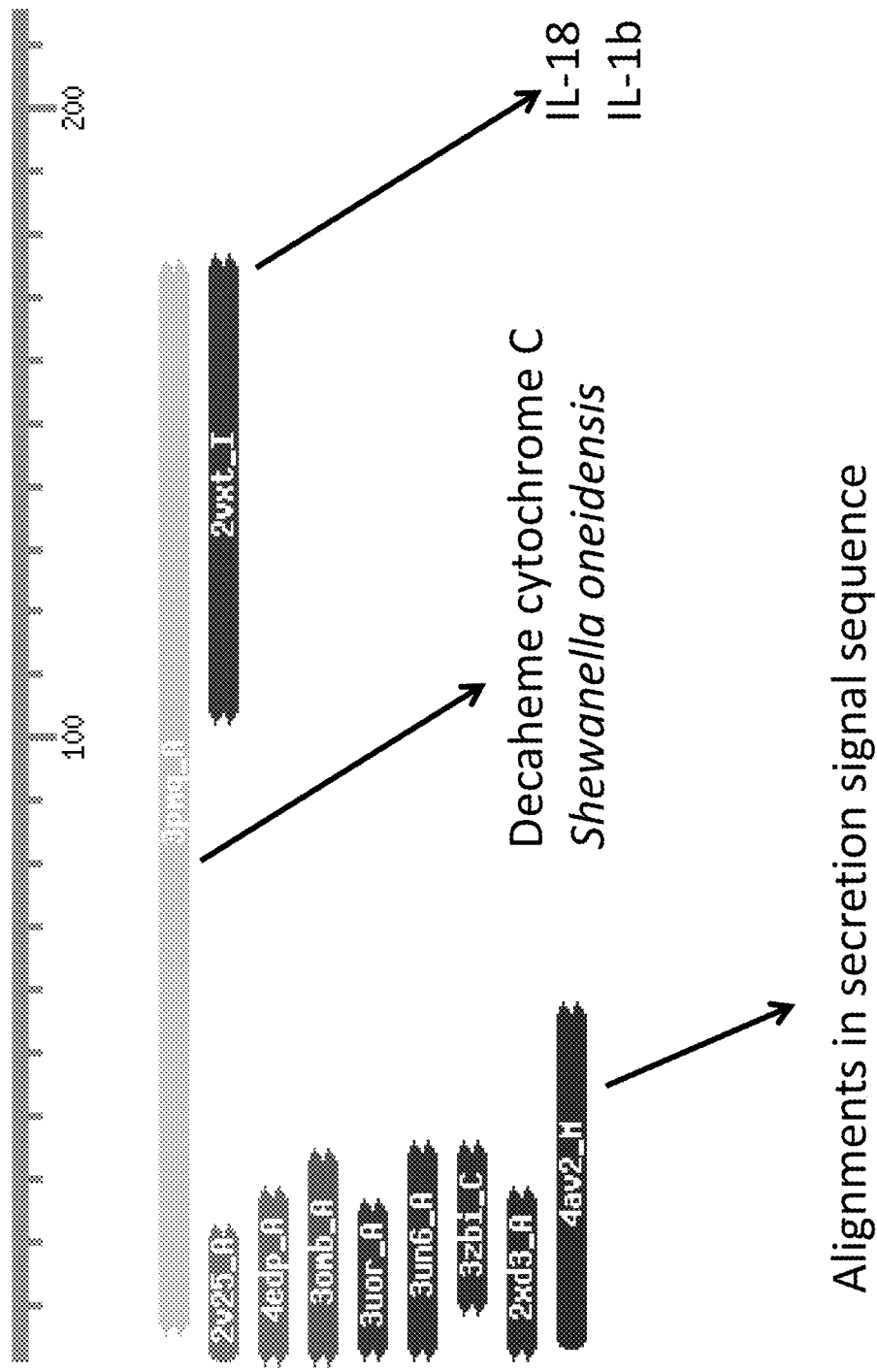

FIG. 7A is a schematic showing *A. veronii* AP (hatched line) and conserved structural domains compared to known proteins. The N-terminal region of *A. veronii* AP shows similarity to secretion signal sequences from other proteins. The main conserved domain (3pnq_A) has similarity to decaheme cytochrome C from *Shewanella oneidensis*. The protein also includes a beta-trefoil domain (2vxt_I) that is also found in the cytokine superfamily (such as IL-18 and IL-1b).

Figure 7B:
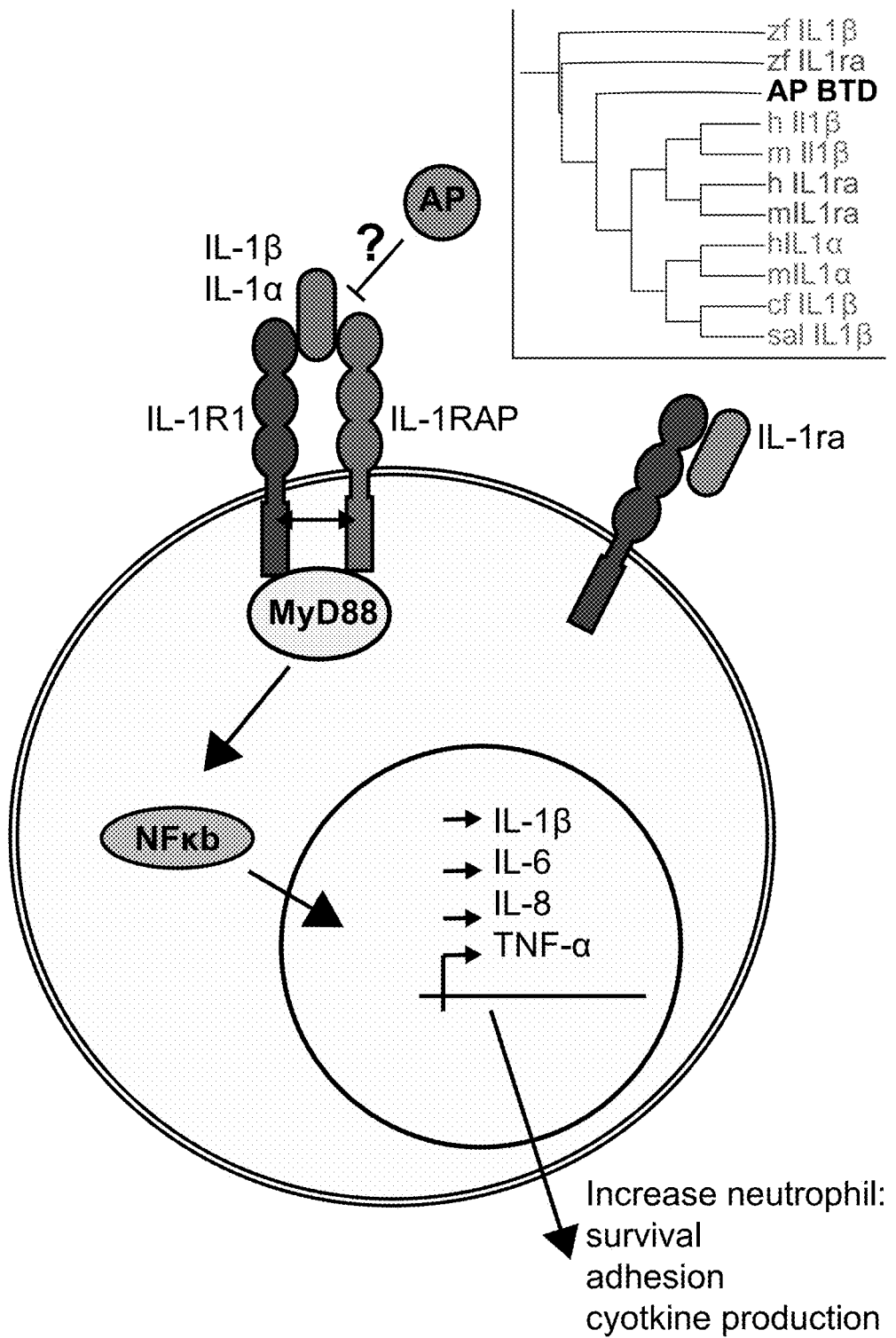

FIG. 7B is a diagram illustrating interleukin-1 (IL-1) signaling pathway and a proposed role for AP in blocking IL-1R1 signaling. The inset shows phylogenetic relationship of the AP β-trefoil domain (BTD) to the same domain from the indicated human (h), mouse (m), zebrafish (z), salmon (sal), and catfish (cf) proteins. The sequences used in constructing the phylogenetic tree are as follows (GenBank Accession Nos.): zfIL1β, NP_998009.2; zfIL1ra, AEJ36293.1; hIL1β, NP_000567.1; mIL1β, AAH11437.1; hIL1ra, AAH09745.1; mIL1ra, AAA39278.1; hIL1α, CAG33695.1; mIL1α, AAH03727.1; cfIL1β, NP_001187149; and salIL1β, NP_0011178191. AP BTD used in generating the phylogenetic tree was amino acids 148-176 of SEQ ID NO: 1.

Figure 8:
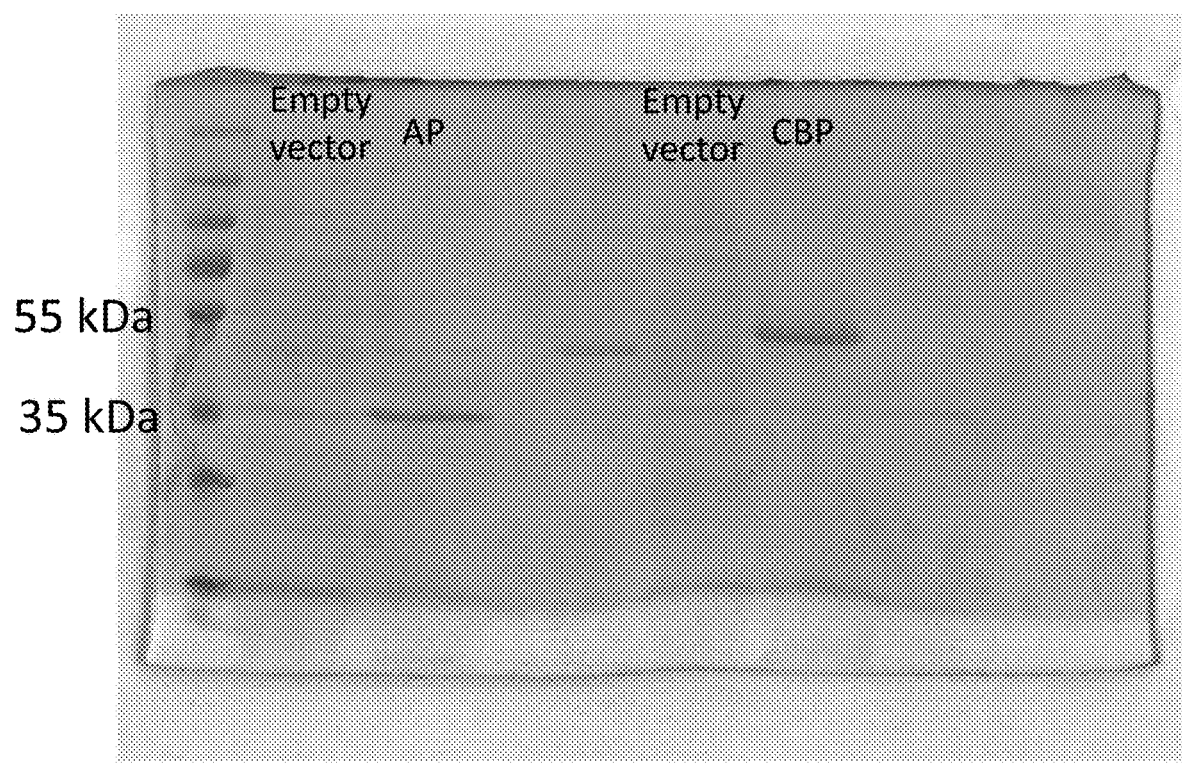

FIG. 8 is a digital image of a Coomassie-blue stained gel showing supernatant from cultures of *E. coli* carrying a control plasmid (empty vector) or a plasmid with the AP gene (AP) or the chitin binding protein gene (CBP).

Figure 9A:
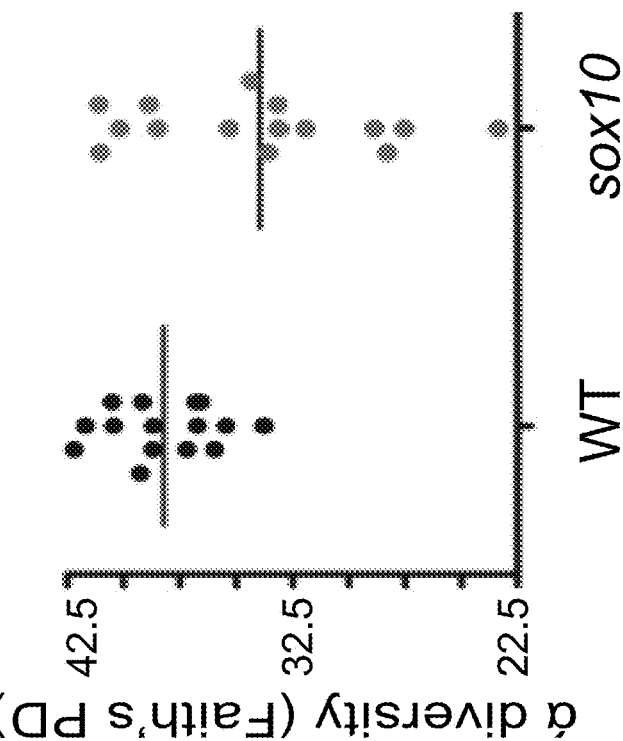
Figure 9B:
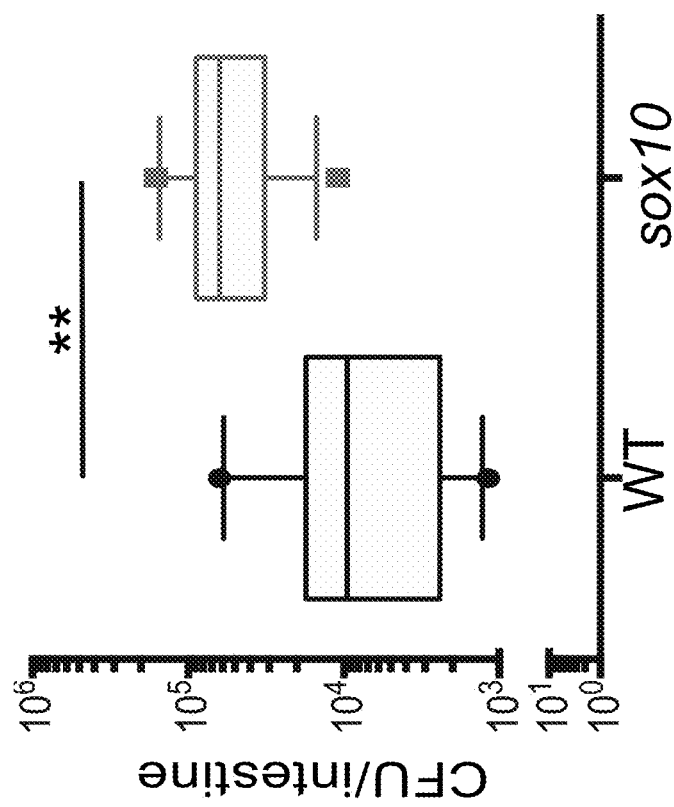

FIGS. 9A-9D are a series of graphs showing sox10 zebrafish characteristics and the effect of inoculating germ-free fish with microbiota from sox10 fish. FIG. 9A is a graph showing bacterial load in WT and sox10 fish. FIG. 9B is a graph showing diversity of the bacterial communities in WT and sox10 fish. FIG. 9C is a graph showing neutrophil influx to the intestine in WT and sox10 fish. FIG. 9D is a graph showing neutrophil influx to the intestine in WT GF zebrafish inoculated with either microbiota from a WT or a sox10 donor fish. $p<0.01$, *$p<0.001$, T test.

Figure 10:
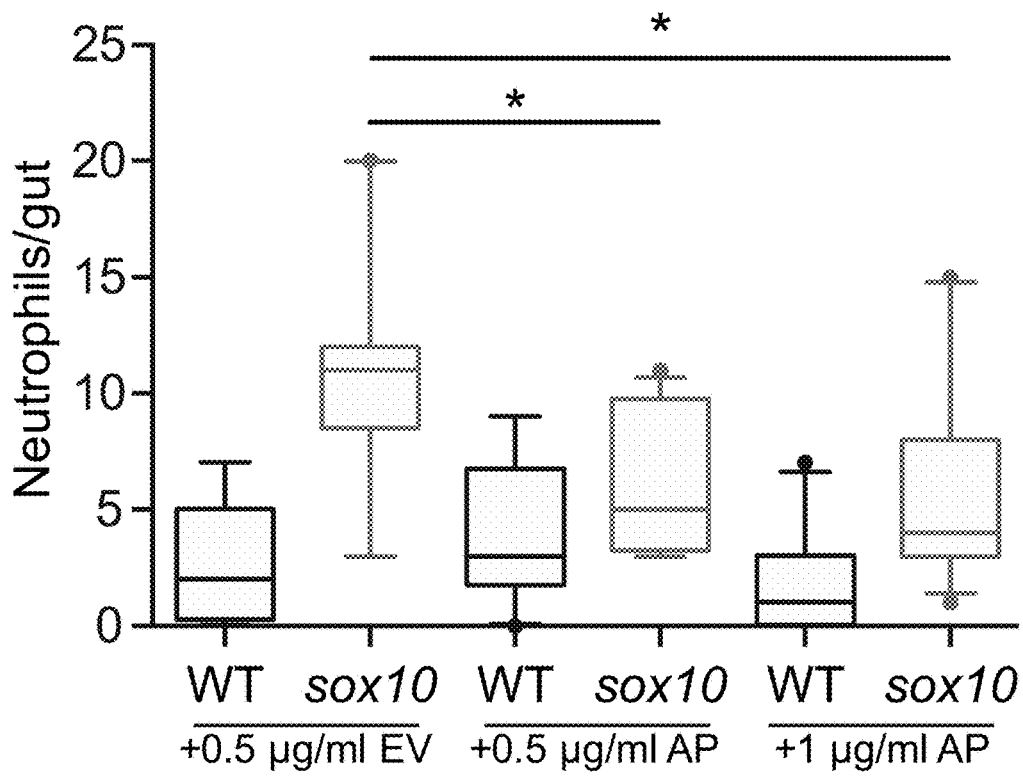

FIG. 10 is a graph showing neutrophil influx in WT or sox10 zebrafish treated with empty vector (EV), 0.5 μg/ml CFS from *E. coli* expressing AP protein, or 1 μg/ml CFS from *E. coli* expressing AP protein. *$p<0.05$.

Figure 11:
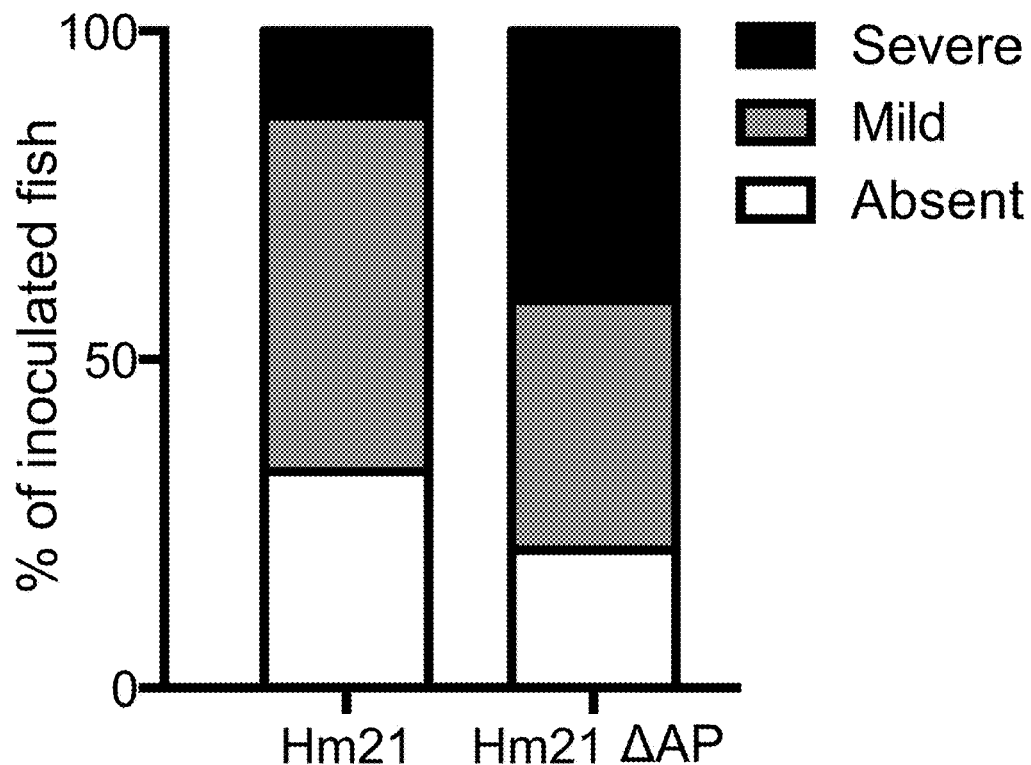

FIG. 11 is a graph showing the effect of infection of WT zebrafish with *A. veronii* Hm21 or Hm21 ΔAP on inflammation (neutrophil influx in the intestine). The graph shows percent of inoculated fish with severe (black), mild (gray), or no (white) inflammation.

Figure 12:
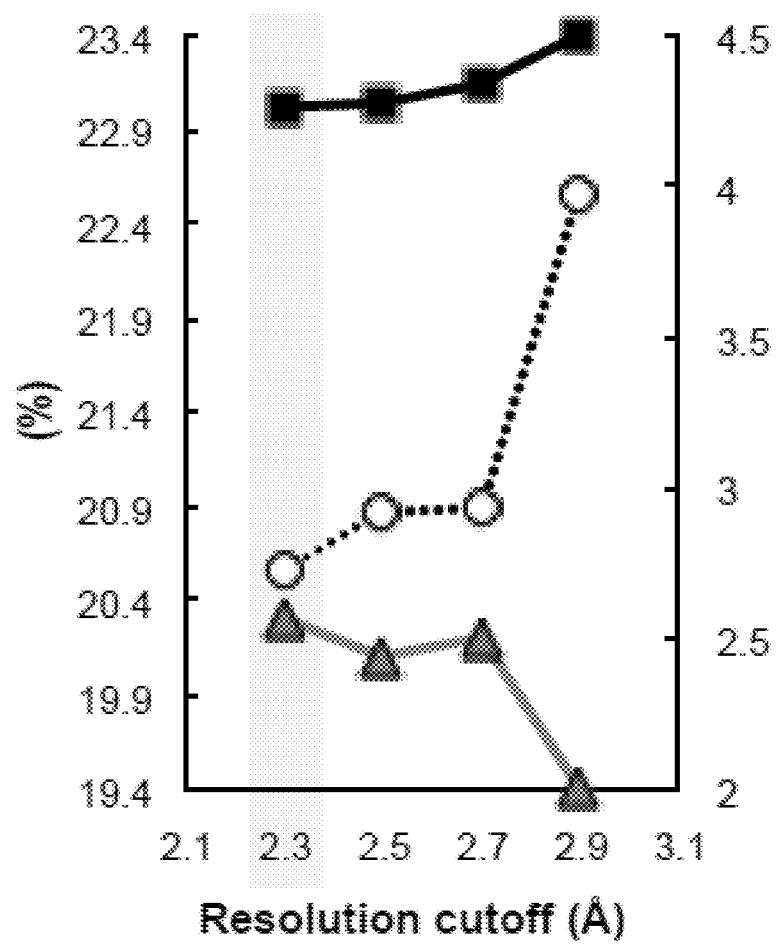

FIG. 12 is a graph showing $R_{free}$ (black line, solid squares), $R_{work}$ (gray line, solid triangles), and $R_{free}-R_{work}$ (dotted line, open circles) calculated at 2.9 Å for paired refinements in which the model was first refined against either 2.9, 2.7, 2.5, or 2.3 Å data. The chosen resolution cutoff of 2.3 Å (shaded) shows a decrease in Rf, and increase in $R_{work}$, which indicates that using the extra resolution improves the model.

FIGS. 13A and 13B show the 2.6 Å structure of AimA displays two calycin domains (FIG. 13A) and the amino terminal domain of AimA is connected by a short linker to the carboxy terminal domain and that both domains contain an eight-stranded full (C-term) or partial (N-term) β-barrel (FIG. 13B).

Figure 14A:
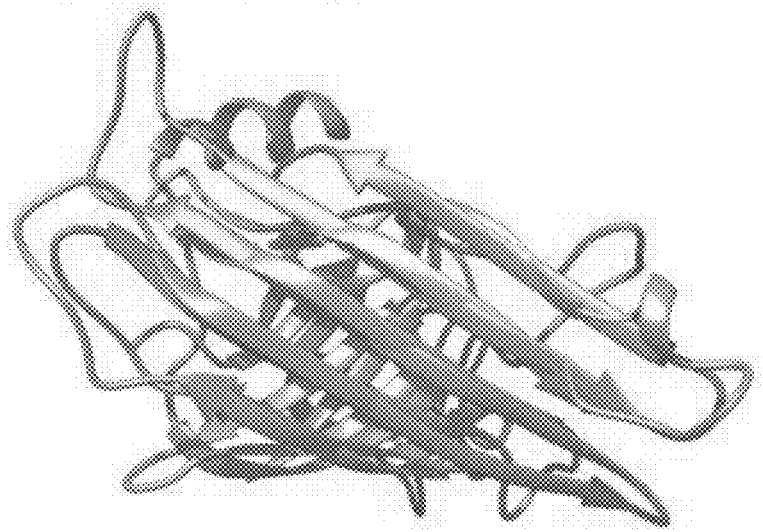
Figure 14B:
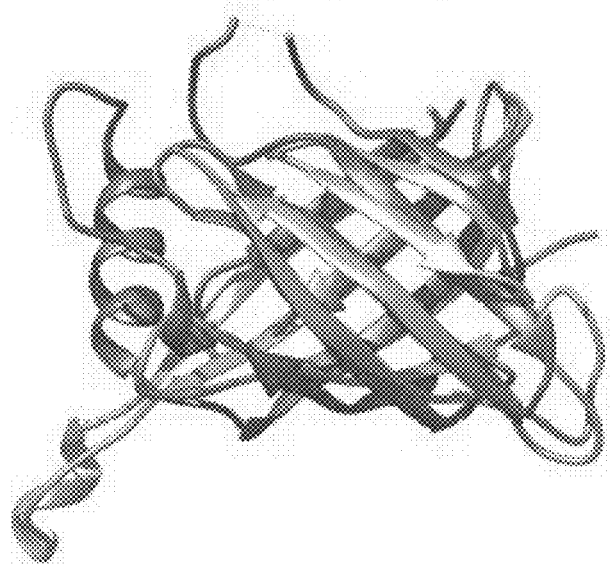
Figure 14C:
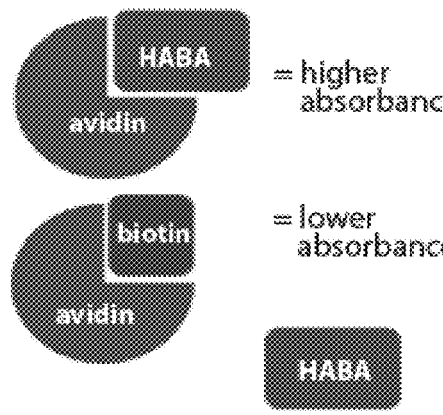
Figure 14D:
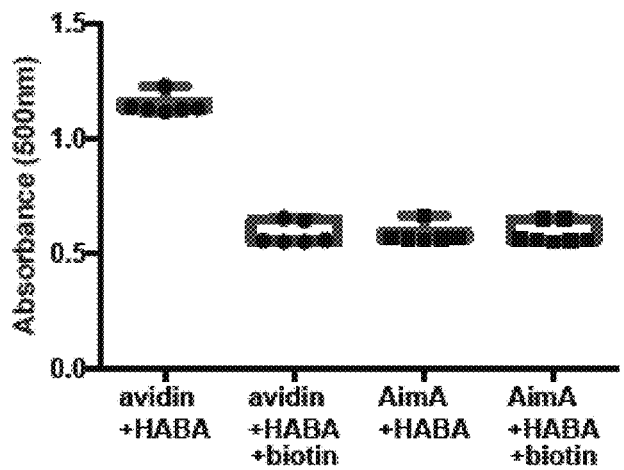

FIGS. 14A-14D are a series of panels showing Structural homology of the two domains of AimA to avidins. FIG. 14A is a structural overlay of N-term domain of AimA with top structural homology hit from PDBeFold search, *Streptomyces avindinii* streptavidin (1swg). FIG. 14B is a structural overlay of C-term domain of AimA with top structural homology hit from PDBeFold search, *Danio rerio* zebavidin (4bj8). FIG. 14C is a schematic of the biotin binding colorimetric assay. Biotin has higher affinity for avidins than HABA does, so it replaces HABA in the binding site, thereby decreasing the absorbance at 500 nm. FIG. 14D is a graph showing results from the biotin binding colorimetric assay. Biotin replaces HABA binding in avidin, corresponding to a decrease in absorbance when biotin is present. With AimA, there is no difference in absorbance with or without biotin, indicating no biotin binding.

Figure 15A:
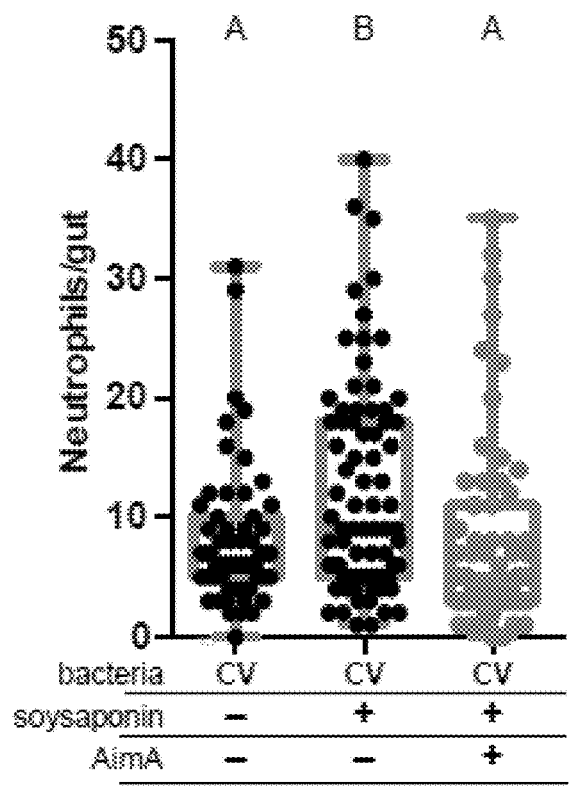
Figure 15B:
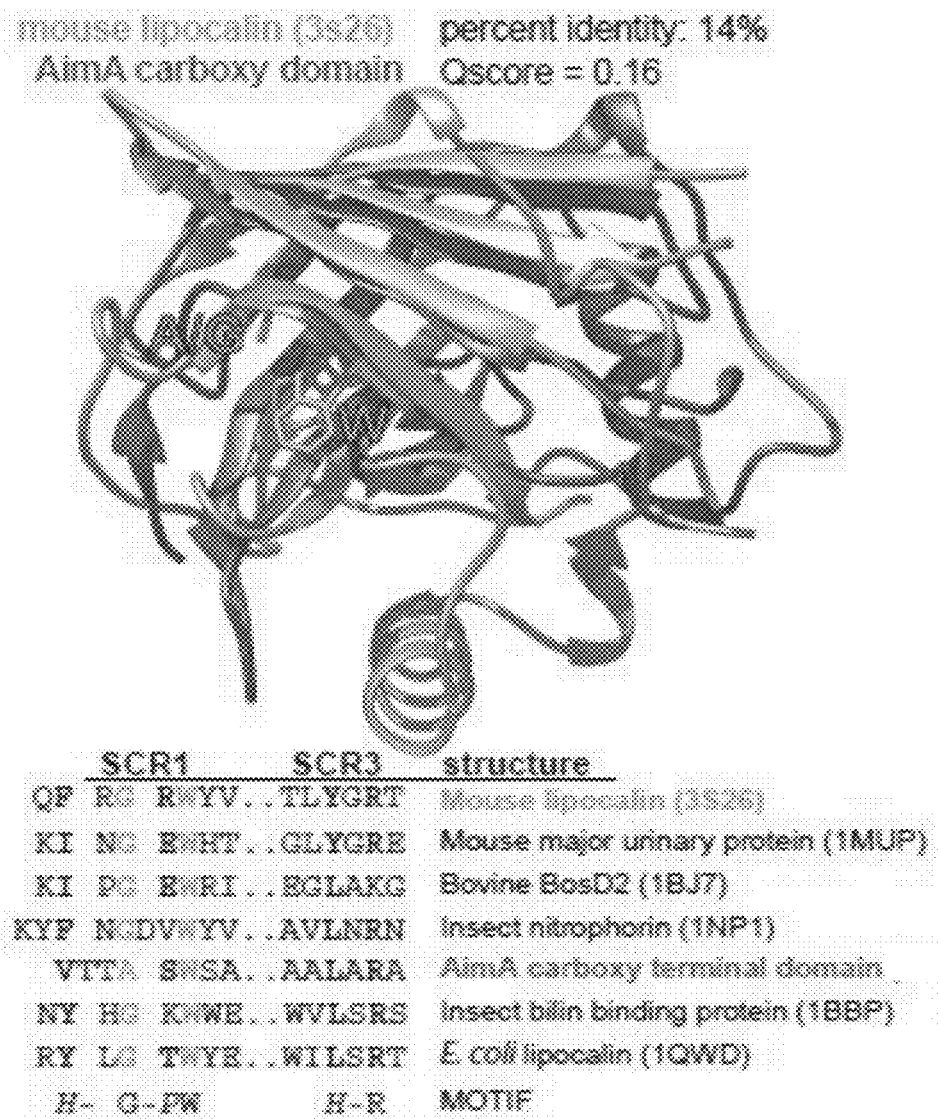
Figure 15C:
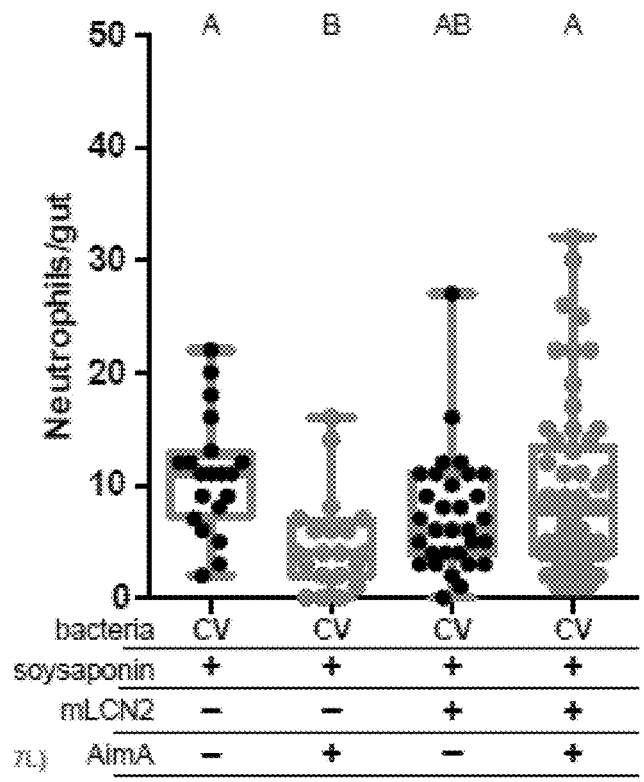

FIGS. 15A-15C are a series of panels showing the effect of AimA on intestinal inflammation in zebrafish. FIG. 15A is a graph showing that feeding zebrafish soy saponin induced increased intestinal neutrophil response, and treating those fish with 100 ng/ml purified AimA prevented the increased intestinal neutrophil response. Letters indicate significantly different groups; ANOVA with multiple comparisons. Each dot represents one fish; data collected from at least two independent experiments; n≥24. FIG. 15B is a schematic showing a structural overlay of mouse lipocalin (PDB ID 3s26) and AimA C-term domain using PDBeFold. The β-strands are labeled according to canonical lipocalin nomenclature. Qscore is a structural overlay quality score that takes into account both the root mean standard deviation (RMSD) of the $C_\alpha$ carbons and the alignment length. Qscore of 1 is perfect alignment, 0 is no alignment. The residues highlighted in orange are conserved in both the sequences and the structures. Displayed are the sequences of Structurally Conserved Regions (SCR) 1 and 3 of a representative set of kernel and outlier lipocalins (PDB accession numbers are shown in parentheses). The C-term domain of AimA is included and contains a subset of conserved SCR residues. Mouse lipocalin, SEQ ID NO: 23; mouse major urinary protein, SEQ ID NO: 24; bovine BosD2, SEQ ID NO: 25; insect nitrophorin, SEQ ID NO: 26; AimA carboxy terminal domain, SEQ ID NO: 27; insect bilin binding protein, SEQ ID NO: 28; E. coli lipocalin, SEQ ID NO: 29; Motif, SEQ ID NO: 30. Bold residues are conserved across the sequences. FIG. 15C is a graph showing treatment of conventionally raised (CV) fish with soysaponin and lipocalin prevented AimA from reducing the neutrophil response. Each dot represents one fish; n 20 from at least three independent experiments. Letters indicate significantly different groups; ANOVA with multiple comparisons.

Figure 16A:
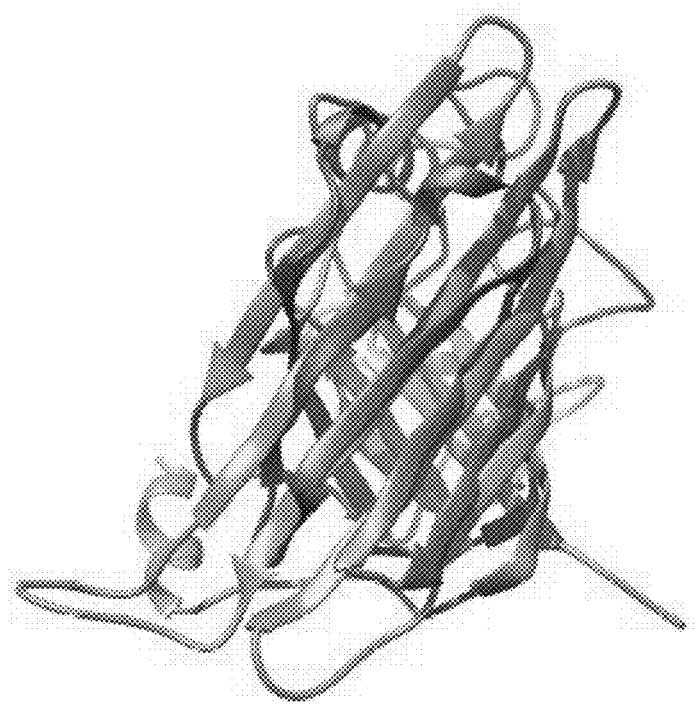
Figure 16B:
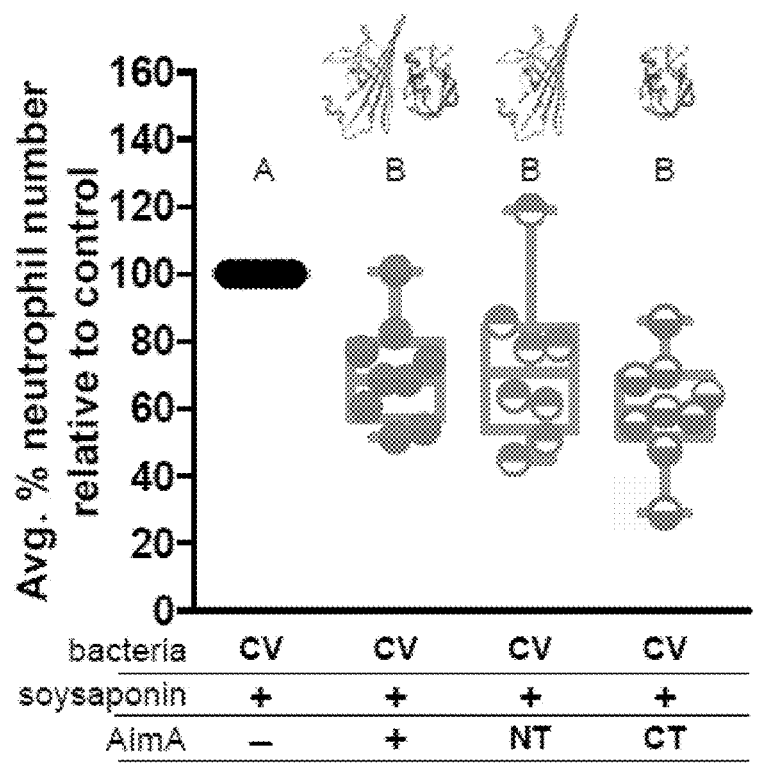
Figure 16C:
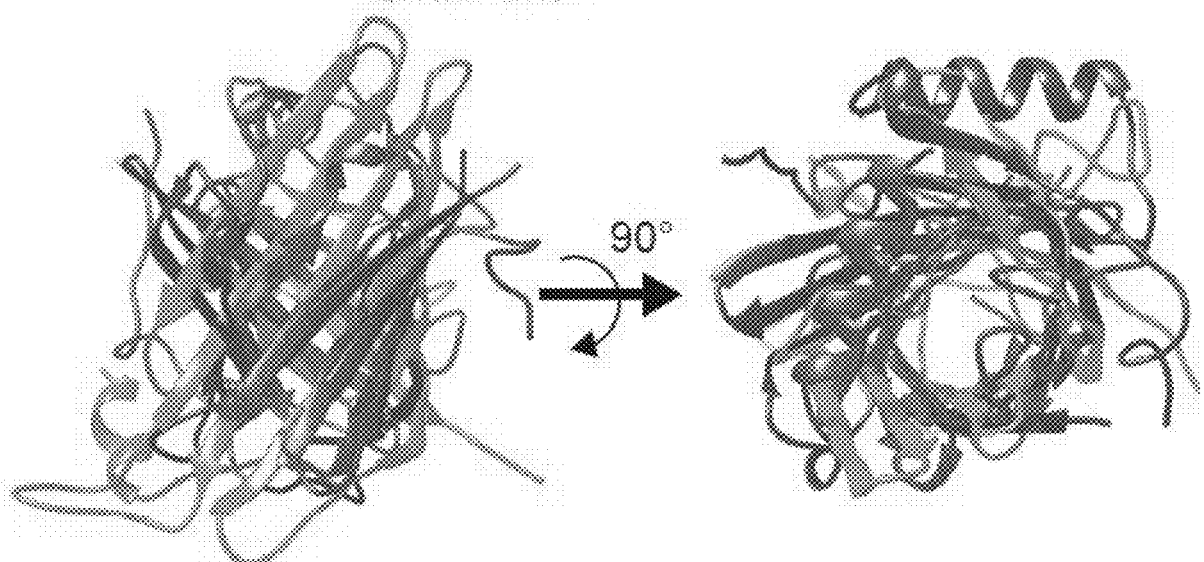

FIGS. 16A-16C are a series of panels showing function of AimA domains. FIG. 16A is a schematic showing an overlay of C-term and N-term domains of AimA using PDBeFold. FIG. 16B is a graph showing neutrophils in conventionally raised (CV) fish fed soysaponin (SS) and treated with either purified full-length AimA or purified N-term (NT) or C-term (CT). Each dot represents the average percent of neutrophil influx in a flask of 15 fish from the average neutrophil influx of a control flask (soysaponin only) of 15 fish. n≥9 flasks from at least three independent experiments. Letters indicate significantly different groups; ANOVA with multiple comparisons. FIG. 16C shows an overlay of C- and N-term domains of AimA and mLCN using PDBeFold.

Figure 17A:
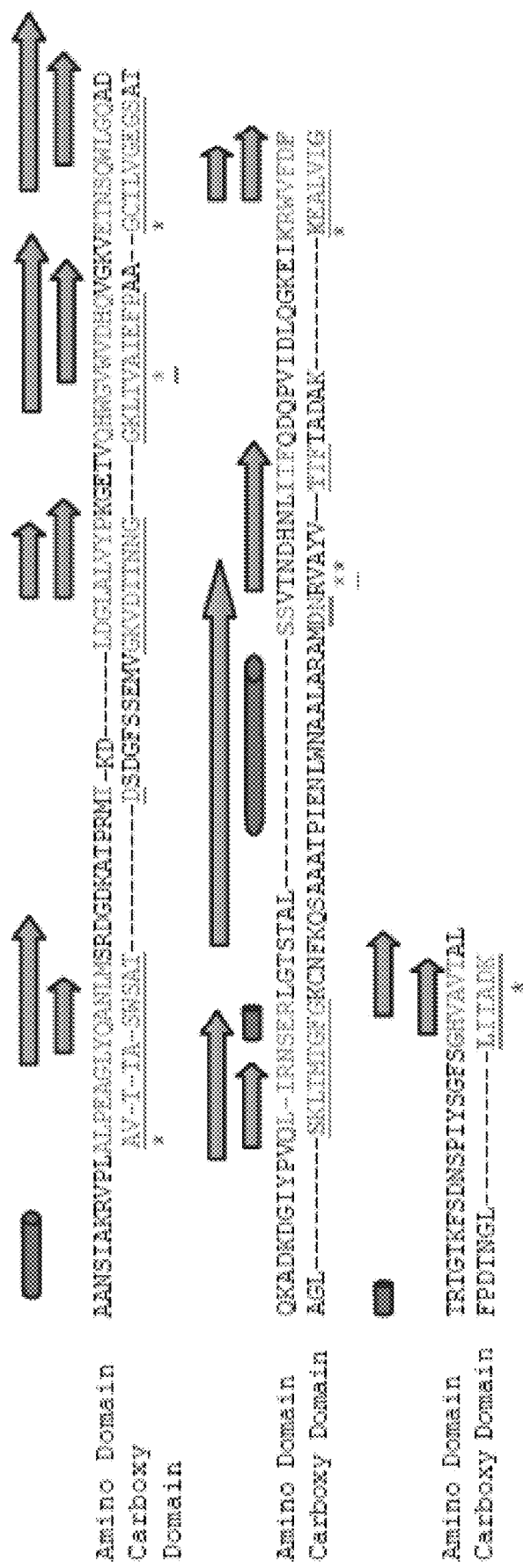
Figure 17C:
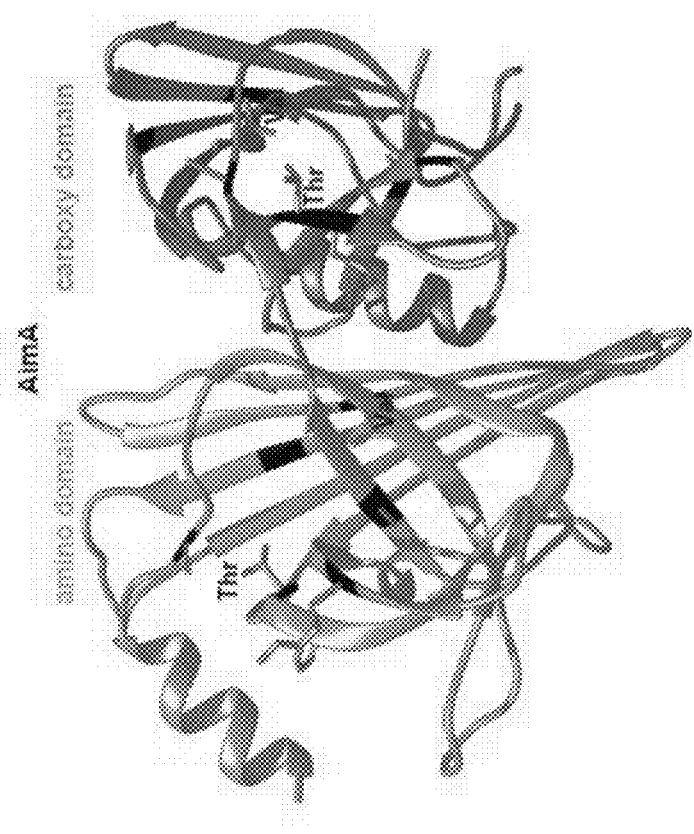
Figure 17B:
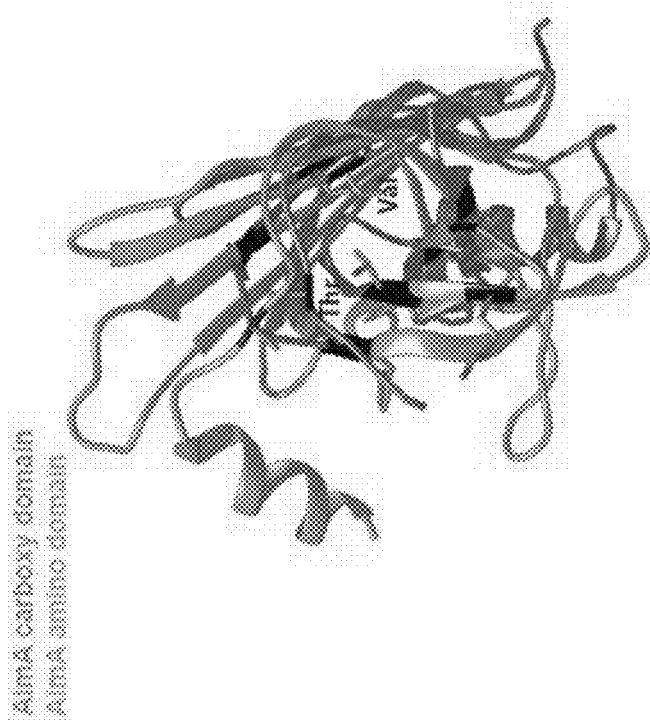

FIGS. 17A-17C are a series of panels showing structural comparison of N-term and C-term domains of AimA. FIG. 17A is a structure-based sequence alignment of N-term (amino acids 22-185 of SEQ ID NO: 1) and C-term (amino acids 192-313 of SEQ ID NO: 1) domains of AimA. Underlined text in C-term domain (and corresponding sequence in N-term domain) indicates regions that align in the structures. Arrows, β-strands, and cylinders, α-helices, above the text represent the secondary structure, with the top symbols corresponding to the N-term domain. Stars show the seven residues that align in the structures, with underlined stars indicating the Val and Thr residues that may be functionally relevant. FIG. 17B shows an overlay of N-term (orange) and C-term (teal) domain of AimA. The seven structurally conserved residues are mapped. FIG. 17C shows the full length AimA structure with the seven structurally conserved regions shown as sticks.

Figure 18A:
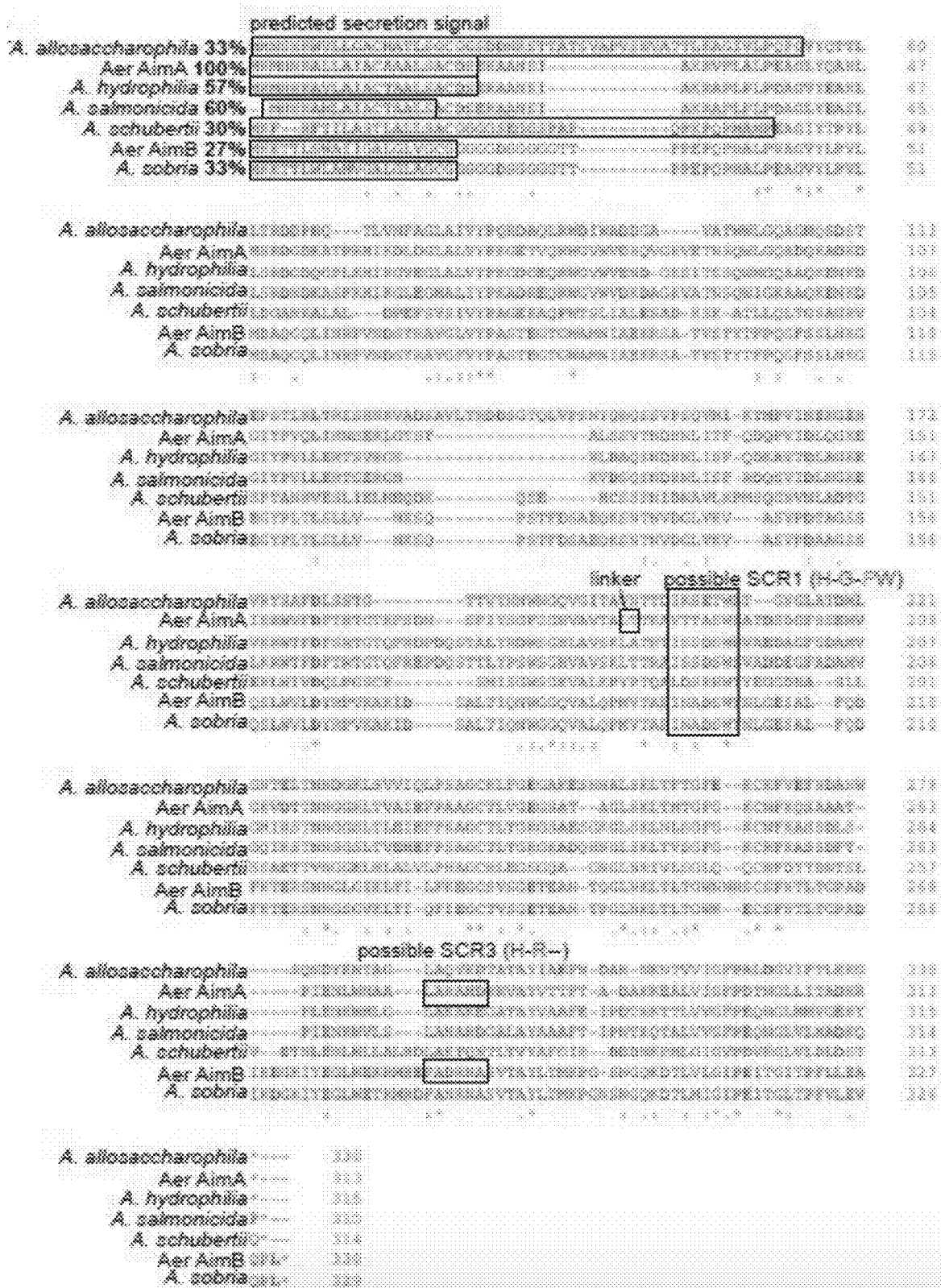
Figure 18B:
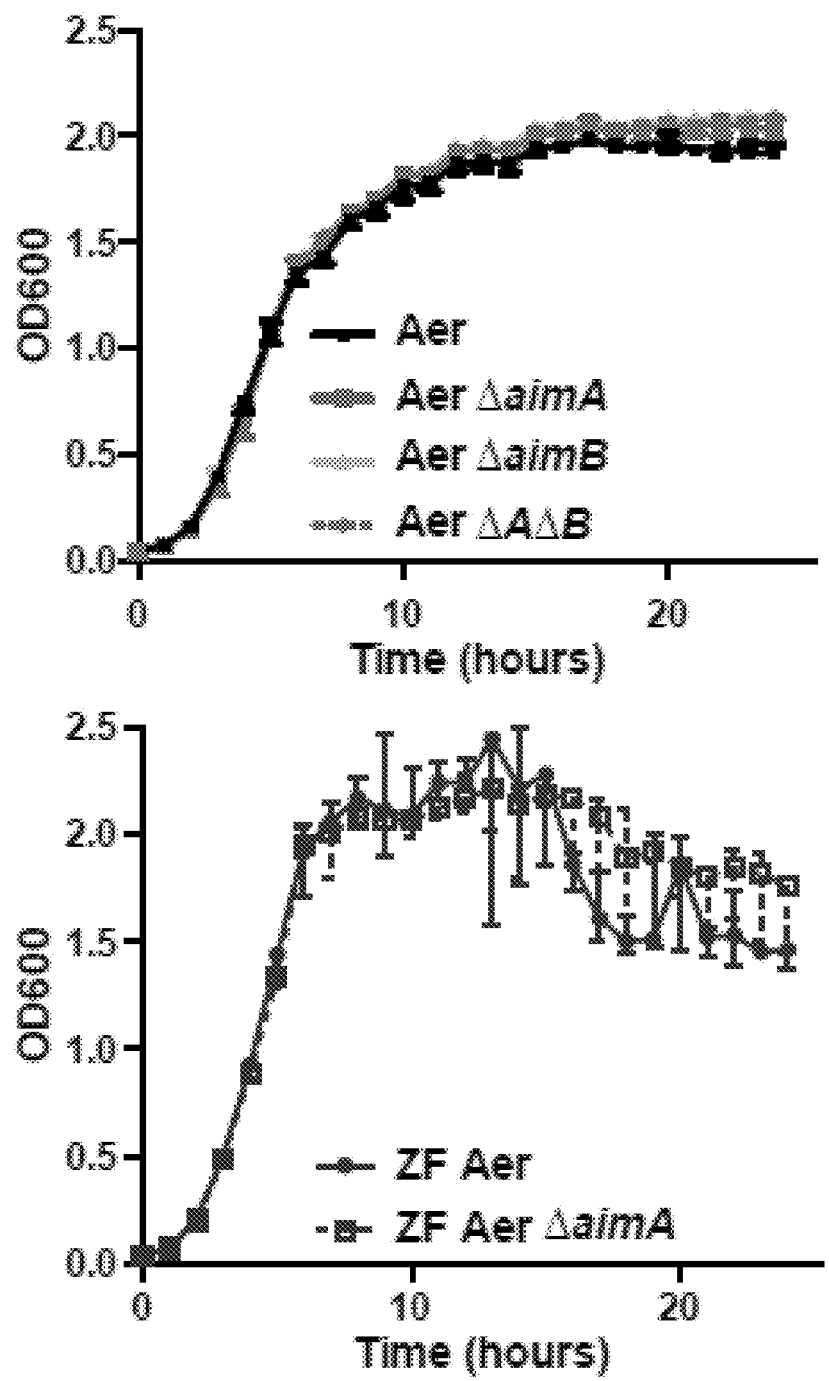

FIGS. 18A and 18B are panels showing homologs to AimA across the Aeromonas genus. FIG. 18A is a Clustal Omega alignment of six AimA homologs with AimA. The predicted secretion signal, the linker between the N- and C-term, and two possible lipocalin SCRs are indicated on the alignment. A. allosaccharophila, SEQ ID NO: 12; Aer AimA, SEQ ID NO: 1; A. hydrophila, SEQ ID NO: 13; A. salmonicida, SEQ ID NO: 14; A. schubertii, SEQ ID NO: 15; Aer AimB, SEQ ID NO: 11; A. sobria, SEQ ID NO: 16. FIG. 18B is a graph showing in vitro growth curves of Aer ΔaimA, Aer ΔaimB, and Aer ΔAΔB in A. veronii strain Hm21 (top), and ZF Aer ΔaimA in the zebrafish Aeromonas background (bottom) do not have growth defects in vitro.

Figure 19D:
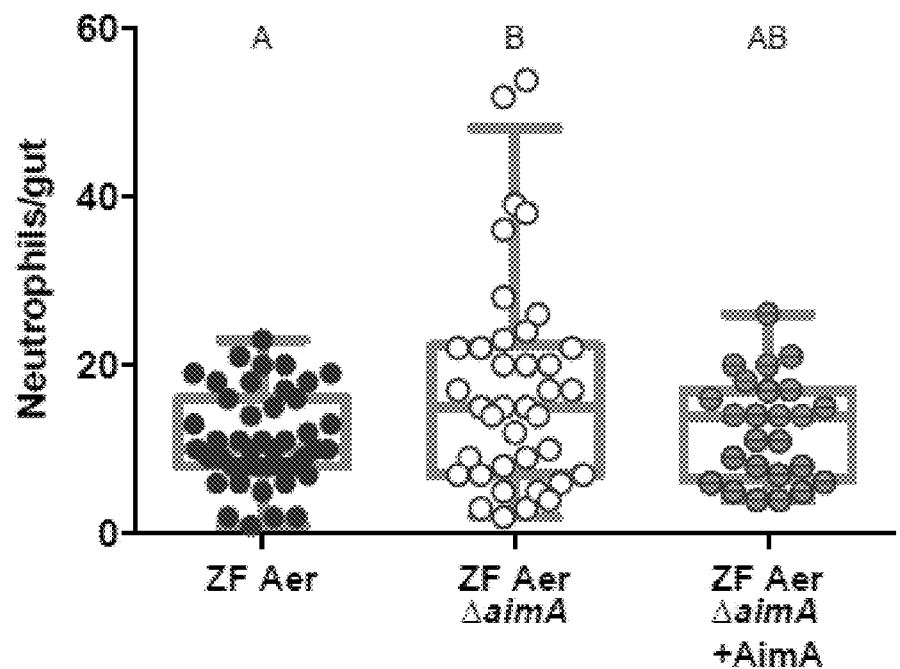

FIGS. 19A-19E are a series of panels showing that AimA reduces neutrophil influx and promotes colonization of Aeromonas. FIG. 19A shows a structural overlay of AimA and the model of AimB (gray) generated by I-TASSER using AimA as a threading structure. FIG. 19B is a graph showing intestinal neutrophil response to wild-type Aeromonas, ΔAimA, ΔAimB, and ΔAΔB. Each of the single mutants induces a similar neutrophil response to wild type, while the double mutant induces significantly greater response. This phenotype is rescued by treatment with 100 ng/ml purified AimA. FIG. 19C is a graph showing colonization level of wild-type Aeromonas, ΔAimA, ΔAimB, and ΔAΔB. Each of the single mutants colonized as well as wild type, while the double mutant had a significantly reduced colonization level. This phenotype was rescued by treatment with 100 ng/ml purified AimA. Neutrophil response was increased (FIG. 19D) and colonization level was decreased FIG. 19E in the zebrafish Aeromonas isolate AimA deletion. For all graphs, each dot represents one fish; n 23 from at least three independent experiments. Letters indicate significantly different groups, ANOVA with multiple comparisons.

Figure 20D:
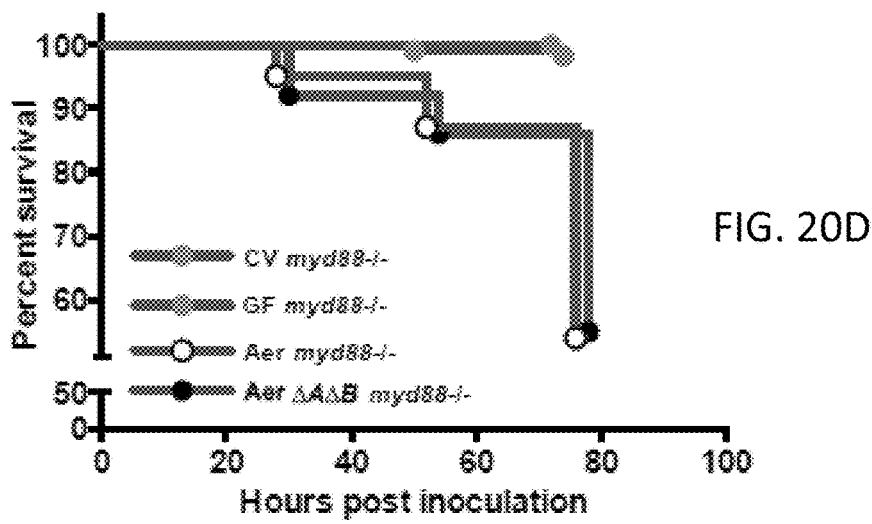
Figure 20E:
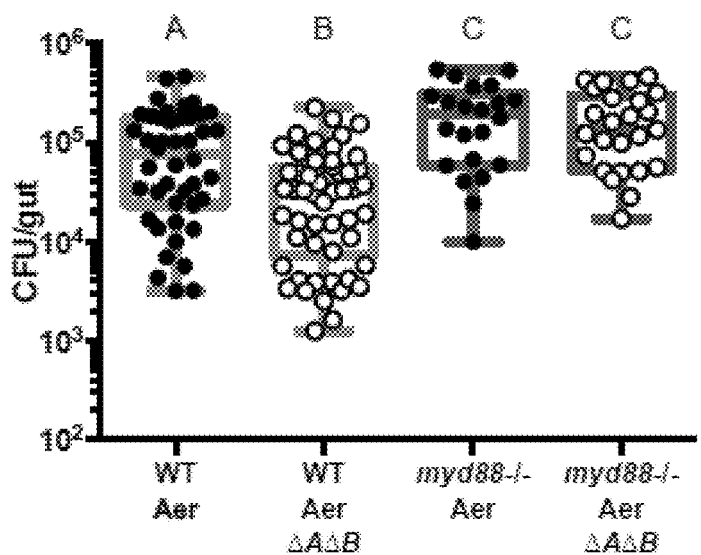
Figure 20F:
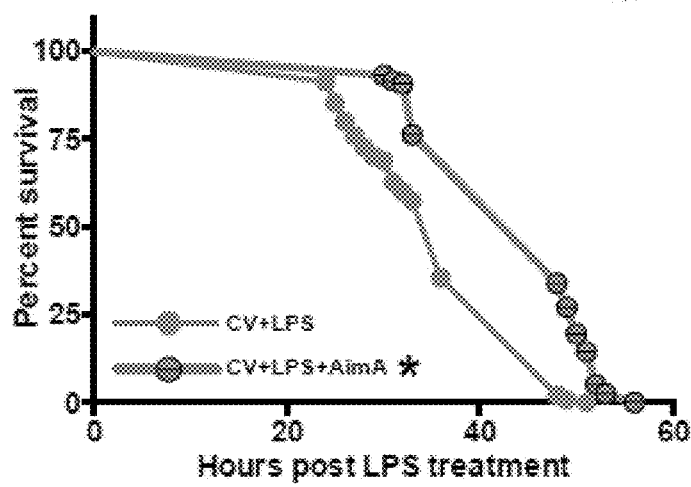

FIGS. 20A-20F are a series of panels showing that increased neutrophil response to Aeromonas ΔAΔB causes decreased survival rate. FIG. 20A is a graph showing the per capita effect of wild-type Aeromonas, ΔAimA, ΔAimB, and ΔAΔB. Each dot represents the average neutrophil response from a flask of 15 fish divided by the average colonization level from a flask of 15 fish, normalized to $10^4$. FIG. 20B is a graph showing survival curves of zebrafish mono-associated with each of the A. veronii strain Hm21 Aim mutants. Colonization with any of the Aim protein mutants reduced host survival by three days post-infection. *indicates significant difference from the survival curve with wild-type Aeromonas, Mantel-Cox test. FIG. 20C is a graph showing that $myd88^{-/-}$ transgenic fish lack a neutrophil response to bacteria. Each dot represents one fish. FIG. 20D is a graph showing survival curves of $myd88^{-/-}$ zebrafish over a 3-day infection. $myd88^{-/-}$ mutants inoculated with either wild-type or ΔAΔB Aeromonas experienced a reduction in survival by 3-days post infection. FIG. 20E is a graph showing ΔAΔB colonization was rescued to wild-type colonization levels in $myd88^{-/-}$ transgenic fish. Further, both wild-type Aeromonas and ΔAΔB reached significantly higher colonization levels in the $myd88^{-/-}$ transgenic fish compared to wild-type fish, indicating that the innate immune response limits commensal bacterial growth. FIG. 20F is a graph showing survival curves of conventionally raised (CV) fish treated with LPS or with LPS and AimA. *indicates significant difference from the survival curve with LPS treatment, Mantel-Cox test. For all graphs, letters indicate significance by ANOVA with multiple comparisons.

SEQUENCE LISTING

The nucleic and amino acid sequences provided herein or in the accompanying Sequence Listing are shown using standard letter abbreviations for nucleotide bases and amino acids. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Nov. 22, 2021, and is 33,368 bytes, which is incorporated by reference herein.

SEQ ID NO: 1 is an exemplary amino acid sequence of *A. veronii* AP (also referred to as AimA or Aer AimA).

SEQ ID NO: 2 is an exemplary nucleic acid sequence encoding *A. veronii* AP.

SEQ ID NOs: 3 and 4 are forward and reverse primers, respectively, for amplification of an *A. veronii* AP nucleic acid.

SEQ ID NOs: 5 and 6 are forward and reverse primers, respectively for amplification of a chloramphenicol resistance cassette.

SEQ ID NOs: 7-10 are primers used for amplification of an approximately 1000 base pair region upstream and downstream of the AP gene in *A. veronii* Hm21.

SEQ ID NO: 11 is the amino acid sequence of *A. veronii* AimB protein.

SEQ ID NO: 12 is the amino acid sequence of an *A. allosaccharophila* AIM protein.

SEQ ID NO: 13 is the amino acid sequence of an *A. hydrophila* AIM protein.

SEQ ID NO: 14 is the amino acid sequence of an *A. salmonicida* AIM protein.

SEQ ID NO: 15 is the amino acid sequence of an *A. schubertii* AIM protein.

SEQ ID NO: 16 is the amino acid sequence of an *A. sobria* AIM protein.

SEQ ID NO: 17 is a nucleic acid sequence encoding *A. veronii* AimB.

SEQ ID NO: 18 is a nucleic acid sequence encoding an *A. allosaccharophila* AIM protein.

SEQ ID NO: 19 is a nucleic acid sequence encoding an *A. hydrophila* AIM protein.

SEQ ID NO: 20 is a nucleic acid sequence encoding an *A. salmonicida* AIM protein.

SEQ ID NO: 21 is a nucleic acid sequence encoding an *A. schubertii* AIM protein.

SEQ ID NO: 22 is a nucleic acid sequence encoding an *A. sobria* AIM protein.

SEQ ID NO: 23 is SCR 1 and SCR3 amino acid sequences from mouse lipocalin.

SEQ ID NO: 24 is SCR 1 and SCR3 amino acid sequences from mouse major urinary protein.

SEQ ID NO: 25 is SCR 1 and SCR3 amino acid sequences from bovine BosD2.

SEQ ID NO: 26 is SCR 1 and SCR3 amino acid sequences from insect nitrophorin.

SEQ ID NO: 27 is SCR 1 and SCR3 amino acid sequences from AimA carboxy terminal domain.

SEQ ID NO: 28 is SCR 1 and SCR3 amino acid sequences from insect bilin binding protein.

SEQ ID NO: 29 is SCR 1 and SCR3 amino acid sequences from *E. coli* lipocalin.

SEQ ID NO: 30 is SCR 1 and SCR3 "motif" amino acid sequences.

DETAILED DESCRIPTION
I. Abbreviations

| | |
|---|---|
| AIM | *Aeromonas* immune modulator (also referred to as AP or protein 1882, in some cases) |
| AP | bacterial anti-inflammatory protein (also referred to as protein 1882) |
| BTD | beta-trefoil domain |
| CFS | cell-free supernatant |
| CV | conventionally reared |
| DPF | days post-fertilization |
| DT2SS or AT2SS | type II secretion system deletion |
| GF | germ-free reared |
| GFP | green fluorescent protein |
| IBD | inflammatory bowel disease |
| MPO | myeloperoxidase |
| T2SS | type II secretion system |
| WT | wild type |

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, public database entries (e.g., nucleic acid or amino acid Accession Nos.) and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Effective amount: An amount of an agent or composition that alone, or together with a pharmaceutically acceptable carrier and/or one or more additional agents, induces the desired response. Effective amounts of an agent can be determined in many different ways, such as assaying for a reduction in neutrophil recruitment, delay (or even prevention) of onset of a condition associated with inflammation, or a reduction or amelioration of one or more symptoms of a subject with inflammation. Effective amounts also can be determined through various in vitro, in vivo, or in situ assays, including, but not limited to those described herein.

Germ-free: An animal born and reared in aseptic conditions having no microorganisms living on or in it (for example, no bacteria in the gut of the animal).

Gnotobiotic: An animal in which only known strains of microorganisms are present. For example, a germ-free animal exposed to (e.g., intentionally inoculated with) one or more known bacterial strains is gnotobiotic. Germ-free animals are also gnotobiotic, as their microbial status is known. In contrast, conventionally reared animals (born and raised without absolute control of microorganism exposure) have a microbiota of many, and in most cases hundreds or thousands of organisms, which population will vary from animal to animal.

Gut: The term "gut" is used herein to refer to the digestive tract. Zebrafish do not have a stomach, rather their gut includes an intestinal bulb, the mid-intestine, and the caudal intestine (beginning at the esophageal junction and ending at the anus). The function of the zebrafish gut is analogous to the small and large intestine in mammals. Therefore, in some examples, gut refers to the intestine (such as the small and/or large intestine).

Isolated: An "isolated" or "purified" biological component (such as a nucleic acid, peptide, protein, or cell) has been substantially separated, produced apart from, or purified away from other biological components in which the component naturally occurs, for example, other chromosomal and extrachromosomal DNA and RNA, proteins, and/or cells. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its standard environment or a production vessel. Preferably, a preparation is purified such that the biological component represents at least 50%, such as at least 70%, at least 90%, at least 95%, or greater, of the total biological component content of the preparation.

Heterologous: Originating from a different genetic sources or species. For example, a nucleic acid that is heterologous to a cell originates from an organism or species other than the cell in which it is expressed. In one specific, non-limiting example, a heterologous nucleic acid includes an *Aeromonas veronii* nucleic acid that is present or expressed in a different bacterial cell (such as an *E. coli* cell) or in an algal, plant, or mammalian cell. Methods for introducing a heterologous nucleic acid into bacterial, algal, plant, and mammalian cells are well known in the art, for example transformation with a nucleic acid, including electroporation, lipofection, and particle gun acceleration.

In another example of use of the term heterologous, a nucleic acid operably linked to a heterologous promoter is from an organism or species other than that of the promoter. For example, an *Aeromonas veronii* acid may be linked to a heterologous bacterial, viral, or mammalian promoter. In other examples of the use of the term heterologous, a nucleic acid encoding a polypeptide (such as an anti-inflammatory polypeptide disclosed herein) or portion thereof is operably linked to a heterologous nucleic acid encoding a second polypeptide or portion thereof, for example to form a non-naturally occurring fusion protein.

Inflammation: A localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods well known in the art, such as the number of white blood cells, the number of polymorphonuclear leukocytes (PMN, such as neutrophils, eosinophils, basophils, and/or mast cells), a measure of the degree of PMN activation, or a measure of the amount of cytokines present.

A primary inflammation disorder is a disorder that is caused by the inflammation itself. A secondary inflammation disorder is inflammation that is the result of another disorder. Inflammation can lead to inflammatory diseases, such as rheumatoid arthritis, osteoarthritis, inflammatory lung disease (including chronic obstructive pulmonary lung disease), inflammatory bowel disease (including ulcerative colitis and Crohn's Disease), Hirschsprung disease (such as Hirschsprung associated enterocolitis), pelvic inflammatory disease, periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis), irritable bowel syndrome, necrotizing enterocolitis, atopy, and the like.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Inflammation is typically self-limiting and resolution (for example, clearance of activated inflammatory cells) occurs when the threat of infection or tissue damage is eliminated. Prolonged inflammation, known as chronic inflammation, leads to a progressive shift in the type of cells which are present at the site of inflammation and is characterized by simultaneous destruction and healing of the tissue from the inflammatory process.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and/or cells. Nucleic acid molecules and proteins that have been "isolated" include nucleic acid molecules and proteins purified by standard purification methods or prepared by recombinant expression in a host cell, as well as chemically synthesized nucleic acid molecules and proteins.

Myeloperoxidase (MPO): An enzyme released by activated neutrophils that metabolizes hydrogen peroxide generated by the neutrophils and chloride ion to produce hypochlorous acid (HOCl), which is cytotoxic. MPO requires heme as a cofactor.

Neutrophil: A type of white blood cell (also known as neutrophil granulocytes) that is part of the class of polymorphonuclear leukocytes. They are the most abundant type of white blood cells in mammals. During acute inflammation, neutrophils are recruited to the site of inflammation or injury by chemotaxis toward chemokines, complement factors, leukotrienes, and/or fMLP. Neutrophils are phagocytic and can internalize and kill many microorganisms. They also release various cytotoxic compounds, including myeloperoxidase, defensins, cathepsin, alkaline phosphatase, lysozyme, NADPH oxidase, and gelatinase, through the process of degranulation.

Operably linked: A first nucleic acid is operably linked to a second nucleic acid when the first nucleic acid is placed in a functional relationship with the second nucleic acid. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A nucleic acid or protein that is not naturally occurring or has a sequence that is made by an artificial combination of two otherwise separated segments of nucleotides or amino acids. This artificial combination is often accomplished by chemical synthesis or, more commonly, by the artificial manipulation of isolated segments of nucleic acids, e.g., by genetic engineering techniques such as those described in Sambrook et al. *Molecular Cloning: A Laboratory Manual*, 3$^{rd}$ ed., Cold Spring Harbor Laboratory Press, N Y, 2001. The term recombinant includes nucleic acids or proteins that have been altered solely by addition, substitution, or deletion of a portion of the nucleic acid sequence or amino acid sequence, respectively.

Sample (or biological sample): A specimen containing genomic DNA, RNA (including mRNA), protein, or combinations thereof, obtained from a subject. Examples include, but are not limited to, peripheral blood (or fractions thereof), fine needle aspirate, urine, saliva, feces, tissue biopsy, surgical specimen, and autopsy material. In one example, a sample includes a tumor biopsy (such as a colorectal tumor tissue biopsy) or an intestinal tissue biopsy.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al., *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

One of skill in the art will appreciate that the particular sequence identity ranges provided herein are for guidance only; it is possible that strongly significant homologs or orthologs could be obtained that fall outside the ranges provided.

Subject: Living multi-cellular vertebrate organism, a category that includes vertebrates, including human and non-human mammals.

Therapeutically effective amount: An amount of an agent or composition that alone, or together with a pharmaceutically acceptable carrier and/or one or more additional therapeutic agents, induces the desired response. Effective amounts of an agent can be determined in many different ways, such as assaying for a reduction in inflammation, delay (or even prevention) of onset of a condition associated with inflammation (such as inflammatory bowel disease), or a reduction or amelioration of one or more symptoms of a subject with inflammation. Effective amounts also can be determined through various in vitro, in vivo, or in situ assays.

Transduced and Transformed: A virus or vector "transduces" a cell when it transfers nucleic acid into the cell. A cell is "transformed" by a nucleic acid transduced into the cell when the DNA becomes replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, or particle gun acceleration.

Treating or Inhibiting: "Inhibiting" refers to inhibiting or reducing the full development of a condition or symptom (such as inflammation or an inflammatory response) or a disorder (such as an inflammatory disease). Inhibition of a condition or disease can span the spectrum from partial inhibition (reduction) to substantially complete inhibition (prevention) of the condition, symptom, or disease. In some examples, the term "inhibiting" refers to reducing or delaying the onset or progression of inflammation, an inflammatory response, or an inflammatory disease. In contrast, "treatment" refers to a therapeutic intervention that ameliorates a sign or symptom of a disease or pathological condition (such as an inflammatory disease) after it has begun to develop.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cell. Exemplary vectors include those for use in *E. coli*. Vectors also include viral vectors, such as, but not limited to, retrovirus, orthopox, avipox, fowlpox, capripox, suipox, adenovirus, herpes virus, alpha virus, baculovirus, Sindbis virus, vaccinia virus, and poliovirus vectors. Vectors also include vectors for expression in yeast cells.

In some examples, a heterologous nucleic acid (such as a nucleic acid encoding an *A. veronii* protein) is introduced into a vector to produce a recombinant vector, thereby allowing the nucleic acid to be renewably produced and or a protein encoded by the nucleic acid to be expressed.

III. Anti-Inflammatory Protein from *Aeromonas*

Disclosed herein are anti-inflammatory proteins from members of the intestinal microbiota, including *Aeromonas veronii*. In some embodiments, the anti-inflammatory protein is a polypeptide that comprises or consists of the amino acid sequence as set forth as SEQ ID NO: 1. In other embodiments, the anti-inflammatory protein is a polypeptide that comprises or consists of the amino acid sequence of SEQ ID NO: 11. In still further embodiments, the anti-inflammatory protein is a polypeptide that comprises or consists of the amino acid sequence of any one of SEQ ID NOs: 12-16.

In additional embodiments, an anti-inflammatory polypeptide disclosed herein has at least 75%, 85%, 90%, 95%, 96%, 97%, 98%, or 99% sequence identity to the amino acid sequence set forth in any one of SEQ ID NOs: 1 or 11-16. In other embodiments, the anti-inflammatory protein does not include the signal sequence, which is removed from the mature protein. In some examples, the signal sequence is predicted to include the first 22 amino acids of SEQ ID NO: 1. Thus, in some examples, the mature polypeptide can have an amino acid sequence with at least 80%, 85%, 90%, 95%, 96%, 97%, 98%, 99%, or 100% sequence identity to amino acids 23-313 of SEQ ID NO: 1. In other examples, the mature anti-inflammatory has an amino acid sequence with at least 80%, 85%, 90%, 95%, 96%, 97%, 98%, 99%, or 100% sequence identity to any one of SEQ ID NOs: 11-16, but lacking the predicted secretion signal shown in FIG. 18A. In one example, the mature polypeptide has an amino acid sequence with at least 80%, 85%, 90%, 95%, 96%, 97%, 98%, 99%, or 100% sequence identity to amino acids 21-330 of SEQ ID NO: 11.

Exemplary sequences can be obtained using computer programs that are readily available on the internet and the amino acid sequences set forth herein. In some examples, the polypeptide retains a function of the anti-inflammatory protein, such as decreasing the number or activation of neutrophils and/or reducing or inhibiting inflammation in a subject.

In additional embodiments, an anti-inflammatory protein (such as any one of SEQ ID NOs: 1 and 11-16) includes a portion or fragment of the protein. In some examples, the anti-inflammatory protein or portion thereof includes at least 20 contiguous amino acids of any one of SEQ ID NOs: 1 and 11-16, for example, at least 30, at least 50, at least 75, at least 100, at least 150, at least 200, at least 250, at least 300, at least 350, at least 400, at least 450, or more amino acids of the protein. In one example, a fragment of AP includes the mature protein (for example, AP that does not include the signal sequence, such as amino acids 23-313 of SEQ ID NO: 1). In other examples, a portion or fragment of an anti-inflammatory protein includes one or more domains of AP. In some examples, a domain may include a portion of AP with structural similarity to a β-trefoil domain (for example, with similarity to a BTD found in one or more cytokines), such as amino acids 103-176 of SEQ ID NO: 1 or amino acids 148-176 of SEQ ID NO: 1. One of ordinary skill in the art will recognize that the boundaries of the domain are not exact and in some examples may include additional or fewer amino acids (for example, about 20, 19, 18, 17, 16, 15, 14, 13, 12, 11, 10, 9, 8, 7, 6, 5, 4, 3, 2, or 1 more or less amino acids from either end of the domain).

In other embodiments, the anti-inflammatory protein includes an N-terminal domain or a C-terminal domain of any one of SEQ ID NOs: 1 and 11-16. In some embodiments, the N-terminal domain or the C-terminal domain of any one of SEQ ID NOs: 1 and 11-16 is about 130-190 amino acids in length (such as about 130-150, 1430-160, 150-170, or 170-190 amino acids in length). In some examples, the anti-inflammatory protein includes or consists of the N-terminal domain of Aer AimA (such as amino acids 1-185, or amino acids 23-185 of SEQ ID NO: 1). In other examples, the anti-inflammatory protein includes or consists of the C-terminal domain of Aer Aim A (such as amino acids 192-313 of SEQ ID NO: 1). In still other examples, the anti-inflammatory protein includes or consists of the N-terminal domain of Aer AimB (such as amino acids 1-188, or amino acids 21-188 of SEQ ID NO: 11). In further examples, the anti-inflammatory protein includes or consists of the C-terminal domain of Aer AimB (such as amino acids 189-330 of SEQ ID NO: 11). The boundaries of the N-terminal and C-terminal domains are not exact and in some examples may include additional or fewer amino acids (for example, about 20, 19, 18, 17, 16, 15, 14, 13, 12, 11, 10, 9, 8, 7, 6, 5, 4, 3, 2, or 1 more or less amino acids from either end of the domain). Thus in some examples, an AimA or AimB (or corresponding protein from another species) N-terminal domain may include about the first 170-190 amino acids of the protein and an AimA or AimB (or corresponding protein from another species) C-terminal domain may include from about amino acid 170 to amino acid 190 to the end of the protein.

Furthermore, one of ordinary skill in the art can identify corresponding anti-inflammatory AP proteins and/or domains from other anti-inflammatory AP proteins, for example a corresponding AP from a bacterium other than *A. veronii* or from another organism. Exemplary proteins related to the *A. veronii* AP protein (such as SEQ ID NO: 1) include proteins from *Aeromonas salmonicida* (e.g., GenBank Accession No. WP_034524138.1; SEQ ID NO: 14), *Aeromonas sobria* (e.g., GenBank Accession No. WP_042019195.1), *Aeromonas bestiarum* (e.g., GenBank Accession No. WP_043556138), *Aeromonas piscicola* (e.g., GenBank Accession No. WP_042869769.1), and *Aeromonas jandaei* (e.g., GenBank Accession No. WP_041209781.1).

Minor modifications of an anti-inflammatory protein primary amino acid sequence (such as the *Aeromonas* AP (AimA) or AimB disclosed herein) are also disclosed herein. Such modifications may result in polypeptides that have substantially equivalent activity as compared to the unmodified counterpart polypeptide described herein. Such modifications may be deliberate, for example as by site-directed mutagenesis, or may be spontaneous. All of the polypeptides produced by these modifications are included herein. Thus, a specific, non-limiting example of an anti-inflammatory protein is a conservative variant of the protein (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In other examples, the protein may include one or more non-conservative substitutions (for example 1-10 non-conservative substitutions, 2-5 non-conservative substitutions, 4-9 non-conservative substitutions, such as 1, 2, 5 or 10 non-conservative substitutions), so long as the protein retains anti-inflammatory activity.

In additional embodiments, the anti-inflammatory protein or portion thereof (such as an N-terminal domain or C-terminal domain) includes a tag (such as an N-terminal or C-terminal tag), for example for use in protein purification. One of skill in the art can select appropriate tags, such as a His-tag, a GST tag, or an antibody recognition sequence (such as a Myc-tag or HA-tag). The anti-inflammatory protein can also be produced as a fusion protein, either to facilitate expression and/or purification or to facilitate delivery to a subject. For example, fusion proteins including a therapeutic molecule (such as the disclosed anti-inflammatory proteins) and transferrin has been shown to be useful for oral delivery routes. In other examples, the disclosed anti-inflammatory proteins may include a detectable label, such as a radioisotope, fluorophore, or hapten.

Additional exemplary *Aeromonas* anti-inflammatory proteins include the amino acid sequences of GenBank Accession Nos. WP_021230730 (SEQ ID NO: 1), WP_005340784, WP_005357002, YP_004390739, WP_005342535, YP_001142339, WP_021140301, and WP_005310485; all of which are incorporated herein by reference as present in GenBank on May 16, 2014. One of ordinary skill in the art can identify additional candidate anti-inflammatory proteins related to the anti-inflammatory proteins disclosed herein, for example from other microbiota (for example, other bacteria from the zebrafish gut or bacteria from mammalian gut, such as human microbiota).

The structure of SEQ ID NO: 1 (also referred to herein as AP or protein 1882 or Aer AimA) was analyzed for conserved features using HHpred (available on the World Wide Web at toolkit.tuebingen.mpg.de/hhpred) using the AP sequence and selecting all protein databases. As shown in FIG. 7A, the N-terminus showed similarity to secretion signal sequences, consistent with this protein being processed by the type II secretion system (discussed in Example 1). In addition, the protein showed similarity to decaheme cytochrome C of *Shewanella oneidensis* (amino acids 6-175 of SEQ ID NO: 1) and to a beta-trefoil domain (BTD) that is also found in cytokines, including interleukin-18 (IL-18), and interleukin-1b (IL-1b). In some examples, the BTD domain includes amino acids 103-176 of SEQ ID NO: 1 or amino acids 148-176 of SEQ ID NO: 1.

As discussed above, AP includes a region that is predicted to contain a β-trefoil domain with homology to human cytokines IL-1β, IL-1α, and IL-1ra. Both IL-1β and IL-1α bind the type 1 IL-1 receptor (IL-1R1). IL-1R1 engages with the IL-1 receptor accessory protein (IL-1RAP) to form a complex that results in the recruitment of the MyD88 adaptor protein (FIG. 7B). This initiates a signaling cascade that causes the transcription factor, NF-κB, to translocate into the nucleus and initiate transcription of the pro-inflammatory cytokines Il1β, Il6, Il8, and tnfα. Interleukin 1 receptor antagonist (IL-1ra) dampens IL-1 signaling by binding IL-1R1 and preventing receptor complex formation with IL-1RAP. Normal function and levels of IL-1ra affect ulcerative colitis, and polymorphisms in the IL-1ra gene are associated with severity and susceptibility to UC (Carter et al., *Genes Immun.* 5:8-15, 2004), neutralizing IL-1ra exacerbates colitis (Feretti et al., *J. Clin. Invest.* 94:449-453, 1994), and administering exogenous IL-1ra (Ricci et al., *BMC Biotechnol.* 3:15, 2003) or inducing endogenous IL-1ra (Gresnigt et al., *PLoS Pathog.* 10:e1003936, 2014) reduces disease severity in animal models of inflammation (Dinarello, Blood 89:2095-2147, 1996; Dinarello *Blood* 118:3720-3732, 2011). The IL-1 family of cytokines (Huising et al. *Dev. Comp. Immunol.* 28:395-413, 2004) and neutrophil behavior and activity (Renshaw et al., *Blood* 108:3976-3978, 2006; Guyader et al. *Blood* 111:132-141, 2008) are conserved in zebrafish. Moreover, intestinal neutrophil influx in zebrafish depends on Myd88 (Bates et al., *Cell Host Microbe* 2:371-382, 2007), confirming this pathway's role in neutrophil behavior. Without being bound by theory, based on the biological activity and homology of AP, it is believed that AP may be a competitive inhibitor of binding sites on the cytokine receptor IL-1R1, potentially decreasing pro-inflammatory IL-1 signaling.

In additional embodiments, the anti-inflammatory protein disclosed herein (referred to as AP or Aer AimA is encoded by a nucleic acid sequence which comprises or consists of the nucleic acid sequence set forth as SEQ ID NO: 2. In further embodiments, the anti-inflammatory protein disclosed herein is encoded by a nucleic acid sequence which comprises or consists of the nucleic acid sequence of any one of SEQ ID NOs: 17-22.

In additional embodiments, a nucleic acid encoding an *Aeromonas* anti-inflammatory polypeptide disclosed herein has at least 75%, 85%, 90%, 95%, 96%, 97%, 98%, or 99% sequence identity to the nucleic acid sequence set forth in SEQ ID NO: 2 or a fragment thereof. In other embodiments, a nucleic acid encoding an *Aeromonas* anti-inflammatory polypeptide disclosed herein has at least 75%, 85%, 90%, 95%, 96%, 97%, 98%, or 99% sequence identity to the nucleic acid sequence of any one of SEQ ID NOs: 17-22 or a fragment thereof. For example, the nucleic acid can have a nucleic acid sequence with at least 80%, 85%, 90%, 95%, 96%, 97%, 98%, 99%, or 100% sequence identity to a nucleic acid encoding amino acids 23-313 of SEQ ID NO: 1 (such as nucleotides 67-939 of SEQ ID NO: 2) or a nucleic acid encoding amino acids 103-176 of SEQ ID NO: 1 (such as nucleotides 307-528 of SEQ ID NO: 2). In other examples, the nucleic acid has a nucleic acid sequence with at least 80%, 85%, 90%, 95%, 96%, 97%, 98%, 99%, or 100% sequence identity to a nucleic acid encoding amino acids 21-330 of SEQ ID NO: 11 (such as nucleotides 61-564 of SEQ ID NO: 17).

In other embodiments, the nucleic acid encodes includes an N-terminal domain or a C-terminal domain of any one of SEQ ID NOs: 2 and 17-22. In some embodiments, the N-terminal or C-terminal domain is about 390-570 nucleotides in length (such as about 390-450, 420-480, 450-510, 480-540, or 510-570 nucleotides in length). In some examples, the nucleic acid encodes an N-terminal domain of Aer AimA (for example, encodes amino acids 1-185, or amino acids 23-185 of SEQ ID NO: 1, such as nucleotides 1-555 or 67-555 of SEQ ID NO: 2). In other examples, the nucleic acid encodes a C-terminal domain of Aer Aim A (for example, encodes amino acids 192-313 of SEQ ID NO: 1, such as nucleotides 574-939 of SEQ ID NO: 2). In still other examples, the nucleic acid encodes an N-terminal domain of Aer AimB (for example, encodes amino acids 1-188, or amino acids 21-188 of SEQ ID NO: 11, for example, nucleic acids 1-564 or 61-564 of SEQ ID NO: 17). In further examples, the nucleic acid encodes a C-terminal domain of Aer AimB (for example, encodes amino acids 189-330 of SEQ ID NO: 11, such as nucleotides 565-990 of SEQ ID NO: 17). The boundaries of the N-terminal and C-terminal domains are not exact and in some examples may include additional or fewer nucleotides (for example, about 20, 19, 18, 17, 16, 15, 14, 13, 12, 11, 10, 9, 8, 7, 6, 5, 4, 3, 2, or 1 more or less nucleotides from either end of the domain).

Exemplary sequences can be obtained using computer programs that are readily available on the internet and the amino acid sequences set forth herein. In some examples, the nucleic acid encodes a polypeptide that retains a function of the anti-inflammatory protein, such as decreasing the number or activation of neutrophils and/or reducing or inhibiting inflammation in a subject.

Additional exemplary *Aeromonas* nucleic acids encoding the disclosed proteins include the nucleic acid sequences of GenBank Accession Nos. NZ_ATFB01000030 (nucleotides 64518-65459; SEQ ID NO: 2), NZ_JH815583 (nucleotides 116798-117739, complement), NZ_JH815589 (nucleotides 391175-392116, complement), NC_015424 (nucleotides 103273-104214), NZ_JH823256 (nucleotides 1061308-1062153), NC_009348 (nucleotides 2743728-2744681, complement), NZ_ARYZ01000054 (nucleotides 2343-3290), and NZ_AGV001000002 (nucleotides 295610-297457); all of which are incorporated herein by reference as present in GenBank on May 16, 2014. One of ordinary skill in the art can identify additional candidate nucleic acids encoding anti-inflammatory proteins related to the anti-inflammatory proteins disclosed herein, for example from other microbiota.

Minor modifications of nucleic acids encoding an anti-inflammatory protein primary amino acid sequence (such as the *Aeromonas* AP disclosed herein) are also contemplated herein. Such modifications to the nucleic acid may result in polypeptides that have substantially equivalent activity as compared to the unmodified counterpart polypeptide described herein. Such modifications may be deliberate, for example as by site-directed mutagenesis, or may be spontaneous. All of the nucleic acids produced by these modifications are included herein. Thus, a specific, non-limiting example of modified nucleic acid encoding an anti-inflammatory protein is a nucleic acid encoding conservative variant of the protein (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In other examples, the nucleic acid may encode a protein including one or more non-conservative substitutions (for example 1-10 non-conservative substitutions, 2-5 non-conservative substitutions, 4-9 non-conservative substitutions, such as 1, 2, 5 or 10 non-conservative substitutions), so long as the encoded protein retains anti-inflammatory activity.

In additional embodiments, the nucleic acid encoding the anti-inflammatory protein further includes a nucleic acid sequence encoding a tag (such as an N-terminal or C-terminal tag), for example for use in protein purification. One of skill in the art can select nucleic acids encoding appropriate tags, such as a His-tag, a GST tag, or an antibody recognition sequence (such as a Myc-tag or HA-tag). The nucleic acid may also encode a fusion, for example, a nucleic acid encoding a fusion protein including a disclosed anti-inflammatory proteins and transferrin. In other examples, the disclosed nucleic acids may include a detectable label, such as a radioisotope, fluorophore, or hapten.

Nucleic acid molecules encoding an anti-inflammatory protein disclosed herein also include a recombinant DNA which is incorporated into a vector, into an autonomously replicating plasmid or virus, or into the genomic DNA of a prokaryote or eukaryote, or which exists as a separate molecule (such as a cDNA) independent of other sequences. A nucleic acid encoding an anti-inflammatory polypeptide (such as a nucleic acid encoding an *Aeromonas* anti-inflammatory peptide, for example SEQ ID NOs: 1, 11-16, or a fragment thereof) is in some examples operably linked to heterologous expression control sequences. An expression control sequence operably linked to a coding sequence is ligated such that expression of the coding sequence is achieved under conditions compatible with the expression control sequences. The expression control sequences include, but are not limited to, appropriate promoters, enhancers, transcription terminators, a start codon (e.g., ATG) in front of a protein-encoding nucleic acid, splicing signal for introns, maintenance of the correct reading frame of that gene to permit proper translation of mRNA, and stop codons. The expression control sequence(s) in some examples are heterologous expression control sequence(s), for example from an organism or species other than the protein-encoding nucleic acid. Thus, the protein-encoding nucleic acid operably linked to a heterologous expression control sequence (such as a promoter) comprises a nucleic acid that is not naturally occurring. In other examples, the nucleic acid is operably linked to a tag sequence (such as 6×His, HA tag, or Myc tag) or another protein-coding sequence, such as glutathione S-transferase or maltose binding protein.

Vectors for cloning and replication of the disclosed nucleic acid molecules include bacterial plasmids, such as bacterial cloning or expression plasmids. Exemplary bacterial plasmids into which the nucleic acids can be cloned include *E. coli* plasmids, such as pBR322, pUC plasmids (such as pUC18 or pUC19), pBluescript, pACYC184, pCD1, pGEM® plasmids (such as pGEM®-3, pGEM®-4, pGEM-T® plasmids; Promega, Madison, Wis.), TA-cloning vectors, such as pCR® plasmids (for example, pCR® II, pCR® 2.1, or pCR® 4 plasmids; Life Technologies, Grand Island, N.Y.) or pcDNA plasmids (for example pcDNA™3.1 or pcDNA™3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can be also be cloned into *B. subtilis* plasmids, for example, pTA1060 and pHT plasmids (such as pHT01, pHT43, or pHT315 plasmids). One of skill in the art can select additional vectors suitable for cloning and/or bacterial expression of anti-inflammatory proteins such as those disclosed herein.

In other embodiments, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDRS). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (20 or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

Viral vectors including the disclosed polynucleotides (such as polynucleotides encoding an anti-inflammatory protein) can also be prepared. A number of viral vectors have been constructed, including polyoma, SV40 (Madzak et al., 1992, *J. Gen. Virol.*, 73:15331536), adenovirus (Berkner, 1992, *Curr. Top. Microbiol. Immunol.*, 158:39-6; Berliner et al., 1988, *BioTechniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.* 158:91-123; On et al., 1990, *Gene*, 89:279-282), herpes viruses including HSV and EBV (Margolskee, 1992, *Curr. Top.*

Microbiol. Immunol., 158:67-90; Johnson et al., 1992, *J. Virol.*, 66:2952-2965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (Herweijer et al., 1995, *Hum. Gene Ther.* 6:1161-1167; U.S. Pat. Nos. 5,091,309 and 5,2217,879), alphaviruses (S. Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

DNA sequences encoding an anti-inflammatory polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Host cells can include microbial, yeast, insect and/or mammalian host cells. Methods of expressing DNA sequences having eukaryotic or viral sequences in prokaryotes are well known in the art. Non-limiting examples of suitable host cells include bacteria, archea, insect, fungi (for example, yeast), *Mycobacterium* (such as *M. smegmatis*), plant, and animal cells (for example, mammalian cells, such as human cells). Exemplary cells of use include *E. coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. *Meth. Enzymol.* volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression, desirable glycosylation patterns, or other features. As discussed above, techniques for the transformation of yeast cells, such as polyethylene glycol transformation, protoplast transformation and gene guns are also known in the art (see Gietz and Woods *Meth. Enzymol.* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with a polynucleotide encoding an anti-inflammatory protein polypeptide and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

IV. Methods of Treating or Inhibiting Inflammation

Disclosed herein are methods of treating or inhibiting inflammation in a subject. In some embodiments, the methods include administering to a subject an effective amount of a microbial anti-inflammatory protein (such as an *Aeromonas* anti-inflammatory protein), including, but not limited to the anti-inflammatory proteins disclosed herein (such as SEQ ID NOs: 1, 11-16, or fragments or portions thereof). The anti-inflammatory protein may be administered in any form, including administration of cells producing an anti-inflammatory protein disclosed herein (e.g., *A. veronii, A. salmonicida*, or *A. hydrophila*, or other bacteria recombinantly expressing or overexpressing an anti-inflammatory protein), a cell extract, or a preparation (such as a cell-free supernatant) from a cell producing an anti-inflammatory protein, an isolated or purified anti-inflammatory protein (including, but not limited to SEQ ID NO: 1, 11-16, or a fragment thereof), or a nucleic acid encoding an anti-inflammatory protein (including, but not limited to, SEQ ID NO: 2, 17-22, or a portion thereof).

The anti-inflammatory proteins disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding an anti-inflammatory protein or a portion thereof into an expression vector, introducing the expression vector into a host cell (such as *E. coli*), and isolating the polypeptide (for example, as discussed in Section III). In some examples, the protein includes a tag (such as an N-terminal or C-terminal tag), for example for use in protein purification. One of skill in the art can select appropriate tags, such as a His-tag, a GST tag, or an antibody recognition sequence (such as a Myc-tag or HA-tag). In some embodiments, the anti-inflammatory protein is produced by bacteria (such as *Aeromonas* or another suitable bacteria) expressing the anti-inflammatory protein from an expression vector (such as a vector including a constitutive or a regulatable promoter). The anti-inflammatory protein may be administered to a subject as an isolated preparation from the bacteria, an extract or other preparation (such as cell-free supernatant), or the recombinant bacteria may be administered to the subject.

In some embodiments, the anti-inflammatory protein (such as a protein comprising the sequence of SEQ ID NO: 1 or a protein that is at least 80%, 85%, 90%, 95%, 98%, or 99% identical to SEQ ID NO: 1 or a fragment thereof) or a nucleic acid encoding the protein or fragment thereof is administered to a subject to treat or inhibit inflammation. In some examples, a fragment of the anti-inflammatory protein includes the processed mature protein, for example, lacking the signal sequence (such as amino acids 23-313 of SEQ ID NO: 1) or a domain of the protein (such as a BTD domain, for example amino acids 103-176 of SEQ ID NO: 1 or amino acids 148-176 of SEQ ID NO: 1), or polypeptides that are at least 80%, 85%, 90%, 95%, 98%, or 99% identical to the fragment of the anti-inflammatory protein. In other examples, a fragment of the anti-inflammatory protein includes an N-terminal or C-terminal domain (or both) of SEQ ID NO: 1, such as amino acids 1-185, or amino acids 23-185 of SEQ ID NO: 1, and/or amino acids 192-313 of SEQ ID NO: 1.

In other embodiments, an anti-inflammatory protein (such as a protein including the sequence of any one of SEQ ID NOs: 11-16, or a protein that is at least 80%, 85%, 90%, 95%, 98%, or 99% identical to any one of SEQ ID NOs: 11-16 or a fragment thereof) or a nucleic acid encoding the protein or fragment thereof is administered to a subject to treat or inhibit inflammation. In some examples, a fragment of the anti-inflammatory protein includes an N-terminal or C-terminal domain (or both) of SEQ ID NO: 11, such as amino acids 1-188, or amino acids 21-188 of SEQ ID NO: 11, and/or amino acids 189-330 of SEQ ID NO: 11.

In some examples, administration of the anti-inflammatory protein or fragment thereof (or nucleic acid encoding the protein or fragment thereof) reduces at least one marker of inflammation (such as number or activation of neutrophils) by at least about 10% (such as at least 15%, at least 20%, at least 25%, at least 30%, at least 40%, at least 50%, at least 60%, at least 70%, at least 80%, at least 90%, or more).

In some examples, the subject may have one of a number of conditions broadly categorized as an inflammatory disease or disorder. Such disorders include, but are not limited to, rheumatoid arthritis, osteoarthritis, inflammatory lung disease (including chronic obstructive pulmonary lung disease), inflammatory bowel disease (including ulcerative colitis and Crohn's Disease), Hirschsprung disease (such as Hirschsprung's associated enterocolitis), pelvic inflammatory disease, periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis), irritable bowel syndrome, necrotizing enterocolitis, or atopy. In particular embodiments, the subject has inflammatory bowel disease.

In other examples, the subject may have or be suspected to have sepsis or septic shock. Sepsis is a condition where the subject has an infection, and the subject's immune response to the infection damages the subject's own tissue(s). Sepsis is sometimes defined as presence of infection with systemic inflammatory response syndrome (SIRS). Sepsis is typically diagnosed by presence of infection in combination with altered mental state, increased respiratory rate (e.g., >22 breaths/minute), and low blood pressure (e.g., ≤100 mm Hg systolic pressure). Septic shock is low blood pressure due to sepsis that does not improve after treatment. Sepsis and septic shock are a life-threatening condition that is usually treated with antibiotics, intravenous fluids, and other supportive measures, such as oxygen, mechanical ventilation and/or dialysis. Animal models of sepsis include administration of lipopolysaccharide (LPS) to an animal (such as mice or zebrafish) and administration of intravenous bacteria (such as *E. coli*) in primate models, or cecal ligation and puncture (CLP).

The anti-inflammatory protein, nucleic acid encoding the anti-inflammatory protein, or cell expressing the anti-inflammatory protein can be administered to a subject in need of treatment using any suitable means known in the art. Methods of administration include, but are not limited to, intradermal, intramuscular, intraperitoneal, parenteral, subcutaneous, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent. In particular examples, the anti-inflammatory protein, nucleic acid encoding the anti-inflammatory protein, or a preparation including the anti-inflammatory protein (such as a cell extract or preparation or cells expressing the protein) is administered orally. In further examples, the anti-inflammatory protein, nucleic acid encoding the anti-inflammatory protein, or a preparation encoding the anti-inflammatory protein (such as a cell extract or preparation or cells expressing the protein) is administered intravenously. In other examples, the anti-inflammatory protein, nucleic acid encoding the anti-inflammatory protein, or a preparation encoding the anti-inflammatory protein (such as a cell extract or preparation or cells expressing the protein) is administered subcutaneously or intramuscularly.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic agents Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

The amount of anti-inflammatory protein, nucleic acid encoding the anti-inflammatory protein, or a preparation encoding the anti-inflammatory protein (such as a cell extract or preparation or cells expressing the protein) to be administered to a subject can be selected by one of ordinary skill in the art, for example from about 1 µg to 5 g anti-inflammatory protein (such as about 10 µg to 1 µg, 100 µg to 500 mg, or 1 mg to 100 mg). In other examples, the amount of anti-inflammatory protein or a preparation encoding the anti-inflammatory protein (such as a cell extract or preparation or cells expressing the protein) to be administered to a subject is about 0.001 mg/kg to about 1000 mg/kg (such as about 0.01 mg/kg to about 500 mg/kg, about 1 mg/kg to about 250 mg/kg, or about 10 mg/kg to 100 mg/kg).

The dosage can be administered one or more times per day, in divided doses (such as 2, 3, or 4 divided doses per day), or in a single dosage daily. The dosage can also be administered every 2 days, every 3 days, bi-weekly, once weekly, semi-weekly, or monthly. In some examples, an effective amount of anti-inflammatory protein is an amount that inhibits or ameliorates one or more symptoms of an inflammatory disease. In other examples, an effective amount of anti-inflammatory protein is an amount that decreases one or more markers of inflammation, such as number of white blood cells (such as neutrophils).

In particular examples, prior to, during, or following administration of a disclosed anti-inflammatory protein (or nucleic acid encoding the protein, or preparation of bacteria expressing the protein) the subject can receive one or more other anti-inflammatory therapies. Examples of such therapies include, but are not limited to, non-steroidal anti-inflammatory drugs (NSAIDs, such as aspirin, ibuprofen, naproxen, and celecoxib), corticosteroids (such as prednisone, methylprednisolone, or cortisone), or DMARDs (such as etanercept, adalimumab, infliximab, rituximab, or methotrexate). Combinations of these therapies can also be administered to a subject. In other examples, such as when the subject has or is suspected to have sepsis or septic shock, one or more other therapies, such as antibiotic therapy, intravenous fluids, vassopressors, or other supportive therapies, can be administered prior to, during, or following administration of a disclosed anti-inflammatory protein (or nucleic acid encoding the protein, or preparation of bacteria expressing the protein).

V. Methods of Identifying Modulators of Inflammation

Disclosed herein are methods for identifying modulators of immune responses, such as inflammation. In some embodiments, the methods include inoculating germ-free zebrafish (or a population of germ-free zebrafish) with one or more defined bacterial strains or CFS supernatant from one or more defined bacterial strains and/or one or more test compounds and determining the amount of inflammation, for example by measuring a marker of inflammation. In some examples, the zebrafish are transgenic for one or more genes, for example, are transgenic for green fluorescent protein (GFP) expressed under the control of the myeloperoxidase (MPO) promoter. In other embodiments, the methods include inoculating conventionally raised zebrafish (or a population of conventionally raised zebrafish) with one or more test compounds and determining the amount of inflammation, for example by measuring a marker of inflammation. In some examples, the conventionally raised zebrafish are transgenic or mutant for one or more genes, for example, Sox10.

In some examples, a marker of inflammation is the amount (such as number or percentage) of neutrophils or macrophages present, for example in the gut of the zebrafish. Presence or amount of neutrophils or macrophages in the gut can be determined by histological staining, in situ hybridization, or immunohistochemistry. In one example, presence or amount of neutrophils is determined by detection of a marker expressed under the control of a neutrophil-specific gene (such as green fluorescent protein (GFP) expressed from the myeloperoxidase (MPO) promoter, as described below). In other examples, a marker of inflammation is expression (such as the amount of expression) of one or more inflammatory genes, for example cytokines (such as TNFα) or expression of MPO. Expression of markers of inflammation can be detected using methods such as PCR (for example, RT-PCR, real-time PCR, quantitative real-time RT-PCR), in situ hybridization, Northern blotting, immunohistochemistry, Western blotting, flow cytometry, microscopy, or other techniques known to one of skill in the art.

In some examples, the presence or amount of the marker of inflammation in a zebrafish contacted or treated with a test compound is compared to a control. In some examples, the control is a zebrafish (or population of zebrafish) treated under the same conditions, but without treatment with the test compound. A decrease in the presence or amount of the marker of inflammation in the treated zebrafish (such as an decrease of at least about 10%, about 20%, about 50%, about 80%, about 90%, about 1.5-fold, about 2-fold, about 3-fold, about 5-fold, about 10-fold or more) as compared to in the control indicates that the compound inhibits immune response or inflammation.

Bacterial strains or test compounds identified as an inhibitor of immune response or inflammation may be selected for further testing. If the inhibitor is a bacterial strain or CFS from a bacterial strain, additional testing may be carried out to identify or purify one or more anti-inflammatory compounds from the bacterial strain.

Bacterial strains that may be used in the screening methods disclosed herein (either for inoculation of germ-free zebrafish or for preparing CFS with which the zebrafish are contacted) include, but are not limited to *Aeromonas, Vibrio, Variovorax, Delftia, Acinetobacter, Shewanella, Chitinibacter, Bosea, Exiguobacterium, Carnobacterium, Ensifer, Korcuia, Comamonas*, and *Lactobacillus*. Additional bacterial strains, such as additional strains found in the zebrafish or mammalian gut (such as the human gut) can also be tested for anti-inflammatory activity in the methods disclosed herein.

A "compound" or "test compound" is any substance or any combination of substances that is useful for achieving an end or result. Any compound that has potential (whether or not ultimately realized) to modulate immune response or inflammation can be tested using the methods of this disclosure.

Exemplary compounds include, but are not limited to, peptides, such as soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, F(ab')2 and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

In some examples, the number of neutrophils is measured by counting the number of neutrophils in the blood of a subject or in the gut of a subject. Methods for counting neutrophils include manual counting (for example examining a sample (such as blood or tissue under a microscope) and counting the number of neutrophils or automated methods, such as flow cytometry. Neutrophils can be identified by staining techniques, including histological stains (such as hematoxylin and eosin), immunohistochemistry using neutrophil-specific antibodies or combinations of antibodies (such as anti-CD11b, anti-CD68, anti-neutrophil elastase, anti-pANCA, or anti-MPO), or by detecting neutrophil-specific enzyme activity (such as chloroacetate esterase staining). In other examples, the number of neutrophils is measured using a label that is expressed under the control of a neutrophil-specific promoter (such as transgenic zebrafish expressing a fluorescent protein such as GFP under the control of the MPO promoter; Renshaw et al., *Blood* 108: 3976-3978, 2006). In some examples, influx or numbers of neutrophils is measured using light sheet microscopy (see, e.g., Baker et al., *J. Microsc.* 25:105-112, 2015, incorporated herein by reference), for example using light sheet microscopy to detect neutrophils expressing GFP under the control of the MPO promoter. A decrease in the number of neutrophil cells (such as an decrease of at least about 10%, about 20%, about 50%, about 80%, about 90%, about 1.5-fold, about 2-fold, about 3-fold, about 5-fold, about 10-fold or more) in zebrafish in the presence of one or more bacterial strains or test compounds as compared to in the absence of the one or more bacterial strains or test compounds indicates that the compound inhibits immune response or inflammation.

The following examples are provided to illustrate certain particular features and/or embodiments. These examples should not be construed to limit the disclosure to the particular features or embodiments described.

Example 1

Secreted *A. veronii* Anti-Inflammatory Factor

This example describes identification of a secreted factor from *A. veronii* with anti-inflammatory activity.

Methods

All experiments performed with zebrafish were done according to protocols approved by the University of Oregon Institutional Animal Care and Use Committee. Conventionally-raised wild-type (AB×Tu strain) and Tg(BACmpx:GFP)$^{i114}$ (referred to as mpx:GFP) (Renshaw et al., *Blood* 108:3976-3978, 2006) were maintained as described (Westerfield, The Zebrafish Book, University of Oregon Press, Eugene, Oreg., 2000). The mpx:GFP zebrafish are transgenic for an insertion of EGFP at the MPO ATG start site.

Zebrafish embryos were derived germ free (GF) as previously described (Bates et al., *Dev. Biol.* 297:374-386, 2006), except the fish were soaked in 0.1% polyvinylpyrolidone-iodine (PVP-I, Sigma-Aldrich, St. Louis, Mo.) for 2 minutes, washed three times in sterile embryo medium (EM), soaked in 0.003% bleach for 10 minutes, then washed in sterile EM. Subsequently, 15 GF embryos were transferred to sterile tissue culture flasks with 50 mL of EM. Mono-associated zebrafish were generated by inoculating the flask 4 days post fertilization (dpf) with $10^6$ colony forming units (CFU)/mL of bacteria. All manipulations to the GF flasks were performed under a class II A/B3 biological safety cabinet. The flasks were kept at 28° C. until analysis of myeloperoxidase positive (MPO+) cells.

To create an inducible expression vector for the AP protein, the AP gene was amplified using the following primers: F1882NdeI, 5'-CGTACATATGAT-GAAAATGCACAACAAAGCGCTGC-3' (SEQ ID NO: 3) and R1882XhoI, 5'-CTGACTCGAGT-TATCGCTTGTCAGCGGTGATCAG-3' (SEQ ID NO: 4) with NdeI and XhoI restriction sites included. The PCR amplification products and the vector (pET-21b) were digested with NdeI and XhoI (New England Biolabs, Ipswich, Mass.) and ligated using T4 ligase (NEB) following the manufacturer's protocol. Subsequently, the ligated product was transformed into BL21 *E. coli*. To induce AP expression, *E. coli* was treated with 0.1 M IPTG in early exponential phase and was allowed to grow and produce protein for 2 hours. This resulted in a supernatant that was dominated by AP (FIG. 8).

After *A. veronii* was grown over night to stationary phase and after protein induction in *E. coli*, concentrated cell-free supernatant (CFS) was prepared. The 50-mL cultures were centrifuged at 7000×g for 10 minutes at 4° C. Subsequently, the supernatant was filtered through a 0.22-μm sterile tube top filter (Corning Inc., NY). The sterile supernatant was concentrated at 4° C. for 1 hour at 3000×g with a centrifugal device that has a 10 kDa weight cut off (Pall Life Sciences). The concentration of the supernatant was determined with a Nanodrop and inoculated into the flasks for a final concentration of 500 ng/mL.

MPO+ cell analysis was performed on 6 dpf. The mpx: GFP zebrafish were anesthetized in Tricaine and mounted in 4% methylcellulose. Subsequently, their guts were sterilely dissected. The number of GFP-positive cells was quantified visually for each fish.

Results

In order to identify factors secreted by zebrafish gut microbiota that potentially alter innate immune responses, zebrafish larvae were reared conventionally (CV), germ-free (GF), in the presence of *A. veronii*, or in the presence of a mutant *A. veronii* strain lacking the type II secretion system (ΔT2SS; Maltz and Graf, *Appl. Environ. Microbiol.* 77:597-603, 2011). One strain of *A. veronii*, ZF01, induced significantly more neutrophil influx than the genetically similar *A. veronii* Hm21. This result suggested that *A. veronii* Hm21 secreted a factor that reduced neutrophil influx in the intestine and Hm21 was selected for further investigation.

The type II secretion system (T2SS) is the main terminal branch of the general secretion pathway and is involved in secretion of proteins including proteases, cellulases, pectinases, phospholipases, lipases, and toxins. The ΔT2SS *A. veronii* strain has a reduced number of secreted proteins compared to strains with an intact T2SS system. Zebrafish raised in the presence of ΔT2SS *A. veronii* Hm21 had a greater neutrophil response than those raised GF or in the presence of wild-type *A. veronii* (FIG. 1). CFS from wild-type *A. veronii* rescued the low neutrophil infiltration phenotype in zebrafish raised with ΔT2SS *A. veronii* (FIG. 2).

Mass spectrometry of CFS from wild type and ΔT2SS *A. veronii* revealed significant increases in several secreted proteins (Table 1). CFS from wild-type *A. veronii* was fractionated by ammonium sulfate precipitation, and fractions were tested for their ability to stimulate neutrophil response (FIG. 3). The activity was concentrated in one fraction. The fractions were analyzed by SDS-PAGE and the active fraction was found to contain two major bands—one of about 55 kD and one of about 35 kD (FIG. 4). The molecular weight of the proteins with increased amounts in wild-type versus ΔT2SS *A. veronii* was considered (Table 1) to select candidate anti-inflammatory proteins.

TABLE 1

Molecular weight of proteins increased in WT *A. veronii* as compared to ΔT2SS *A. veronii*

| MW (kD) | Protein |
| --- | --- |
| 109.316 | Metalloprotease stce OS = *Aeromonas veronii* (strain B565) |
| 51.919 | Chitin-binding protein, carbohydrate-binding module family (CBP) |
| 63.724 | Protease OS = *Aeromonas veronii* (strain B565) |
| 91.892 | Putative trimethylamine-N-oxide reductase 1 |
| 69.583 | Chitinase |
| 130.48 | Putative uncharacterized protein |
| 103.622 | Collagenase family |
| 53.921 | *Aeromonas* virulence factor (hemolysin) |
| 66.694 | Serine protease Ahe2 |
| 93.066 | Chitinase A |
| 145.483 | Pullulanase |
| 61.732 | UshA protein |
| 107.821 | Chitinase |
| 33.386 | Putative uncharacterized protein (called 1882 or AP) |
| 79.011 | Glycoside hydrolase family 18 |
| 70.456 | Twin-arginine translocation pathway signal |
| 78.444 | Predicted extracellular nuclease |
| 92.107 | Chitinase 92 |
| 73.333 | 2',3'-cyclic-nucleotide 2'-phosphodiesterase |

To test the activity of candidate *A. veronii* proteins, AP and CBP were each cloned and expressed in *E. coli*. The *E. coli* genome does not contain homologues of AP or CBP. CFS from the recombinant *E. coli* was applied to GF-reared zebrafish. Neutrophil influx was decreased by CFS from *E. coli* expressing AP; however CFS from *E. coli* expressing CBP had no effect on neutrophil influx (FIG. 5).

Example 2

Effect of AP on Response to Infection

This example describes the effect of AP on response of zebrafish to *Vibrio* infection.

Zebrafish were raised as described in Example 1, either GF or mono-associated with a *Vibrio* species isolated from zebrafish gut. After 48 hours of *Vibrio* infection (inoculated at $10^6$ cfu/ml), CFS from *E. coli* expressing AP was inoculated in the culture at 500 ng/ml. MPO positive cells in the gut were measured as described in Example 1.

Infection with *Vibrio* increased the neutrophil influx in zebrafish gut as compared to GF zebrafish (FIG. 6). Treatment of zebrafish infected with *Vibrio* with CFS from *E. coli* expressing anti-inflammatory protein AP reduced neutrophil influx in response to *Vibrio* infection to levels comparable to that in GF zebrafish (FIG. 6). CFS from *E. coli* carrying a control plasmid had no effect on neutrophil influx.

Example 3

Effect of AP in a Zebrafish Model of Colitis

This example describes the effect of AP in a zebrafish mutant (sox10) that is a model of colitis.

Zebrafish sox10 mutant fails to differentiate enteric neurons, resulting in a lack of rhythmic peristaltic activity (Renshaw et al., *Blood* 108:3976-3978, 2006) and is a model for colitis. These mutants had significantly higher bacterial loads than their wild-type siblings (FIG. 9A). 16S rRNA profiling of the sox10 gut microbiota revealed a reduced diversity (alpha diversity) compared to the microbiota from their wild-type siblings (FIG. 9B), which is similar to the types of microbial dysbiosis observed in ulcerative colitis (Renshaw et al., *Blood* 108:3976-3978, 2006). Furthermore, these mutants had a significantly increased level of neutrophils in their intestine (FIG. 9C), a phenotype that was transferred to wild-type zebrafish upon inoculation of germ-free fish with the microbiota from sox10 fish (FIG. 9D), similar to transmissible colitis mouse models (Zenewicz et al., *J. Immunol.* 190:5306-5312, 2013; Garrett et al., *Cell* 131:33-45, 2007). These data demonstrated that the sox10 fish can be used as a model for dysbiosis and transmissible intestinal inflammation. In addition, treating sox10 mutants with AP significantly reduced neutrophil influx to the intestine (FIG. 10).

Example 4

Effect of AP Knockout Strain in Zebrafish

This example describes a bacterial strain that does not express AP and its effect in zebrafish.

An *Aeromonas* AP knockout strain was produced using homologous recombination to replace the AP gene with a chloramphenicol resistance cassette ($cm^R$) (*A. veronii* Δap::$cm^R$). The $cm^R$ was amplified from the pKD3 plasmid (GenBank accession number AY048742) using the primers 1882 cm.Mid5 (5' GCGACAGCAAGGAATAAAAACTC; SEQ ID NO: 5) and 1882 cm.Mid3 (5' CACCCCTGCCGT-TAGCTGCTTAT; SEQ ID NO: 6). These primers include sequence that overlaps with Hm21 genome surrounding the AP gene sequence. An approximately 1000 base pair region upstream and downstream of the AP gene was amplified by PCR using the following primers: Cm1882.up3 (5'CTAAGGAGGATATTCATATGCAT; SEQ ID NO: 7), 1882.up5 (5' GATGGTCTGGGTATTGCCGTTG; SEQ ID NO: 8), cm1882.dn5 (5' CGAAGCAGCTCCAGCCTA-CACA; SEQ ID NO: 9), and 1882.dn3 (5' GCTGTTCGT-CATCGATCGGCGC; SEQ ID NO: 10). The amplification products were put together using the three products as a template and the 1882.up5 and 1882.dn3 primers. Subsequently, the piece was ligated into the pDMS197 plasmid (Edwards et al., *Gene* 207:149-157, 1998). The resulting plasmid was transformed into the *E. coli* λpir+SM10 strain, which was used to mate at 30° C. for 4 hours with *Aeromonas* Hm21. *Aeromonas* Hm21 ΔAP were selected by resistance to chloramphenicol and confirm by PCR.

This mutant did not have a growth defect in vitro and colonized the zebrafish to wild-type levels. In these experiments, infection of zebrafish with an *A. veronii* Hm21 whose AP was knocked out (ΔAP) induced more inflammation than wild-type *A. veronii* Hm21 (FIG. 11).

Example 5

Methods of Screening for Modulators of Immune Response or Inflammation

This example describes particular methods that can be used for screening for modulators of immune response or inflammation utilizing transgenic zebrafish that express GFP under the control of the MPO promoter. One skilled in the art will appreciate that methods that deviate from these specific methods can also be used to successfully screen for modulators of immune response or inflammation.

Protocol for screening anti-inflammatory protein:

Day 1: Set up mpo:GFP fish to cross naturally. Use dividers to prevent egg laying until the morning.

Day 2 (0 dpf):
1. By 9:00 am, move natural crosses into tanks with fresh water and pull dividers to allow fish to mate. Prepare antibiotic EM to collect eggs (100 µg/mL ampicillin, 5 µg/mL kanamycin, and 250 µg/ml amphotericin B, sterile filtered). Collect eggs in antibiotic EM and place in 30° C. incubator until they reach shield stage.
2. Move embryos into sterile 50-mL beaker. Wash embryos 3× in sterile EM. Immerse embryos in 0.1% PVP-I solution for 2 minutes. Rinse 3× in sterile EM. Transfer embryos to a new sterile 50-mL beaker and immerse in 0.003% bleach for 20 minutes. Pour off bleach and rinse 3× in sterile EM. Transfer 15 embryos into 50-mL sterile cell culture flasks with 15-mL sterile EM.

Day 5 (3 dpf):
1. Start overnight bacterial cultures. Start 50-mL cultures of any of the bacteria whose CFS you want to test for anti-inflammatory activity. Additionally start cultures that you need to induce inflammation, for example *A. veronii* or *Vibrio*. I estimate that a person could reasonably test 8 to 10 different bacterial CFS preparations in one experiment.

Day 6 (4 dpf):
1. Follow CFS preparation protocol listed above.
2. Visually check GF fish flasks for bacteria.
3. Inoculate flasks with $10^6$ cfu/ml bacteria (either *A. veronii* or *Vibrio*) and in some also include 500 ng/ml concentrated CFS. For each experiment, include one flask with no additional protein as a control and a GF flask as a control. Collect 1-mL of flask water before inoculation to plate and confirm that flasks were germ free at the start of the experiment.

Day 8 (6 dpf):
1. Check the plates with the inoculation water to ensure the flasks were germ-free before you started.
2. One flask at a time, add tricaine to the fish to anesthetize them. Rub 5% methylcellulose on a microscope slide. Use a glass pipette to carefully pull each fish out of the flask and place it on the prepared slide. Use the pipette to pull off any excess EM from the slide.
3. Under a dissecting microscope, use dissecting needles to pull the gut out of the fish, keeping it intact. Using a fluorescence microscope, visualize the GFP with a 395-nm light and count the number of neutrophils that are associated with the gut. Repeat steps 2 and 3 for 10-15 fish per each CFS treatment.

Example 6

Testing of AP in Zebrafish Models of Disease

This example describes particular methods that can be used to test the effect of AP on inflammation in zebrafish models of gut disease. However, one skilled in the art will appreciate that methods that deviate from these specific methods can also be used to successfully test the effect of AP on inflammation in zebrafish.

Zebrafish are treated with AP (for example, purified protein or CFS from *E. coli* expressing AP) and one or more markers of inflammation in the gut are determined. A reduction of one or more markers of inflammation in fish treated with AP as compared to control (untreated fish) indicates that AP decreases inflammation in the zebrafish gut.

In one example, a zebrafish model of Hirschsprung disease is used. These zebrafish have a mutation in a transcription factor, which results in a lack of peristalsis and a significant increase in gut inflammation over WT fish. This line is crossed with mpo: GFP zebrafish. The fish are raised conventionally and treated with the AP-enriched CFS (e.g., 500-1000 ng/mL) on 4 dpf. On 6 dpf the guts are dissected and the number of infiltrating neutrophils in the gut is counted (for example, by detecting GFP). A reduction in neutrophil influx to the gut in AP-treated fish compared to the untreated fish indicates that this protein reduces inflammation in a model of Hirschsprung disease.

In another example, larval zebrafish exposed to trinitrobenzene sulfonic acid (TNBS) have impaired intestinal homeostasis and inflammation that models what is observed in human inflammatory bowel disease (IBD). To test the activity of AP in this model, conventionally raised 3 dpf mpo:GFP zebrafish are placed in groups of 15 fish in 15-mL EM and TNBS is added to a final concentration of 100 µg/mL. On 4 dpf the fish are treated with 500 ng/mL to 1000 ng/mL AP-enriched CFS from the induced *E. coli* expressing anti-inflammatory protein AP. On 6 dpf the guts are dissected and the number of infiltrating neutrophils in the gut is counted (for example, by detecting GFP). A reduction in neutrophil influx to the gut in AP-treated fish compared to the untreated fish indicates that this protein reduces inflammation in a model of IBD.

Example 7

Testing of AP in Mice

This example describes particular methods that can be used to test the effect of AP on inflammation in mice. However, one skilled in the art will appreciate that methods that deviate from these specific methods can also be used to successfully test the effect of AP on inflammation in mice Adult mice are placed on three, 3-day cycles of 3% Dextran Sulfate Sodium (DSS) (Whittem et al., *J. Vis. Exp.* 35:6-8, 2010) with seven days of recovery between each cycle. A baseline weight for each mouse is obtained prior to DSS treatment and mice are weighed regularly during the experiment. As a positive control, additional mice are administered mouse IL-1ra (Sigma), which has been shown to alleviate inflammatory symptoms and neutrophil infiltration (reviewed in Rolig et al., *Infect. Immun.* 81:1382-1389, 2013). Treatment with AP is administration of 50-1000 ng/ml of purified AP added to the drinking water during the DSS treatment cycles. After the final recovery period, each mouse is weighed, sacrificed, and necropsied. In necropsy, the colon is removed and the length is documented, then fixed in 4% paraformaldehyde. Samples are embedded in paraffin, mounted, sectioned, and stained with hematoxylin and eosin for histologic analysis. Pathology is scored, including inflammation severity and epithelial cell integrity in the experimental and control colons (for example, in a double blind fashion). The ability of AP to alleviate inflammation in the colon is compared to exogenous mouse IL-1ra. Specific markers of inflammation are also evaluated, for example, Ly6B.2 (neutrophils), F4/80 (macrophages), and Ki67 (proliferation). Effectiveness of AP in mice may be indicated by decreased weight loss, increased colon length, and/or decreased pathologic and histologic markers of inflammation compared to mice treated with DSS alone (no AP treatment).

Example 8

Method of Treating or Inhibiting Inflammation

This example describes particular methods that can be used to treat or inhibit inflammation in a subject. However, one skilled in the art will appreciate that methods that deviate from these specific methods can also be used to successfully treat or inhibit inflammation in a subject.

Based upon the teaching disclosed herein, inflammation or an inflammatory disease can be treated or inhibited by administering an effective amount of a composition including an *Aeromonas* anti-inflammatory protein, a nucleic acid encoding the protein, or a preparation including bacteria that produce the protein to a subject with inflammation or an inflammatory disease.

In an example, a subject with an inflammatory disease is identified and selected for treatment. For example, a subject diagnosed with inflammatory bowel disease may be selected for treatment. Following subject selection, an effective dose of the composition or preparation including the anti-inflammatory protein, nucleic acid, or bacteria described above is administered to the subject. The amount of the composition or preparation administered to prevent, reduce, inhibit, and/or treat inflammation or an inflammatory disease depends on the subject being treated, the severity of the disorder, and the manner of administration of the composition. Ideally, an effective amount of an agent is the amount sufficient to prevent, reduce, and/or inhibit, and/or treat the condition (e.g., inflammatory disease) in a subject without causing substantial adverse effects in the subject.

In one specific example, an anti-inflammatory protein (such as SEQ ID NO: 1) or a fragment thereof (such as amino acids 148-176 of SEQ ID NO: 1) is administered to a subject. For example, an anti-inflammatory protein is administered to a subject at about 1 mg to 1 g daily. In another example, an anti-inflammatory protein is administered at about 1 mg to 1 g biweekly or weekly. In further examples, a nucleic acid encoding an anti-inflammatory protein (such as SEQ ID NO: 2) is administered to a subject at about 1 mg to 1 g daily, biweekly, or weekly. An appropriate dose can be selected by a skilled clinician based on the subject, the condition being treated and other factors.

Subjects are monitored by methods known to those skilled in the art to determine responsiveness of the inflammation or inflammatory disease treatment. For example, if the condition is inflammatory bowel disease, the symptoms of the subject are monitored, for example using the Crohn's Disease Activity Index or the Harvey-Bradshaw Index. It is contemplated that additional agents can be administered, such as additional anti-inflammatory agents in combination with or following treatment with the *Aeromonas* anti-inflammatory protein.

Example 9

Identification of Calycin-Like Domains in AimA

Materials and Methods

Protein Purification and Crystallization: AimA gene was PCR amplified from gDNA excluding the N-terminal (22 amino acid) secretion signal and cloned into pET21b using NdeI and XhoI restriction sites. The resultant gene expressed well in *E. coli* BL21 as a C-terminal 6×His tagged protein of 300 amino acids long (including His tag and linker).

The *E. coli* culture was grown at 37° C. until OD600 0.4-0.6, then moved to 30° C. and induced with 1 mM IPTG for 3-4 hr. All subsequent steps were performed at 4° C. One to two liters of pelleted *E. coli* cells were lysed in lysis buffer (50 mM HEPES pH 7.9, 300 mM NaCl, 10 mM imidazole, and 5 mM BME), sonicated, and debris pelleted. The supernatant was washed over 5 mL Ni-NTA resin in a gravity column that was pre-washed with lysis buffer. The resin was washed with 15× bed volume of lysis buffer, then 10× bed volume of lysis buffer with 30 mM imidazole, 10× bed volume of lysis buffer with 50 mM imidazole and finally eluted with 3×-5× bed volume of lysis buffer plus 100-300 mM imidazole. The high absorbance (280 nm wavelength) fractions were pooled and dialyzed overnight into 150 mM NaCl, 50 mM HEPES pH 7.9, and 5 mM BME, concentrated, and flash frozen in liquid nitrogen.

Purified AimA with C-terminal 6×His tag was concentrated to 10.9 mg/mL and set up in hanging drops as 1 µL protein:1 µL well solution at room temperature. AimA crystallized in thick hexagons in 3.5 M sodium formate, 75 mM NaCl, 25 mM HEPES pH 7.9, and 2.5 mM BME. One to two weeks after the crystals grew, they were transferred to wells containing 3.8 M sodium formate to toughen them up for approximately one week. The heavy atom derivative crystals were then transferred to drops with 3.8 M sodium formate, 0.5 M NaI (for iodide data set), and 15% glycerol (as a cryoprotectant) for several hours before being scooped and flash frozen in liquid nitrogen for data collection at the Advanced Light Source in Berkley, Calif., beamline 5.0.2 using the Pilatus detector at a wavelength of 1.0 A. The native crystals were transferred to 3.8M sodium formate and 15% PEG 200 briefly, then flash frozen in liquid nitrogen for data collection as described for the iodide soaked crystals.

Structure determination of AimA Data Processing: The heavy atom derivative was solved by the single-wavelength anomalous diffraction (SAD) method from a single crystal derivatized with I⁻, with data collected at wavelength $\lambda=1$ Å. The data set was integrated and scaled to resolution 2.7 Å using HKL3000 (Minor et al., *Acta Crystallogr Sect D Biol Crystallogr.* 2006; 62:859-866) with the merging analysis indicating the P622 space group. Although data were isotropic, diffraction spots were smeared in a manner indicating the presence of order-disorder. In addition, the scaling B-factor increase of ~40 Å$^2$, which is equivalent to a dose of ~40 MGy, indicated severe radiation damage. Therefore, it was necessary to apply the 'automatic corrections' computational procedure to optimize the error model (Borek et al., *Acta Crystallogr Sect D Biol Crystallogr.* 2010; 66:426-36; Borek et al., *J Synchrotron Radiat.* 2013; 20:37-48; Borek et al., *J Synchrotron Radiat.* 2007; 14:24-33), and this was essential for the success of the experimental phasing described below.

The estimated level of anomalous signal was ~3.6% of the native intensity. The search for heavy atom positions was performed to a resolution of 3.7 Å. The 30 positions of I⁻ were identified using SHELXC/D (Sheldrick, *Acta Crystallogr Sect D Biol Crystallogr.* 2008; 64:112-122), run within HKL3000, with correlation coefficients: $CC_{All}=41.4\%$, $CC_{Weak}=16.1\%$. The handedness of the best solution was determined with SHELXE. The heavy atom positions were refined to 2.7 Å with MLPHARE (Otwinowski, Pap Present CCP4 Study Weekend. 1991) with the final Figure of Merit (FOM) reaching 0.14 for all observations. Solvent flattening was performed by DM (Cowtan et al., *Acta Crystallogr Sect*

D Biol Crystallogr. 1998; 54: 487-493). The procedure produced an interpretable electron density map that was used for iterative automatic model building with BUCCANEER, Coot and REFMAC (Cowtan, Acta Crystallogr Sect D Biol Crystallogr. 2006; 62:1002-1011; Emsley et al., Acta Crystallogr Sect D Biol Crystallogr. 2004; 60:2126-2132; Murshudov et al., Acta Crystallogr Sect D Biol Crystallogr. 1997; 53:240-255; Murshudov et al., Acta Crystallogr Sect D Biol Crystallogr. 1999; 55:247-255)—all run within HKL3000 with 'HKL Builder' option. That procedure resulted in 100% of the model being built with 90% of the side chains docked. At this point, the R and R-free factors were ~27% and ~35%, respectively.

Two native AimA datasets from separate crystals were indexed and integrated with iMosflm 7.2.1 (Battye et al., Acta Crystallogr D Biol Crystallogr. 2011; 67:271-281) and scaled using SCALA (Collaborative Computational Project N 4, Acta Crystallogr D Biol Crystallogr. 1994; 50:760-763). The two datasets were found to be isomorphous, and were combined using POINTLESS (Collaborative Computational Project N 4, Acta Crystallogr D Biol Crystallogr. 1994; 50:760-763). The high-resolution cutoff was determined by the method of Karplus & Diederichs (Science 2012; 336:1030-1033) using a $CC_{1/2}$ of >0.3 and completeness of >50% in the highest resolution shell. This method has been utilized in numerous other studies (Perkins et al., Structure 2016; 24: 1668-1678; Evans et al., Acta Crystallogr D Biol Crystallogr. 2013; 69:1204-1214; Kern et al., Science 2013; 340: 491-495) and has been cited over 900 times since its publication. Using these criteria, the correlation between two halves of the data are used to determine the point at which signal falls away into noise (Evans et al., Acta Crystallogr D Biol Crystallogr. 2013; 69:1204-1214), and $R_{merg}$ values can rise to values much higher than what has traditionally been thought of as allowable. Using this strategy we were able to extend the resolution from 2.9 Å (where the data would have been cut based on $R_{merg}$~0.6) to 2.3 Å. To further test the validity of using this noisy high-resolution data to refine the model, a series of paired refinements were conducted (Karplus & Diederichs, Science 2012; 336:1030-1033). The model was first refined using data out to 2.9, 2.7, 2.5, or 2.3 Å and then, since R values are only comparable when calculated at the same resolution (Karplus & Diederichs, Science 2012; 336:1030-1033), R and $R_{free}$ were calculated for each refined model at 2.9 Å (FIG. 12). The extra resolution improved both R (higher value) and $R_{free}$ (lower value), showing that the model is improved in predictive quality and is less overfit using the extended resolution cutoff. In this case $CC_{1/2}$ remains quite high at 0.9 in the high-resolution shell, and the <I/σ> at 1.4 is not far below a traditional cutoff of 2.0. Data statistics are summarized in Table 2.

Refinement: Manual model building was performed using Coot 0.8.1.6 (Emsley et al., Acta Crystallogr Sect D Biol Crystallogr. 2004; 60:2126-2132) and refinement was carried out using PHENIX 1.12-2829 (Adams et al., Acta Crystallogr Sect D Biol Crystallogr. 2010; 66:213-221). Initial rigid body refinement resulted in $R/R_{free}$ values of 26.5/28.3%. Using the extended resolution improved the electron density maps and allowed placement of additional water molecules, two formate molecules (present at 3.5 M in the crystallization buffer), N-terminal residues 1-8, and an alternate chain path for residues 153-165, improving $R/R_{free}$ to 20.9/24.8%. Residues 180-181 are at the tip of a disordered loop and were not modeled, and residues 293-294 and the C-terminal His-tag beyond it are not visible in the electron density. Electron density is weak in several regions including the N-terminus and several loops, but the chain path was clear enough to build at least the backbone atoms for these residues. In late stages of refinement, TLS was implemented using one group per chain, dropping $R/R_{free}$ to 17.9/20.9%. B-factor weights were optimized in the final refinement step, yielding final $R/R_{free}$ of 17.2/20.4% for the final AimA model (Table 2).

TABLE 2

Data Collection and Refinement Statistics for Model

| Data Collection | Iodide | | | Native | | |
|---|---|---|---|---|---|---|
| Space group | P622 | | | P622 | | |
| Unit cell a, b, c (Å) | 161.4 | 161.4 | 66.6 | 160.5 | 160.5 | 66.2 |
| Alpha, beta, gamma (degrees) | 90 | 90 | 120 | 90 | 90 | 120 |
| Resolution (Å) | 50.0-2.7 (2.75-2.70) | | | 41.1-2.30 | | |
| Completeness (%) | 100 (100) | | | 100 (100) | | |
| No. unique reflections | 14772 (711) | | | 22818 (3244) | | |
| Multiplicity | 37.7 (38.1) | | | 70.2 (71.6) | | |
| <I/sigma> | 44.2 (3.5) | | | 16.1 (1.4) | | |
| CC1/2 | 1 | 0.861 | | 1.0 (0.9) | | |
| CC1/2 anomolous | 1 | 0.873 | | | | |
| R merge (%) | 19.6 (486) | | | 19.1 (574) | | |
| Refinement | | | | | | |
| R work (%) | | | | 17.2 | | |
| R free (%) | | | | 20.4 | | |
| No. of molecules in the asymmetric unit | | | | 1 | | |
| No. protein residues | | | | 290 | | |
| No. of waters | | | | 69 | | |
| rmsd for lengths (Å) | | | | 0.008 | | |
| rmsd for angles (deg) | | | | 1.1 | | |
| Ramachandran plot (%) | | | | | | |
| Preferred | | | | 96.2 | | |
| Allowed | | | | 3.4 | | |
| Outliers | | | | 0.4 | | |
| Avg. B factor (Å^2) | | | | | | |
| Mainchain[A] | | | | 81 | | |
| Waters | | | | 75 | | |

[A] Several loop regions display high mobility but have been modeled due to a visible chain path in the electron density, resulting in an increase in the average observed B-factors of the main chain Results Analysis of the amino acid sequence of AimA with the N terminal amino acid secretion signal removed revealed a lack of sequence identity with known domains or structurally characterized proteins and therefore offered little insight into the structure or function of AimA. To gain insight into the mechanism of AimA, we constructed a recombinant protein with a C-terminal His-tag. His-tagged AimA produced in E. coli was purified and crystallized to determine the molecular structure using a heavy atom derivative and Single-wavelength Anomalous Dispersion (SAD) phasing to a resolution of 2.3 Å (Table 2). The structure of AimA revealed two domains connected by a short linker (FIGS. 13A and 13B). β-strands dominate each domain, with the carboxy terminal (C-term) domain forming a complete β-barrel and the amino terminal (N-term) domain containing a curved β-sheet. Structural homology searches of full length AimA against all Protein Data Bank-deposited structures using PDBeFold resulted in structures that aligned to only one domain or the other, with the majority aligning with the C-term domain (Krissinel et al., *Acta Crystallogr Sect D Biol Crystallogr;* 2004; 60:2256-2268; Berman et al., *Nucleic Acids Res.* 2000; 28:235-242). Therefore, we performed structural homology searches against each domain separately, which revealed that both domains had similarity to proteins in the calycin superfamily (Table 3 and FIGS. 14A-14B). The calycin superfamily is found across all domains of life and includes lipocalins, fatty acid binding proteins, and avidins. This superfamily is defined by an anti-parallel β-barrel with a repeated +1 topology (Flower, *Biochem J.* 1996; 318 (Pt 1: 1-14). Notably, the calycin superfamily is known for structural conservation without high amino acid sequence conservation (Flower, *Biochem J.* 1996; 318 (Pt 1: 1-14); Lakshmi et al., *PLoS One.* 2015; 10:1-18), which helps explain the lack of sequence homology for AimA. The N-term domain of AimA has an incomplete β-barrel, but maintains some structural homology to streptavidin. Streptavidin binds biotin tightly, but AimA does not appear to bind biotin (FIGS. 14C-14D). The C-term domain of AimA has structural homology both to avidins and lipocalins (Table 3). Some lipocalin proteins, like human lipocalin-2, or NGAL, are known to influence neutrophil behavior (Moschen et al., *Trends Endocrinol Metab.* 2017; 28:3880397).

3-4 hours before being washed into fresh EM. For experiments with mLCN2, recombinant mouse LCN2 (Biolegend) was added to the fish EM at a concentration of 100 ng/mL after the soysaponin feeding on 4 dpf and 5 dpf after the fish were moved into fresh EM.

Results

To test whether AimA may interact directly with the host, we tested AimA function in a general model of intestinal inflammation, the zebrafish model of soysaponin-induced inflammation. Farmed fish, such as salmon and carp, fed soybean meal as a protein source are known to develop intestinal inflammation, and zebrafish are a good model of this irritation (Hedrera et al., *PLoS One.* 2013; 8:1-10). We fed conventionally raised zebrafish larvae Zieglers fish food with 0.3% soysaponin from 4 dpf to 6 dpf and saw a significant increase in the number of intestinal neutrophils in response to the soysaponin, as expected (FIG. 15A). When we treated the fish with 100 ng/ml purified AimA from 4 dpf to 6 dpf concurrently with soysaponin, AimA prevented the increase in neutrophil influx in response to soysaponin (FIG. 15A). This result may suggest that AimA interacts directly with the host immune system, which makes AimA a good candidate for a therapeutic bioactive protein that reduces host inflammation.

Because AimA reduces neutrophil influx in a model of intestinal inflammation and the C-term domain has structural

TABLE 3

Structural homology hits to each AimA domain

| AimA domain | Protein | Organism | PDB ID | Q score | RMSD |
|---|---|---|---|---|---|
| Amino terminal (19 total hits) | Engineered Streptavidin | *Streptomyces avidinii* | 1kl3 | 0.18 | 2.69 |
| | Avidin | *Gallus gallus* | 1lel | 0.16 | 3.56 |
| | Zebavidin | *Danio rerio* | 4bj8 | 0.15 | 3.15 |
| Carboxy terminal (220 total hits) | Avidin | *Gallus gallus* | 1lel | 0.32 | 2.58 |
| | Zebavidin | *Danio rerio* | 4bj8 | 0.32 | 2.58 |
| | Lipocalin lipoprotein | *Streptococcus pneumonia* | 5cyb | 0.29 | 2.28 |
| | Lipoprotein | *Treponema pallidum* | 4u3q | 0.26 | 2.09 |
| | Streptavidin | *Streptomyces avidinii* | 2izf | 0.26 | 2.77 |
| | Retinol binding protein 4 | *Homo sapiens* | 4o9s | 0.18 | 2.89 |
| | Lipocalin-2 (LCN2, NGAL) | *Homo sapiens* | 3i0a | 0.16 | 3.07 |
| | Engineered Streptavidin | *Streptomyces avidinii* | 1kl3 | 0.18 | 2.69 |

| Protein families | Q score range | RMSD range |
|---|---|---|
| Avidins | 0.32-0.17 | 2.58-2.87 |
| Bacterial lipocalins | 0.29-0.21 | 2.28-2.85 |
| | 0.26- | 2.09- |
| Non-bacterial lipocalins | 0.16 | 3.07 |

Example 10

Effect of AimA in a Zebrafish Model of Inflammation

Methods

Soysaponin (Sigma-Aldrich, St. Louis, Mo.) was mixed with Zieglers fish food at a concentration of 0.3%. Ten CV zebrafish were maintained 10 mL EM in 60×15 mm petri dishes. Larval fish were fed once daily from 4 dpf to 6 dpf. During each feeding, the larvae had access to the food for homology to lipocalin proteins (FIGS. 4, 5A, and 8; Table 3), we hypothesized that the neutrophil reducing capacity of AimA was related to its lipocalin-like structure. Lipocalins are defined by three key structurally conserved regions (SCR1, SCR2, SCR3); the most conserved region is SCR1, which is conserved across kernel and outlier lipocalins and contains four key residues (FIG. 15B) (Flower, *Biochem J.* 1996; 318 (Pt 1: 1-14); Lakshmi et al., *PLoS One.* 2015; 10:1-18). The SCR1 in the C-term domain of AimA structurally overlaps with the SCR1 of mouse lipocalin-2 (mLCN2) (FIG. 15B). Thus, we asked whether the addition of mLCN2 protein would hinder the capacity of AimA to reduce the neutrophil response to soysaponin. The addition of mLCN2 concurrently with soysaponin did not influence the neutrophil response to soysaponin (FIG. 15C); however, addition of mLCN2 in conjunction with AimA prevented the protective effect of AimA against soysaponin-induced inflammation, suggesting that AimA may bind mLCN2, compete for the same host receptor, or act in a competing pathway.

Both the C- and N-terminal domains of AimA have structural homology to proteins in the calycin superfamily, they share 16% amino acid identity, and in a structural overlay between the two domains we find some structural conservation (FIG. 16A and FIG. 17A). Human lipocalin-2 can exist both as a monomer and a homodimer, and while the functional distinction between the two forms is unknown, the homodimer is the major molecular form secreted by neutrophils (Cai et al., *Clin J Am Soc Nephrol.* 2010; 5:2229-2235). Because human lipocalin-2 exists as both a monomer and a homodimer, and the two domains of AimA each have a lipocalin-like fold, we asked if each domain alone was sufficient to alter the intestinal neutrophil response. The individual domains were not as soluble as full-length AimA, but we were able to crudely purify each domain with an N-terminal His-tag. Concurrently with soysaponin, we added approximately 100 ng/ml of the domain of interest to zebrafish from 4 to 6 dpf and found that both the N- and C-term domains were sufficient to reduce neutrophil response in the soy model of intestinal inflammation (FIG. 16B).

An in depth analysis of the structural overlay between the N- and C-term domains revealed that seven out of eight β-strands in the barrels align well; however, only seven total residues are in analogous positions across the two domains (FIGS. 17B and 17C). Of these seven residues, two—Val 60/201 and Thr 117/265—stand out as possible candidates to interact with a hydrophobic ligand that binds inside the barrel cavity. The other five residues may overlap by coincidence or they may be positioned to interact with a promiscuous protein or ligand partner. Furthermore, given the overall structural similarity between the N- and C-term domains, it is possible that critical residues are in a flexible loop region that could become structured upon binding (FIG. 16A, FIGS. 17A-17C). Interestingly, both AimA domains have comparable structural similarity with mLCN2 (FIG. 16C). In all three domains, the majority of the β-strands in the barrels overlap and there is a similar cleft inside the barrels, which suggests these domains could interact with the same receptor or ligand (FIG. 16C). These insights into the potential molecular mechanism of AimA could not have been achieved with sequence alone.

Example 11

Effect of AimA on *Aeromonas* Fitness

With an understanding that AimA controls the host neutrophil response, we next asked whether the activity of AimA also increases *Aeromonas* fitness, thus facilitating the establishment of a mutualistic relationship with the host. We began by asking how prevalent AimA was across bacterial genomes. Knowing that proteins in the calycin superfamily have low sequence conservation, we were not surprised to find AimA homologues by sequence similarity only within the *Aeromonas* genus (FIGS. 18A and 18B). These homologues ranged from 27% to 100% in amino acid sequence conservation. Some species of *Aeromonas*, including *A. veronii* strain Hm21 (Table 4), have both AimA and a second copy, which we named AimB. AimB is distantly related to AimA by amino acid sequence conservation (27%), yet an Iterative Threading ASSEmbly Refinement (I-TASSER) generated model of the structure of AimB overlays directly on the structure of AimA (FIG. 19A) (Yang et al., *Nat Methods.* 2014; 12:7-8; Roy et al., *Nat Protoc.* 2011; 5:725-738; Zhang, *BMC Bioinformatics.* 2008; 9:40). This is consistent with the low sequence conservation but high structural conservation of proteins within the calycin superfamily. We additionally found an almost identical homologue (99%) to AimA in a zebrafish commensal *Aeromonas* isolate, ZOR0001, referred to here as ZF Aer (Table 4) (Stephens et al., *ISME J.* 2015; 10).

TABLE 4

Strain table

| Strain | Characteristics | Ref. or source | Abbreviation |
|---|---|---|---|
| Hm21S | Parent strain, Sm$^R$ | Graf, 1999[1] | Aer |
| HE-1095 | Hm21S::interrupted exeM mTn5 Km$^R$ Sm$^R$ | Graf, 2011[2] | Aer ΔT2 |
| HEC-1344 | HE-1095::Tn7 containing Tp$^R$ exeMN + promoter region | Graf, 2011[2] | Aer ΔT2C |
| ASRC7 | Hm21S aimA::cm$^R$ | | Aer ΔaimA |
| ASRD5 | Hm21S ΔaimB | | Aer ΔaimB |
| ASRD4 | Hm21S aimA::cm$^R$; ΔaimB | | Aer ΔAΔB |
| ZOR0001 | Zebrafish *Aeromonas* isolate | Stephens[3] | ZF Aer |
| ASRC9 | ZOR0001 aimA::cmR | | ZF Aer ΔaimA |

[1]Graf, *Infect. Immun.* 67:1-7, 1999
[2]Maltz and Graf, *Appl. Environ. Microbiol.* 77:597-603, 2011
[3]Stephens et al., ISME J. 10:644-654, 2016

Figure 19E:
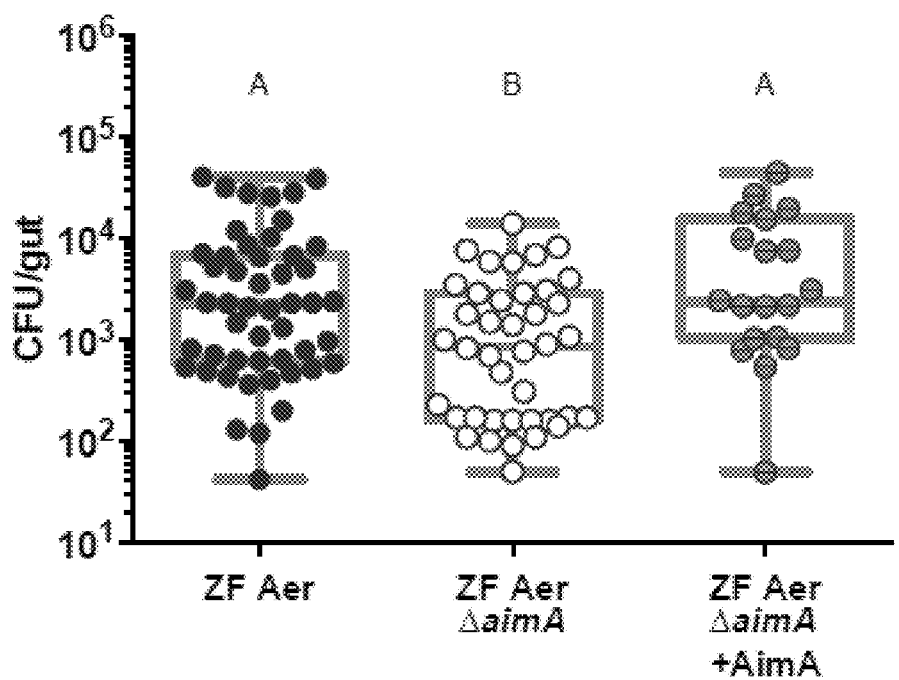

To determine whether the bioactive protein AimA and its homolog AimB benefit *Aeromonas*, we constructed deletion strains of each gene individually and of both genes in *A. veronii* strain Hm21 (Aer ΔaimA, Aer ΔaimB, and Aer ΔAΔB), and an AimA deletion in the ZF Aer background (ZF Aer ΔaimA). All of these mutants displayed normal growth in vitro (FIG. 18B). Purified AimA reduces the intestinal neutrophil response, thus we hypothesized that the deletion strains would have a greater capacity to induce a neutrophil response. To test our hypothesis, we mono-associated each of these strains in zebrafish from 4 to 7 dpf and quantified both intestinal neutrophil number and bacterial colonization level on 7 dpf. We found that in *A. veronii* strain Hm21, which has both AimA and AimB, neither single deletion was different from wild type in either host neutrophil response (FIG. 19B) or bacterial colonization (FIG. 19C). However, the double mutant that lacks both AimA and AimB induced a significantly greater intestinal neutrophil response than the wild type (FIG. 19B) and suffered a significant colonization defect (FIG. 19C), suggesting that AimA and AimB have redundant functions. Further, the phenotypes observed in Aer ΔAΔB can be rescued in trans by adding purified AimA protein at a concentration of 100 ng/mL to the flask water with mono-associated zebrafish from 4 to 7 dpf (FIGS. 19B and 19C). We were able to replicate these phenotypes in ZF Aer ΔaimA strain and rescue them by adding purified AimA (FIGS. 19D and 19E). These results also reveal that in the absence of Aim proteins, fewer *Aeromonas* cells are required to induce a larger neutrophil response, suggesting that each ΔAΔB bacterial cell has a higher per capita effect on neutrophil influx than wild-type *Aeromonas*.

Example 12

Effect of AimA on Host Survival

To induce sepsis, CV zebrafish were treated with 600 µg/mL LPS (Sigma-Aldrich, St. Louis, Mo.) on 5 dpf and monitored for survival for the following 2 days. For experiments with AimA, AimA was added at 100 ng/ml on 4 dpf.

In the absence of Aim proteins, Aer ΔAΔB infection had both reduced colonization and induces an increased intestinal neutrophil response, which suggests that Aer ΔAΔB has a higher per capita effect than the wild-type *Aeromonas* strain. We calculated the number of neutrophils that respond to $10^4$ colonized bacteria, and discovered that Aer ΔAΔB recruits nearly twice the number of neutrophils than the wild-type strain, on average, for the same number of bacteria (FIG. 20A). This demonstrates that the Aim proteins may function, in part, to reduce the immune stimulation potential of *Aeromonas*, allowing *Aeromonas* to conceal their high colonization numbers from the host. Thus, AimA allows the bacteria to reach higher colonization density without a detriment to the host.

Knowing that loss of the Aim proteins resulted in both a significantly higher per capita effect and a significantly increased intestinal neutrophil response, we asked if the increased neutrophil response led to more serious health problems. Thus, as a representation of overall fish health, we monitored mono-associated fish for their survival rate over 72 hours. By 72 hours, the survival rate of wild-type Aer was 92% (n=163). We observed a significant decline in the survival of Aer ΔaimA (n=139), Aer ΔaimB (n=174), and Aer ΔAΔB (n=148), whose survival rates were 64%, 73%, and 55%, respectively (FIG. 20B). This decreased survival rate was rescued back to 90% by the presence of purified AimA (n=60; FIG. 20C). These data demonstrate that the Aim proteins act to promote both bacterial colonization and host survival, identifying AimA as a key mediator of host-bacterial mutualism.

We tested whether the ability of AimA to control the neutrophil response was connected to the decreased survival rate by inoculating myd88$^{-/-}$ transgenic fish with wild-type *Aeromonas* or Aer ΔAΔB. myd88$^{-/-}$ fish lack the adaptor protein Myd88 that is used by almost all toll-like receptors (TLRs) to activate pro-inflammatory transcription pathways (Larsson et al., *Gut.* 2011; doi:10.1136/gutjnl-2011-301104); the lack of Myd88 results in fish with a severely attenuated intestinal neutrophil response, such that their intestinal neutrophil response is not distinguishable from germ-free wild-type zebrafish (Bates et al., *Cell Host Microbe.* 2007; 2:371-82; Burns et al., *Proc Natl Acad Sci.* 2017; 201702511. doi:10.1073/pnas.1702511114) (FIG. 20C). However, myd88$^{-/-}$ fish inoculated with Aer ΔAΔB do not die at a higher rate than those inoculated with wild-type *Aeromonas* (FIG. 20D), suggesting that the increased neutrophil response to Aer ΔAΔB is connected to the decreased survival rate. We additionally found that not only do Aer ΔAΔB not experience a colonization defect in myd88$^{-/-}$ fish, the colonization level of both Aer ΔAΔB and wild-type Aer increased significantly in the myd88$^{-/-}$ fish compared to wild-type fish (FIG. 20E). These results suggest that the decreased colonization of Aer ΔAΔB in wild-type fish is due to the increased neutrophil response and that the neutrophil response functions, in part, to control the colonization density of commensal bacteria.

Given the increase in bacterial colonization and fish death in the myd88$^{-/-}$ fish, regardless of the colonizing strain, we hypothesized that these fish may be dying of sepsis as a result of bacterial overgrowth. Thus we asked whether AimA could delay death as a result of LPS exposure, a model of bacterial sepsis in zebrafish (Philip et al, *Mol Med.* 2017; 23:1). To test this, we treated fish with 100 ng/mL AimA on 4 dpf then with 600 µg/mL LPS on 5 dpf and tracked their survival over the subsequent 60 hours. Indeed, the median survival time post LPS treatment was 36 hours, which was extended to 48 hours in the presence of AimA (FIG. 20F). Thus, AimA significantly extends the survival of LPS treated fish.

Example 13

Method of Treating or Inhibiting Sepsis or Septic Shock

This example describes particular methods that can be used to treat or inhibit sepsis or septic shock in a subject. However, one skilled in the art will appreciate that methods that deviate from these specific methods can also be used to successfully treat or inhibit sepsis or septic shock in a subject.

Based upon the teaching disclosed herein, sepsis or septic shock can be treated or inhibited by administering an effective amount of a composition including an *Aeromonas* anti-inflammatory protein or portion thereof, a nucleic acid encoding the protein or portion thereof, or a preparation including bacteria that produce the protein or portion thereof, to a subject with sepsis or septic shock or suspected to have sepsis or septic shock.

In an example, a subject with sepsis or septic shock or suspected to have sepsis or septic shock is identified and selected for treatment. Following subject selection, an effective dose of the composition or preparation including the anti-inflammatory protein, nucleic acid, or bacteria described above is administered to the subject. The amount of the composition or preparation administered to prevent, reduce, inhibit, and/or treat sepsis or septic shock depends on the subject being treated, the severity of the disorder, and the manner of administration of the composition. Ideally, an effective amount of an agent is the amount sufficient to prevent, reduce, and/or inhibit, and/or treat sepsis or septic shock in the subject without causing substantial adverse effects in the subject.

In one specific example, an anti-inflammatory protein (such as SEQ ID NO: 1 or SEQ ID NO: 11) or a fragment thereof (such as amino acids 1-185, 23-185, and/or 192-313 of SEQ ID NO: 1, or amino acids 1-188, 21-188, and/or 189-330 or SEQ ID NO: 11) is administered to a subject. For example, an anti-inflammatory protein is administered to a subject at about 1 mg to 1 g daily. In another example, an anti-inflammatory protein is administered at about 1 mg to 1 g biweekly or weekly. In further examples, a nucleic acid encoding an anti-inflammatory protein (such as SEQ ID NO: 2 or SEQ ID NO: 17) or a fragment thereof (such as nucleotides 1-555, 67-555, and/or 574-939 of SEQ ID NO: 2 or nucleotides 1-564, 61-564, and/or 565-990 of SEQ ID NO: 17) is administered to a subject at about 1 mg to 1 g daily, biweekly, or weekly. An appropriate dose can be selected by a skilled clinician based on the subject, the condition being treated and other factors.

Subjects are monitored by methods known to those skilled in the art to determine responsiveness of the sepsis or septic shock to treatment. Additional agents can be administered, such as antibiotics, vasopressors, and/or intravenous fluids, in combination with or following treatment with the *Aeromonas* anti-inflammatory protein.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of treating inflammatory bowel disease, Hirschsprung's associated enterocolitis, irritable bowel syndrome, or necrotizing enterocolitis in a subject, comprising administering to the subject a polypeptide comprising:

an amino acid sequence comprising the amino acid sequence of SEQ ID NO: 11; or an amino acid sequence comprising amino acids 1-188 of SEQ ID NO: 11, amino acids 21-188 of SEQ ID NO: 11, or amino acids 189-330 of SEQ ID NO: 11.

2. The method of claim 1, wherein the polypeptide consists of:

the amino acid sequence of SEQ ID NO: 11; or the amino acid sequence of amino acids 1-188 of SEQ ID NO: 11, amino acids 21-188 of SEQ ID NO: 11, or amino acids 189-330 of SEQ ID NO: 11.

3. The method of claim 1, wherein the amount of the polypeptide administered to the subject is about 1 mg to about 5 g.

4. The method of claim 1, wherein the polypeptide is administered to the subject daily, weekly, or monthly.

5. The method of claim 1, further comprising administering one or more of a non-steroidal anti-inflammatory drug (NSAID), corticosteroid, or disease-modifying antirheumatic drug (DMARD) to the subject.

6. The method of claim 1, wherein the inflammatory bowel disease is ulcerative colitis or Crohn's disease.

* * * * *